(12) United States Patent
Brockunier et al.

(10) Patent No.: US 7,625,938 B2
(45) Date of Patent: Dec. 1, 2009

(54) SUBSTITUTED PYRAZOLES, COMPOSITIONS CONTAINING SUCH COMPOUNDS AND METHODS OF USE

(75) Inventors: Linda Brockunier, Orange, NJ (US); Jian Guo, Scotch Plains, NJ (US); Rui Liang, East Brunswick, NJ (US); Emma R. Parmee, Scotch Plains, NJ (US); Subharekha Raghavan, Teaneck, NJ (US); George Scott Tria, Princeton, NJ (US); Yusheng Xiong, Plainsboro, NJ (US)

(73) Assignee: Merck & Co., Inc., Rahway, NJ (US)

( * ) Notice: Subject to any disclaimer, the term of this patent is extended or adjusted under 35 U.S.C. 154(b) by 503 days.

(21) Appl. No.: 11/632,198

(22) PCT Filed: Jul. 19, 2005

(86) PCT No.: PCT/US2005/025541

§ 371 (c)(1),
(2), (4) Date: Jan. 17, 2007

(87) PCT Pub. No.: WO2006/014618

PCT Pub. Date: Feb. 9, 2006

(65) Prior Publication Data

US 2008/0108620 A1 May 8, 2008

Related U.S. Application Data

(60) Provisional application No. 60/590,172, filed on Jul. 22, 2004.

(51) Int. Cl.
*A61K 31/502* (2006.01)
*A61K 31/4155* (2006.01)
*C07D 241/36* (2006.01)
*C07D 403/04* (2006.01)

(52) U.S. Cl. .......... 514/406; 544/224; 544/336; 544/349; 544/353; 546/112; 546/252; 546/167; 548/152; 548/178; 548/356.1; 548/364.4; 548/364.7; 514/247; 514/249; 514/403

(58) Field of Classification Search ............ 544/224, 544/336, 338, 349, 353; 546/112, 152, 167; 548/152, 178, 356.1, 364.4, 364.7; 514/247, 514/249, 403, 406
See application file for complete search history.

(56) References Cited

U.S. PATENT DOCUMENTS

| | | |
|---|---|---|
| 5,776,954 A | 7/1998 | de Laszlo et al. |
| 6,218,431 B1 | 4/2001 | Schoen et al. |
| 6,503,949 B1 | 1/2003 | Lau et al. |
| 6,562,807 B2 | 5/2003 | Jorgensen et al. |
| 6,613,942 B1 | 9/2003 | Ling et al. |
| 6,762,318 B2 | 7/2004 | Kodra et al. |
| 6,790,810 B2 | 9/2004 | Yanagi et al. |
| 6,881,746 B2 | 4/2005 | Lau et al. |
| 2005/0171196 A1 | 8/2005 | Fujii et al. |

FOREIGN PATENT DOCUMENTS

| | | |
|---|---|---|
| WO | WO 97/16442 | 5/1997 |
| WO | WO 98/21957 | 5/1998 |
| WO | WO 98/22108 | 5/1998 |
| WO | WO 98/22109 | 5/1998 |
| WO | WO 00/39088 | 7/2000 |
| WO | WO 02/08188 A1 | 1/2002 |
| WO | WO 02/40444 A1 | 5/2002 |
| WO | WO 03/051357 A1 | 6/2003 |
| WO | WO 03/053938 A1 | 7/2003 |
| WO | WO 03/097619 A1 | 11/2003 |
| WO | WO 2004/002480 | 1/2004 |
| WO | WO 2004/009158 A2 | 1/2004 |
| WO | WO 2004/050039 A2 | 6/2004 |
| WO | WO 2004/069158 A3 | 8/2004 |
| WO | WO 2004/092146 A2 | 10/2004 |
| WO | WO 2004/100875 A2 | 11/2004 |
| WO | WO 2005/121097 A2 | 12/2005 |
| WO | WO 2007/047676 A1 | 4/2007 |

OTHER PUBLICATIONS

Kurukulasuriya, R., "Biaryl amide glucagon receptor antagonists", Bioorganic & Medicinal Chemistry Letters, vol. 14, pp. 2047-2050, 2004.

*Primary Examiner*—Golam M Shameem
(74) *Attorney, Agent, or Firm*—Richard C. Billups; Catherine D. Fitch

(57) ABSTRACT

The present invention relates to substituted pyrazoles, compositions containing such compounds and methods of treatment. The compounds are glucagon receptor antagonists and thus are useful for treating, preventing or delaying the onset of type 2 diabetes mellitus.

9 Claims, No Drawings

SUBSTITUTED PYRAZOLES, COMPOSITIONS CONTAINING SUCH COMPOUNDS AND METHODS OF USE

CROSS REFERENCE TO RELATED APPLICATIONS

This application is a US National Phase Application of PCT application No. PCT/US2005/025541 filed on 19 Jul. 2005, which was based upon U.S. Provisional Application No. 60/590,172 filed on Jul. 22, 2004, priority of which is claimed hereunder.

BACKGROUND OF THE INVENTION

The present invention relates to substituted pyrazole derivatives substituted with a bicyclic heteroaryl group, compositions containing such compounds and methods of treating type 2 diabetes mellitus.

Diabetes refers to a disease process derived from multiple causative factors and is characterized by elevated levels of plasma glucose (hyperglycemia) in the fasting state or following glucose administration during an oral glucose tolerance test. Frank diabetes mellitus (e.g., a blood glucose level $\geq$126 mg/dL in a fasting state) is associated with increased and premature cardiovascular morbidity and mortality, and is related directly and indirectly to various metabolic conditions, including alterations of lipid, lipoprotein and apolipoprotein metabolism.

Patients with non-insulin dependent diabetes mellitus (type 2 diabetes mellitus), approximately 95% of patients with diabetes mellitus, frequently display elevated levels of serum lipids, such as cholesterol and triglycerides, and have poor blood-lipid profiles, with high levels of LDL-cholesterol and low levels of HDL-cholesterol. Those suffering from Type 2 diabetes mellitus are thus at an increased risk of developing macrovascular and microvascular complications, including coronary heart disease, stroke, peripheral vascular disease, hypertension (for example, blood pressure$\geq$130/80 mmHg in a resting state), nephropathy, neuropathy and retinopathy.

Patients having type 2 diabetes mellitus characteristically exhibit elevated plasma insulin levels compared with nondiabetic patients; these patients have developed a resistance to insulin stimulation of glucose and lipid metabolism in the main insulin-sensitive tissues (muscle, liver and adipose tissues). Thus, Type 2 diabetes, at least early in the natural progression of the disease is characterized primarily by insulin resistance rather than by a decrease in insulin production, resulting in insufficient uptake, oxidation and storage of glucose in muscle, inadequate repression of lipolysis in adipose tissue, and excess glucose production and secretion by the liver. The net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

Glucagon serves as the major regulatory hormone attenuating the effect of insulin in its inhibition of liver gluconeogenesis and is normally secreted by α-cells in pancreatic islets in response to falling blood glucose levels. The hormone binds to specific receptors in liver cells that triggers glycogenolysis and an increase in gluconeogenesis through cAMP-mediated events. These responses generate glucose (e.g. hepatic glucose production) to help maintain euglycemia by preventing blood glucose levels from falling significantly.

In addition to elevated levels of circulating insulin, type II diabetics have elevated levels of plasma glucagon and increased rates of hepatic glucose production. Antagonists of glucagon are useful in improving insulin responsiveness in the liver, decreasing the rate of gluconeogenesis and lowering the rate of hepatic glucose output resulting in a decrease in the levels of plasma glucose.

SUMMARY OF THE INVENTION

The present invention is directed to a compound represented by formula I:

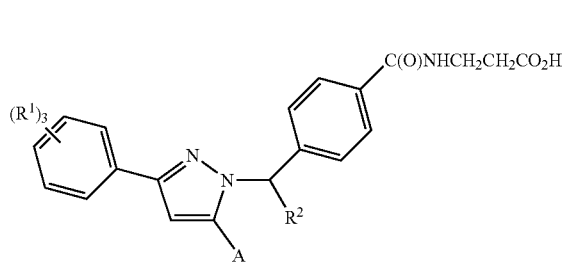

or a pharmaceutically acceptable salt or solvate thereof, wherein:

A represents a 9-10 membered bicyclic heteroaryl group containing 1-4 heteroatoms, 0-4 of which are N and 0-1 of which are O or S,
said bicyclic heteroaryl group being optionally substituted as follows:
a) 1-5 halo groups;
b) 1 $CO_2R^a$; $S(O)_pR^d$; OH, CN, $NO_2$; $C(O)NR^bR^c$ and $NR^bR^c$;
c) 1-2 $C_{1-10}$alkyl or $OC_{1-10}$alkyl, said groups being optionally substituted with:
(1) 1-5 halo groups up to a perhaloalkyl group;
(2) 1 oxo group;
(3) 1-2 OH groups;
(4) 1-2 $C_{1-10}$alkoxy groups, each optionally substituted with:
up to five halo or a perhaloalkoxy, 1 OH or $CO_2R^a$ group;
(5) 1 $CO_2R^a$ or $S(O)_pR^d$;
(6) 1-2 Aryl, Hetcy or HAR groups, each optionally substituted as follows:
(a) 1-5 halo groups,
(b) 1OH, $CO_2R^a$, CN, $S(O)_pR^d$, $NO_2$ or $C(O)NR^bR^c$, and
(c) 1-2 $C_{1-10}$alkyl or alkoxy groups, each optionally substituted with: 1-5 halo, up to perhaloalkyl, and 1-2 OH or $CO_2R^a$ groups; and
d) Aryl, HAR, Hetcy, each optionally substituted as set forth below:
(1) 1-3 $C_{1-10}$alkyl or alkoxy groups optionally substituted as follows: 1-5 halo groups; 1-2 OH groups; $CO_2R^a$; CN; $S(O)_pR^d$; phenyl optionally substituted as follows: (i) 1-5 halo groups, (ii) 1$CO_2R^a$, CN, $S(O)_pR^d$, $NO_2$ or $C(O)NR^bR^c$ group, (iii) 1-2 $C_{1-10}$alkyl or alkoxy groups, each optionally substituted with: 1-5 halo, up to perhaloalkyl, and 1-2 OH or $CO_2R^a$ groups; and said Aryl, HAR, Hetcy group d) being further optionally substituted on carbon by a group selected from the group consisting of;
(2) 1-5 halo groups;
(3) 1-2 OH groups;
(4) 1 $S(O)_pR^d$, $NO_2$ or CN group;

(5) 1-2 $CO_2R^a$; and
(6) —$C(O)NR^bR^c$;

$R^a$ is H or $C_{1-10}$alkyl, optionally substituted with phenyl, OH, $OC_{1-6}$alkyl, $CO_2H$, $CO_2C_{1-6}$alkyl and 1-3 halo groups;

$R^b$ is H or $C_{1-10}$alkyl;

$R^c$ is H or is independently selected from:
   (a) $C_{1-10}$alkyl, optionally substituted with OH, $OC_{1-6}$alkyl, $CO_2H$, $CO_2C_{1-6}$alkyl, and 1-3 halo groups;
   (b) Aryl or Ar—$C_{1-6}$alkyl, each optionally substituted with 1-5 halos and 1-3 members selected from the group consisting of: CN, OH, $C_{1-10}$alkyl and $OC_{1-10}$ alkyl, said alkyl and alkoxy being further optionally substituted with 1-5 halo groups up to perhalo;
   (c) Hetcy or Hetcy-$C_{1-6}$alkyl, optionally substituted with 1-5 halo groups and 1-3 groups selected from: oxo, $C_{1-10}$alkyl and $OC_{1-10}$ alkyl, said alkyl and alkoxy being further optionally substituted with 1-5 halo groups up to perhalo; and
   (d) HAR or HAR-$C_{1-6}$alkyl, optionally substituted with 1-5 halo groups and 1-3 groups selected from: $C_{1-10}$alkyl and $OC_{1-10}$ alkyl, said alkyl and alkoxy being further optionally substituted with 1-5 halo groups up to perhalo;

$R^d$ is $C_{1-10}$alkyl, Aryl or Ar—$C_{1-10}$alkyl; and p is an integer selected from 0, 1 and 2;

each $R^a$ represents H or is selected from the group consisting of:
   a) halo; $CO_2R^a$; $S(O)_pR^d$; OH, CN, $NO_2$; $C(O)NR^bR^c$ and $NR^bR^c$;
   b) $C_{1-10}$alkyl or $OC_{1-10}$alkyl, said groups being optionally substituted with:
      (1) 1-5 halo groups up to a perhaloalkyl group;
      (2) 1 oxo group;
      (3) 1-2 OH groups;
      (4) 1-2 $C_{1-10}$alkoxy groups, each optionally substituted with:
         up to five halo or a perhaloalkoxy, 1 OH or $CO_2R^a$ group;
      (5) 1 $CO_2R^a$ or $S(O)_pR^d$;
      (6) 1-2 Aryl, Hetcy or HAR groups, each optionally substituted as follows:
         (a) 1-5 halo groups,
         (b) 1 OH, $CO_2R^a$, CN, $S(O)_pR^d$, $NO_2$ or $C(O)NR^bR^c$, and
         (c) 1-2 $C_{1-10}$alkyl or alkoxy groups, each optionally substituted with: 1-5 halo, up to perhaloalkyl, and 1-2 OH or $CO_2R^a$ groups;
   c) Aryl, HAR, Hetcy, each optionally substituted as set forth below:
      (1) 1-3 $C_{1-10}$alkyl or alkoxy groups optionally substituted as follows: 1-5 halo groups; 1-2 OH groups; $CO_2R^a$; CN; $S(O)_pR^d$, phenyl optionally substituted as follows: (i) 1-5 halo groups, (ii) 1 $CO_2R^a$, CN, $S(O)_pR^d$, $NO_2$ or $C(O)NR^bR^c$ group, (iii) 1-2 $C_{1-10}$alkyl or alkoxy groups, each optionally substituted with: 1-5 halo, up to perhaloalkyl, and 1-2 OH or $CO_2R^a$ groups; and said Aryl, HAR, Hetcy group c) being further optionally substituted on carbon by a group selected from the group consisting of;
   (2) 1-5 halo groups;
   (3) 1-2 OH groups;
   (4) 1$S(O)_pR^d$, $NO_2$ or CN group;
   (5) 1-2$CO_2R^a$; and
   (6) —$C(O)NR^bR^c$, wherein $R^a$, $R^b$, $R^c$, $R^d$, and p are as previously defined, and $R^2$ is selected from hydrogen and $C_{1-6}$alkyl.

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched, or cyclic, or combinations thereof, containing the indicated number of carbon atoms. If no number is specified, 1-10 carbon atoms are intended for linear and 3-10 carbon atoms for branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-10 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Aryl" (Ar) means mono- and bicyclic aromatic rings containing 6-12 carbon atoms. Examples of aryl include phenyl, naphthyl, indenyl and the like.

"Heteroaryl" (HAR) unless otherwise specified, means a mono- or bicyclic aromatic ring or ring system containing at least one heteroatom selected from O, S and N, with each ring containing 5 to 6 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, quinoxalinyl and the like. Heteroaryl also includes aromatic heterocyclic groups fused to heterocycles that are non-aromatic or partially aromatic, and aromatic heterocyclic groups fused to cycloalkyl rings. Heteroaryl also includes such groups in charged form, e.g., pyridinium.

"Heterocyclyl" (Hetcy) unless otherwise specified, means mono- and bicyclic saturated rings and ring systems containing at least one heteroatom selected from N, S and O, each of said ring having from 3 to 10 atoms in which the point of attachment may be carbon or nitrogen. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils). Heterocyclyl moreover includes such moieties in charged form, e.g., piperidinium.

"Halogen" (Halo) includes fluorine, chlorine, bromine and iodine.

The present invention in its broadest aspect is directed to a compound represented by formula I:

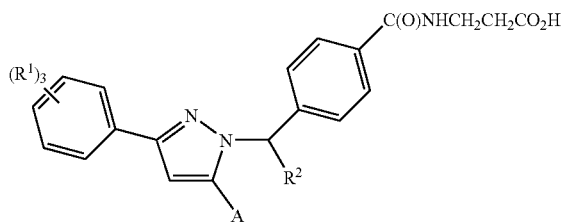

or a pharmaceutically acceptable salt or solvate thereof, wherein:

A represents a 9-10 membered bicyclic heteroaryl group containing 1-4 heteroatoms, 0-4 of which are N and 0-1 of which are O or S,
said bicyclic heteroaryl group being optionally substituted as follows:
c) 1-5 halo groups;
d) $1CO_2R^a$; $S(O)_pR^d$; OH, CN, $NO_2$; $C(O)NR^bR^c$ and $NR^bR^c$;
e) $1\text{-}2C_{1\text{-}10}$alkyl or $OC_{1\text{-}10}$alkyl, said groups being optionally substituted with:
  (1) 1-5 halo groups up to a perhaloalkyl group;
  (2) 1 oxo group;
  (3) 1-2 OH groups;
  (4) 1-2 $C_{1\text{-}10}$alkoxy groups, each optionally substituted with:
    up to five halo or a perhaloalkoxy, 1 OH or $CO_2R^a$ group;
  (5) 1 $CO_2R^a$ or $S(O)_pR^d$;
  (6) 1-2 Aryl, Hetcy or HAR groups, each optionally substituted as follows:
    (a) 1-5 halo groups,
    (b) 1OH, $CO_2R^a$, CN, $S(O)_pR^d$, $NO_2$ or $C(O)NR^bR^c$, and
    (c) 1-2 $C_{1\text{-}10}$alkyl or alkoxy groups, each optionally substituted with: 1-5 halo, up to perhaloalkyl, and 1-2 OH or $CO_2R^a$ groups; and
d) Aryl, HAR, Hetcy, each optionally substituted as set forth below:
  (1) $1\text{-}3C_{1\text{-}10}$alkyl or alkoxy groups optionally substituted as follows: 1-5 halo groups; 1-2OH groups; $CO_2R^a$; CN; $S(O)_pR^d$; phenyl optionally substituted as follows: (i) 1-5 halo groups, (ii) $1CO_2R^a$, CN, $S(O)_pR^d$, $NO_2$ or $C(O)NR^bR^c$ group, (iii) 1-2 $C_{1\text{-}10}$alkyl or alkoxy groups, each optionally substituted with: 1-5 halo, up to perhaloalkyl, and 1-2 OH or $CO_2R^a$ groups; and said Aryl, HAR, Hetcy group d) being further optionally substituted on carbon by a group selected from the group consisting of;
  (2) 1-5 halo groups;
  (3) 1-2OH groups;
  (4) $1S(O)_pR^d$, $NO_2$ or CN group;
  (5) 1-2 $CO_2R^a$; and
  (6) —$C(O)NR^bR^c$;

$R^a$ is H or $C_{1\text{-}10}$alkyl, optionally substituted with phenyl, OH, $OC_{1\text{-}6}$alkyl, $CO_2H$, $CO_2C_{1\text{-}6}$alkyl and 1-3 halo groups;
$R^b$ is H or $C_{1\text{-}10}$alkyl;
$R^c$ is H or is independently selected from:
  (a) $C_{1\text{-}10}$alkyl, optionally substituted with OH, $OC_{1\text{-}6}$alkyl, $CO_2H$, $CO_2C_{1\text{-}6}$alkyl, and 1-3 halo groups;
  (b) Aryl or Ar—$C_{1\text{-}6}$alkyl, each optionally substituted with 1-5 halos and 1-3 members selected from the group consisting of: CN, OH, $C_{1\text{-}10}$alkyl and $OC_{1\text{-}10}$ alkyl, said alkyl and alkoxy being further optionally substituted with 1-5 halo groups up to perhalo;
  (c) Hetcy or Hetcy-$C_{1\text{-}6}$alkyl, optionally substituted with 1-5 halo groups and 1-3 groups selected from: oxo, $C_{1\text{-}10}$alkyl and $OC_{1\text{-}10}$ alkyl, said alkyl and alkoxy being further optionally substituted with 1-5 halo groups up to perhalo; and
  (d) HAR or HAR-$C_{1\text{-}6}$alkyl, optionally substituted with 1-5 halo groups and 1-3 groups selected from: $C_{1\text{-}10}$alkyl and $OC_{1\text{-}10}$ alkyl, said alkyl and alkoxy being further optionally substituted with 1-5 halo groups up to perhalo;

$R^d$ is $C_{1\text{-}10}$alkyl, Aryl or Ar—$C_{1\text{-}10}$alkyl; and
p is an integer selected from 0, 1 and 2;

each $R^a$ represents H or is selected from the group consisting of:
  a) halo; $CO_2R^a$; $S(O)_pR^d$; OH, CN, $NO_2$; $C(O)NR^bR^c$ and $NR^bR^c$;
  b) $C_{1\text{-}10}$alkyl or $OC_{1\text{-}10}$alkyl, said groups being optionally substituted with:
    (1) 1-5 halo groups up to a perhaloalkyl group;
    (2) 1 oxo group;
    (3) 1-2 OH groups;
    (4) 1-2$C_{1\text{-}10}$alkoxy groups, each optionally substituted with:
      up to five halo or a perhaloalkoxy, 1 OH or $CO_2R^a$ group;
    (5) $1CO_2R^a$ or $S(O)_pR^d$;
    (6) 1-2 Aryl, Hetcy or HAR groups, each optionally substituted as follows:
      (a) 1-5 halo groups,
      (b) 1OH, $CO_2R^a$, CN, $S(O)_pR^d$, $NO_2$ or $C(O)NR^bR^c$, and
      (c) 1-2 $C_{1\text{-}10}$alkyl or alkoxy groups, each optionally substituted with: 1-5 halo, up to perhaloalkyl, and 1-2OH or $CO_2R^a$ groups;
  c) Aryl, HAR, Hetcy, each optionally substituted as set forth below:
    (1) $1\text{-}3C_{1\text{-}10}$alkyl or alkoxy groups optionally substituted as follows: 1-5 halo groups; 1-2OH groups; $CO_2R^a$; CN; $S(O)_pR^d$, phenyl optionally substituted as follows: (i) 1-5 halo groups, (ii) $1CO_2R^a$, CN, $S(O)_pR^d$, $NO_2$ or $C(O)NR^bR^c$ group, (iii) 1-2 $C_{1\text{-}10}$alkyl or alkoxy groups, each optionally substituted with: 1-5 halo, up to perhaloalkyl, and 1-2 OH or $CO_2R^a$ groups; and said Aryl, HAR, Hetcy group c) being further optionally substituted on carbon by a group selected from the group consisting of;
  (2) 1-5 halo groups;
  (3) 1-2 OH groups;
  (4) $1 S(O)_pR^d$, $NO_2$ or CN group;
  (5) 1-2 $CO_2R^a$; and
  (6) —$C(O)NR^bR^c$, wherein $R^a$, $R^b$, $R^c$, $R^d$, and p are as previously defined, and $R^2$ is selected from hydrogen and $C_{1\text{-}6}$alkyl.

One aspect of the invention that is of interest relates to compounds of formula I wherein:

A represents a 9-10 membered bicyclic heteroaryl group containing 1-3 heteroatoms, 0-3 of which are N and 0-1 of which are O or S,
said bicyclic heteroaryl group being optionally substituted as follows:
  a) 1-5 halo groups;
  b) 1 $CO_2R^a$; $S(O)_pR^d$; OH, CN;
  c) 1-2 $C_{1\text{-}10}$alkyl or $OC_{1\text{-}10}$alkyl, said groups being optionally substituted with:
    (1) 1-5 halo groups up to a perhaloalkyl group;

(2) 1-2 $C_{1-10}$alkoxy groups, each optionally substituted with:
   up to five halo or a perhalo, 1OH or $CO_2R^a$ group.

Within this aspect of the invention, all other variables are as originally defined.

Another aspect of the invention that is of interest relates to a compound of formula I wherein each $R^1$ represents H or is selected from the group consisting of:
   a) halo; $CO_2R^a$; $S(O)_pR^d$; OH, CN;
   b) $C_{1-10}$alkyl or $OC_{1-10}$alkyl, said groups being optionally substituted with:
      (1) 1-5 halo groups up to a perhaloalkyl group;
      (2) 1 oxo group;
      (3) 1-2 OH groups;
      (4) 1-2 $C_{1-10}$alkoxy groups, each optionally substituted with:
         up to five halo or a perhaloalkoxy, 1OH or $CO_2R^a$ group;
         and
      (5) 1 $CO_2R^a$ or $S(O)_pR^d$.

Within this aspect of the invention, all other variables are as originally defined.

Of more particular interest are compounds of formula I wherein:

A represents a 9-10 membered bicyclic heteroaryl group containing 1-3 heteroatoms, 0-3 of which are N and 0-1 of which are O or S, said bicyclic heteroaryl group being optionally substituted as follows:
   a) 1-5 halo groups;
   b) 1 $CO_2R^a$; $S(O)_pR^d$; OH, CN;
   c) 1-2 $C_{1-10}$alkyl or $OC_{1-10}$alkyl, said groups being optionally substituted with:
      (1) 1-5 halo groups up to a perhaloalkyl group;
      (2) 1-2 $C_{1-10}$alkoxy groups, each optionally substituted with:
         up to five halo or a perhaloalkoxy, 1OH or $CO_2R^a$ group;
         and each $R^1$ represents H or is selected from the group consisting of:
   a) halo; $CO_2R^a$; $S(O)_pR^d$; OH, CN;
   b) $C_{1-10}$alkyl or $OC_{1-10}$alkyl, said groups being optionally substituted with:
      (1) 1-5 halo groups up to a perhaloalkyl group;
      (2) 1 oxo group;
      (3) 1-2 OH groups;
      (4) 1-2 $C_{1-10}$alkoxy groups, each optionally substituted with:
         up to five halo or a perhaloalkoxy, 1OH or $CO_2R^a$ group;
         and
      (5) 1 $CO_2R^a$ or $S(O)_pR^d$.

Within this aspect of the invention, all other variables are as originally defined.

Of more interest are compounds of formula I wherein:

A represents a 9-10 membered bicyclic heteroaryl group selected from the group consisting of: indole, benzimidazole, benzthiazole, benzoxazole, benzofuran, quinoline, isoquinoline and quinoxaline, said group being optionally substituted as follows:

a) 1-5 halo groups;

b) 1OH group;

c) 1-2 $C_{1-10}$ alkyl or $OC_{1-10}$alkyl groups, said groups being optionally substituted with 1-5 halo groups, up to perhaloalkyl;

and each R1 represents H or is selected from the group consisting of:

a) halo;

b) $C_{1-10}$alkyl or $OC_{1-10}$ alkyl, optionally substituted with 1-5 halo groups up to perhaloalkyl; and
   $R_2$ is H or methyl.

Species falling within the scope of the present invention that are of particular interest are contained in the examples provided herein.

The invention further includes a pharmaceutical composition which is comprised of a compound of formula I in combination with a pharmaceutically acceptable carrier.

Also included is a method of treating type 2 diabetes mellitus in a mammalian patient in need of such treatment, comprising administering to said patient a compound of formula I in an amount that is effective to treat type 2 diabetes mellitus.

Also included is a method of preventing or delaying the onset of type 2 diabetes mellitus in a mammalian patient in need thereof, comprising administering to said patient a compound of formula I in an amount that is effective to prevent or delay the onset of type 2 diabetes mellitus.

Also included in the present invention is a method of treating hyperglycemia, diabetes or insulin resistance in a mammalian patient in need of such treatment which comprises administering to said patient an effective amount of a compound of formula I.

Also included in a method of treating, preventing or delaying the onset of diseases or conditions that are associated with type 2 diabetes mellitus. Examples include diseases and conditions selected from the group consisting of: dyslipidemias, (e.g., hyperlipidemia), such as elevated levels of cholesterol (hypercholesterolemia), triglycerides (hypertriglyceridemia) or low density lipoproteins (LDL) (high LDL levels), low levels of high density lipoprotein (HDL), microvascular or macrovascular changes and the sequellae of such conditions, such as coronary heart disease, stroke, peripheral vascular disease, hypertension, renal hypertension, nephropathy, neuropathy and retinopathy. The method entails administering to a type 2 diabetic patient, e.g., a human patient, an amount of a compound of formula I that is effective for treating, preventing or delaying the onset of such diseases or conditions.

Also included in the present invention is a method of treating atherosclerosis in a mammalian patient in need of such treatment, comprising administering to said patient a compound of formula I in an amount effective to treat atherosclerosis.

Also included in the present invention is a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequalae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient a compound in accordance with formula I in an amount that is effective to treat said condition.

Also included in the present invention is a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I in an amount that is effective to delay the onset of said condition.

Also included in the present invention is a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I in an amount that is effective to reduce the risk of developing said condition.

More particularly, the present invention includes a method of treating, reducing the risk of developing, or delaying the onset of obesity in a mammalian patient in need of such treatment, comprising administering to the patient an amount of a compound of formula I that is effective for treating, preventing or delaying the onset of obesity.

Also more particularly, the present invention includes a method of treating, reducing the risk of developing, or delaying the onset of Syndrome X in a mammalian patient in need of such treatment, comprising administering to the patient an amount of a compound of formula I that is effective for treating, preventing or delaying the onset of Syndrome X.

Optical Isomers-Diastereomers-Geometric Isomers-Tautomers

Many of the compounds of formula I contain one or more asymmetric centers and thus occur as racemates and racemic mixtures, single enantiomers, diastereomeric mixtures and individual diastereomers. The present invention includes all such isomeric forms of the compounds, in pure form as well as in mixtures.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Salts and Solvates

The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Solvates as used herein refers to the compound of formula I or a salt thereof, in association with a solvent, such as water. Representative examples include hydrates, hemihydrates, trihydrates and the like.

References to the compounds of Formula I include the pharmaceutically acceptable salts and solvates.

This invention relates to method of antagonizing or inhibiting the production or activity of glucagon, thereby reducing the rate of gluconeogenesis and glycogenolysis, and the concentration of glucose in plasma.

The compounds of formula I can be used in the manufacture of a medicament for the prophylactic or therapeutic treatment of disease states in mammals caused by elevated levels of glucose, comprised of combining the compound of formula I with the carrier materials to provide the medicament.

Dose Ranges

The prophylactic or therapeutic dose of a compound of formula I will, of course, vary with the nature of the condition to be treated, the particular compound selected and its route of administration. It will also vary according to the age, weight and response of the individual patient. In general, the daily dose range lie within the range of from about 0.001 mg to about 100 mg per kg body weight, preferably about 0.01 mg to about 50 mg per kg, and more preferably 0.1 to 10 mg per kg, in single or divided doses. It may be necessary to use dosages outside of these limits in some cases. The terms "effective amount" "anti-diabetic effective amount" and the other terms appearing throughout the application addressing the amount of the compound to be used refer to the dosage ranges provided, taking into account any necessary variation outside of these ranges, as determined by the skilled physician. Similarly, when a compound is "administered" to the patient, this means that the compound is delivered as a conventional pharmaceutical preparation, or delivered systemically to the patient, such as via the administration of a prodrug.

Representative dosages for adults thus range from about 0.1 mg to about 1.0 g per day, preferably about 1 mg to about 200 mg, in single or divided doses.

When intravenous or oral administration is employed, a representative dosage range is from about 0.001 mg to about 100 mg (preferably from 0.01 mg to about 10 mg) of a compound of Formula I per kg of body weight per day, and more preferably, about 0.1 mg to about 10 mg of a compound of Formula I per kg of body weight per day.

Pharmaceutical Compositions

As mentioned above, the pharmaceutical composition comprises a compound of Formula I or a pharmaceutically acceptable salt or solvate thereof and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human with an effective dosage of a compound of the present invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred. Thus, one aspect of the invention that is of interest is the use of a compound of formula I for preparing a pharmaceutical composition which is comprised of combining the compound of formula I with the carrier.

In preparing oral compositions, any of the usual pharmaceutical media may be employed, such as, for example, water, glycols, oils, alcohols, flavoring agents, preservatives, coloring agents and the like in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets, with the solid oral preparations being preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 1 g of the active ingredient and each cachet or capsule contains from about 1 to about 500 mg of the active ingredient.

The following are examples of pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to make | 1.0 mL |

| Capsule | mg/capsule |
|---|---|
| Compound of Formula I | 25 |
| Lactose Powder | 573.5 |
| Magnesium Stearate | 1.5 |
| Total | 600 mg |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| Total | 500 mg |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Combination Therapy

Compounds of Formula I may be used in combination with other drugs that are used in the treatment/prevention/delaying the onset of type 2 diabetes mellitus, as well as the diseases and conditions associated with type 2 diabetes mellitus, for which compounds of Formula I are useful. Other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical composition, include, but are not limited to: (a) biguanides (e.g., buformin, metformin, phenformin), (b) PPAR agonists (e.g., troglitazone, pioglitazone, rosiglitazone), (c) insulin, (d) somatostatin, (e) α-glucosidase inhibitors (e.g., voglibose, miglitol, acarbose), (f) DPP-IV inhibitors, (g) LXR modulators and (h) insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide).

The weight ratio of the compound of the Formula I to the second active ingredient may be varied within wide limits and depends upon the effective dose of each ingredient. Generally, an effective dose of each will be used. Thus, for example, when a compound of the Formula I is combined with a PPAR agonist the weight ratio of the compound of the Formula I to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

For combination products, the compound of formula I may be combined with any other active ingredients and then added to the carrier ingredients; alternatively the order of mixing may be varied.

Examples of pharmaceutical combination compositions include:

(1) a compound according to formula I, (2) a compound selected from the group consisting of: (a) DPP-IV inhibitors; (b) insulin sensitizers selected from the group consisting of (i) PPAR agonists and (ii) biguanides; (c) insulin and insulin mimetics; (d) sulfonylureas and other insulin secretagogues; (e) α-glucosidase inhibitors; (f) glucagon receptor antagonists; (g) GLP-1, GLP-1 mimetics, and GLP-1 receptor agonists; (h) GIP, GIP mimetics, and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid or a salt thereof, (iv) PPARα agonists, (v) PPARα/γ dual agonists, (vi) inhibitors of cholesterol absorption, (vii) acyl CoA:cholesterol acyltransferase inhibitors, (viii) anti-oxidants and (ix) LXR modulators; (k) PPARδ agonists; (l) antiobesity compounds; (m) an ileal bile acid transporter inhibitor; (n) anti-inflammatory agents other than glucocorticoids; and (o) protein tyrosine phosphatase-1B (PTP-1B) inhibitors; and (3) a pharmaceutically acceptable carrier.

In accordance with the methods described herein one method that is of interest relates to a method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient an effective amount of a compound of formula I and a compound selected from the group consisting of: (a) DPP-IV inhibitors; (b) insulin sensitizers selected from the group consisting of (i) PPAR agonists and (ii) biguanides; (c) insulin and insulin mimetics; (d) sulfonylureas and other insulin secretagogues; (e) α-glucosidase inhibitors; (f) glucagon receptor antagonists; (g) GLP-1, GLP-1 mimetics, and GLP-1 receptor agonists; (h) GIP, GIP mimetics, and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid and salts thereof, (iv) PPARα agonists, (v) PPARα/γ dual agonists, (vi) inhibitors of cholesterol absorption, (vii) acyl CoA:cholesterol acyltransferase inhibitors, (viii) anti-oxidants and (ix) LXR modulators; (k) PPARδ agonists; (l) antiobesity compounds; (m) an ileal bile acid transporter inhibitor (n) anti-inflammatory agents excluding glucocorticoids; and (o) protein tyrosine phosphatase-1B (PTP-1B) inhibitors, said compounds being administered to the patient in an amount that is effective to treat said condition.

More particularly, a method that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient a therapeutically effective amount of a compound of formula I and an HMG-CoA reductase inhibitor.

Even more particularly, the method that is of interest comprises administering to the patient a therapeutically effective amount of a compound of formula I and an HMG-CoA reductase inhibitor wherein the HMG-CoA reductase inhibitor is a statin, and even more particularly, the statin is selected from the group consisting of lovastatin, simvastatin, pravastatin, fluvastatin, atorvastatin, itavastatin, ZD4522 and rivastatin.

A different aspect of the invention relates to a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment a therapeutically effective amount of a compound of formula I and an HMG-CoA reductase inhibitor.

More particularly, another aspect of the invention relates to a method for delaying the onset or reducing the risk of developing atherosclerosis in a human patient in need of such treatment comprising administering to said patient an effective amount of a compound of formula I and an HMG-CoA reductase inhibitor. Even more particularly, the method comprises administering an effective amount of a compound of formula I and an HMG-CoA reductase inhibitor wherein the HMG-CoA reductase inhibitor is a statin. Even more particularly, the method comprises administering a compound of formula I and a statin selected from the group consisting of: lovastatin, simvastatin, pravastatin, fluvastatin, atorvastatin, itavastatin, ZD-4522 and rivastatin. Still more particularly, the method comprises administering a compound of formula I and the statin known as simvastatin.

Another aspect of the invention relates to a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment a therapeutically effective amount of a compound of formula I and a cholesterol absorption inhibitor. In particular, the method comprises administering an effective amount of a compound of formula I and the cholesterol absorption inhibitor known as ezetimibe.

More particularly, a method for delaying the onset or reducing the risk of developing atherosclerosis in a human patient in need of such treatment is described which comprises administering to said patient an effective amount of a compound of formula I and a cholesterol absorption inhibitor. More particularly, the method comprises administering a compound of formula I and the cholesterol absorption inhibitor known as ezetimibe.

Throughout the instant application, the following abbreviations are used with the following meanings unless otherwise indicated:

| | |
|---|---|
| Bu = butyl, t-Bu = t-butyl | Bn and Bnzl = benzyl |
| BOC, Boc = t-butyloxycarbonyl | CBZ, Cbz = Benzyloxycarbonyl |
| DCC = Dicyclohexylcarbodiimide | DCM = dichloromethane |
| DIEA = diisopropylethylamine | DMF = N,N-dimethylformamide |
| DMAP = 4-Dimethylaminopyridine | Et = ethyl |
| EtOAc = ethyl acetate | EtOH = ethanol |
| eq. = equivalent(s) | FAB-mass spectrum = Fast atom bombardment-mass spectroscopy |
| HOAc = acetic acid | |
| HOBT, HOBt = Hydroxybenztriazole | HPLC = High pressure liquid chromatography |
| Me = methyl | |
| Ph = phenyl | LAH = Lithium aluminum hydride |
| THF = Tetrahydrofuran | PBS = phosphate buffer saline |
| $C_6H_{11}$ = cyclohexyl | TFA = Trifluoroacetic acid |
| iPr = isopropyl | TMS = Trimethylsilane |
| 2,4-diClPh = 2,4-dichlorophenyl | $Nme_2$ = dimethylamino |
| Py, Pyr = pyridyl | 2ClPh = 2-chlorophenyl |

Compounds of the present invention may be prepared according to the methodology outlined in the following general synthetic schemes.

In one embodiment of the present invention, the compounds of formula I may be prepared from intermediate II (vide infra),

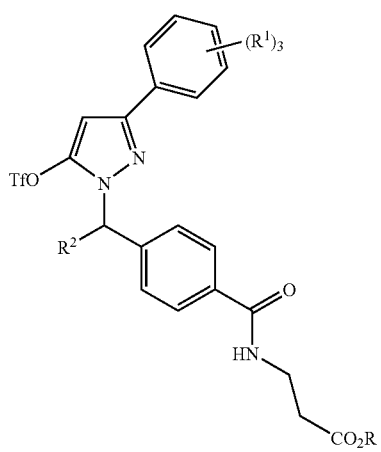

where $R^1$ and $R^2$ are as defined above and R represents a $C_{1-6}$alkyl group.

Compounds II, can in turn be prepared by condensation of the β-ketoester 1 and benzyl hydrazine 2. Compounds such as 1 are commercially available, known in the literature or may be conveniently prepared by a variety of methods familiar to those skilled in the art. One route is illustrated in Scheme 1 and described in Clay et al., *Synthesis*, 1993, 290. Acid chloride 3, which may be commercially available or readily prepared from the corresponding carboxylic acid by treatment with thionyl chloride at elevated temperatures or oxalyl chloride in a solvent such as methylene chloride in the presence of a catalytic amount of dimethylformamide (DMF) at room temperature, is treated with potassium ethyl malonate and magnesium chloride in the presence a base such as triethylamine in an aprotic solvent such as ethyl acetate for 1-16 h to give ketoester 1.

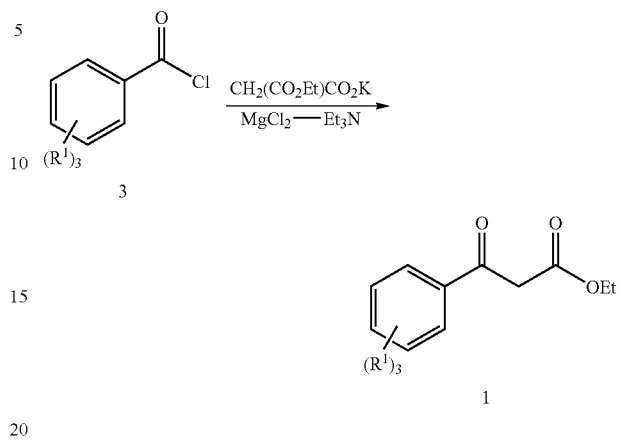

Benzyl hydrazine 2 may be prepared from the corresponding carbonyl analog by condensation with tert-butylcarbazate in the presence of acetic acid in a nonpolar solvent such as toluene at elevated temperatures for 16 to 24 h, Scheme 2. The intermediate 4 is then reduced with a hydride reducing agent such as sodium cyanoborohydride and 1 equivalent of p-toluenesulfonic acid, which should be added in a dropwise fashion. The reaction is carried out in a polar aprotic solvent such as tetrahydrofuran (THF) for 1648 h at ambient temperature. Alternatively, the reaction can be carried out in the absence of p-toluenesulphonic acid if acetic acid is used as a solvent. Following aqueous work-up, the borane complex can be decomposed by slowly adding an aqueous solution of sodium hydroxide or other strong base to give carbamate 5 (see Calabretta et al., *Synthesis*, 1991, 536). Deprotection of the BOC group was effected by treatment with an acid such as trifluoroacetic acid in methylene chloride at ambient temperature for 0.25-2 h. The reaction can be performed with or without the addition of triisopropylsilane. The hydrazine 2 can either be used as its trifluoroacetate salt directly from the deprotection, or the free-base can be prepared and the material isolated as the hydrochloride salt by addition of aqueous hydrochloric acid and evaporation of the solvent. In the case ($R^2$ not H) that intermediate 5 contains a chiral center, the enantiomers can be resolved at this point by chromatography using a homochiral stationary phase. Alternatively, hydrazone 4 can be directly reduced with hydrogen and a chiral catalyst such as a rhodium DuPHOS complex as described in Burk et al., *Tetrahedron*, 1994, 50, 4399. The solvent used for the reaction was generally an alcohol such as 2-propanol and elevated hydrogen pressure was used. This reaction would give material of enriched enantioselectivity which could be further purified by chiral chromatography as described above.

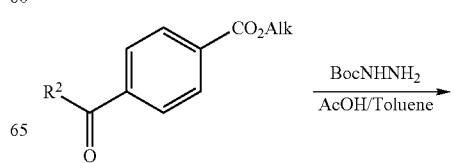

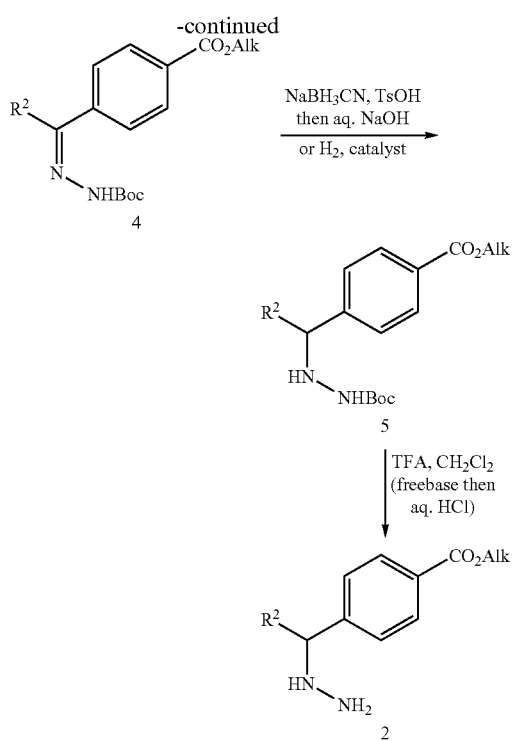

Condensation of the β-ketoester 1 and benzyl hydrazine 2 described in Scheme 3 is carried out by heating the two components in a solvent such as acetic acid or acetonitrile for 1-8 h to give the pyrazolone 6. Elaboration at this point to β-alanine ester 7 can be achieved by saponification of the ester 6 using a base such as aqueous lithium or sodium hydroxide in a polar solvent such as tetrahydrofuran, dioxane, methanol, ethanol or a mixture of similar solvents. Coupling of the beta alanine ester 8 is then achieved using 1-ethyl-3-(3-dimethylaminopropyl)-carbodiimide (EDC) and 1-hydroxybenzotriazole (HOBt) or benzotriazole-1-yloxytrispyrrolidinophosphonium hexafluorophosphate (PyBOP) and a base, generally diisopropylethylamine, in a solvent such as N,N-dimethylformamide (DMF) or methylene chloride for 3 to 48 hours at ambient temperature to yield the compound 7. Pyrazolone 7 is then treated with triflic anhydride in a polar aprotic solvent such as THF in the presence of a base such as triethylamine at −78° C. to room temperature to afford the intermediate II. The product is purified from unwanted side products by recrystallization, trituration, preparative thin layer chromatography, flash chromatography on silica gel as described by W. C. Still et al, *J. Org. Chem.*, 43, 2923, (1978), or HPLC. Purification of intermediates is achieved in the same manner. If the intermediate II is racemic (ie $R^2$ is not hydrogen), then this compound can be resolved via chiral hplc using either normal phase or supercritical fluid conditions.

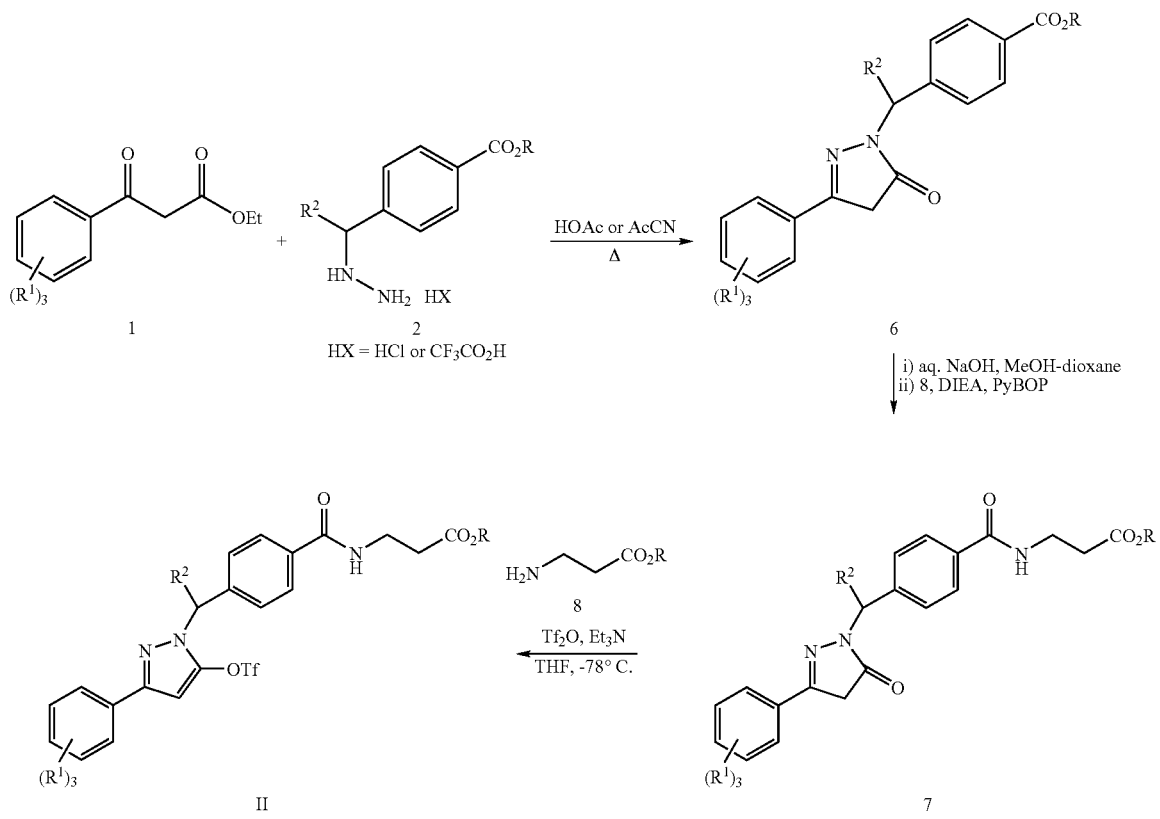

Final products can then be prepared by the coupling of intermediate II with an appropriate heteroaryl boronic acid 9, Scheme 4. In some cases these compounds are commercially available, in others they can be prepared from bromide 10 by treatment with bis(pinacolato)diboron, potassium acetate and a palladium catalyst such as palladium II chloride and a ligand such as diphenyl phosphino ferrocene (dppf). The reaction is heated in a polar aprotic solvent such as DMSO for 1-5 h, followed by cleavage of the boronate ester by treatment with dilute acid such as hydrochloric acid in a solvent such as acetone for a prolonged time. An alternative route to the boronic acid involves treatment of the heteroaryl halide 10 with a strong base such as butyl lithium in a polar aprotic solvent such as THF at low temperatures followed by addition of a trialkyl borate such as trimethyl borate. The reaction is stirred a further 1-5 h with warming to ambient temperature, followed by quenching with dilute acid such as dilute hydrochloric acid prior to isolation of the intermediate 9. When the heteroaryl group is a 2 substituted indole, the lithiation can be accomplished, after protection of the indole nitrogen, directly on the aromatic ring using an amide base such as lithium diisopropylamide in a polar aprotic solvent such as THF at low temperatures followed by addition of a trialkyl borate such as trimethyl or triisopropylborate. The reaction is stirred a further 1-5 h with warming to ambient temperature, followed by quenching with dilute acid such as dilute hydrochloric acid prior to isolation of the intermediate 9a.

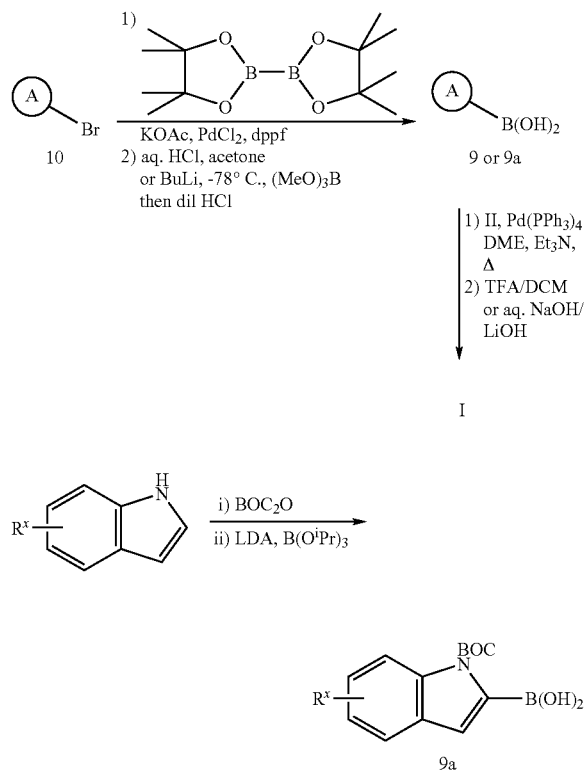

The aryl triflate II can be coupled with boronic acid 9 or 9a using a palladium catalyst such as palladium 2-(di-$^t$butylphosphino)biphenyl or triphenylphosphine. The solvent is generally either dimethoxyethane, ethanol or toluene, and triethylamine, cesium or sodium carbonate or potassium fluoride is also added to the reaction, which may also contain water and is performed at elevated temperatures and may be carried out in a microwave reactor (see Wang et al., *Tet. Lett.*, 2000, 41, 4713 for related cross-coupling reactions). Removal of the ester when R=Me or Et is accomplished by saponification using a base such as aqueous lithium or sodium hydroxide in a polar solvent such as tetrahydrofuran, methanol, ethanol or a mixture of similar solvents. When R is a tert-butyl ester it is most conveniently removed by treatment with trifluoroacetic acid in methylene chloride for 0.5-3 h at ambient temperature. The product is purified from unwanted side products by recrystallization, trituration, preparative thin layer chromatography, flash chromatography on silica gel as described by W. C. Still et al, *J. Org. Chem.*, 43, 2923, (1978), or HPLC. Purification of intermediates is achieved in the same manner. In some cases, the product from the reactions described in Scheme 4 will be further modified. These manipulations may include, but are not limited to substitution, reduction, oxidation, alkylation, acylation, and hydrolysis reactions, which are commonly known to those skilled in the art.

Alternatively, modification of pyrazolone 6 can be carried out in a different order, Scheme 5. Pyrazolone 6 is treated with triflic anhydride in a polar aprotic solvent such as THF in the presence of a base such as triethylamine at −78° C. to room temperature to afford the intermediate 11. Palladium catalyzed coupling with an appropriate heteroaryl boronic acid 9 can be carried out at this point using a method analogous to that described above. Final elaboration can be achieved by saponification of the ester 12 using a base such as aqueous lithium or sodium hydroxide in a polar solvent such as tetrahydrofuran, dioxane, methanol, ethanol or a mixture of similar solvents. Coupling of the beta alanine 8 is then achieved using 1-ethyl-3-(3-dimethylaminopropyl)-carbodiimide (EDC) and 1-hydroxybenzotriazole (HOBt) or benzotriazole-1-yloxytrispyrrolidinophosphonium hexafluorophosphate (PyBOP) and a base, generally diisopropylethylamine, in a solvent such as N,N-dimethylformamide (DMF) or methylene chloride for 3 to 48 hours at ambient temperature to yield the ester of final product I. Removal of the ester when R=Me or Et is accomplished by saponification using a base such as aqueous lithium or sodium hydroxide in a polar solvent such as tetrahydrofuran, dioxane, methanol, ethanol or a mixture of similar solvents. When R is a tert-butyl ester it is most conveniently removed by treatment with trifluoroacetic acid in methylene chloride for 0.5-3 h at ambient temperature. The product is purified from unwanted side products by recrystallization, trituration, preparative thin layer chromatography, flash chromatography on silica gel as described by W. C. Still et al, *J. Org. Chem.*, 43, 2923, (1978), or HPLC. Purification of intermediates is achieved in the same manner. If compound I is racemic (ie $R^2$ is not hydrogen), then this compound can be resolved via chiral hplc using either normal phase or supercritical fluid conditions.

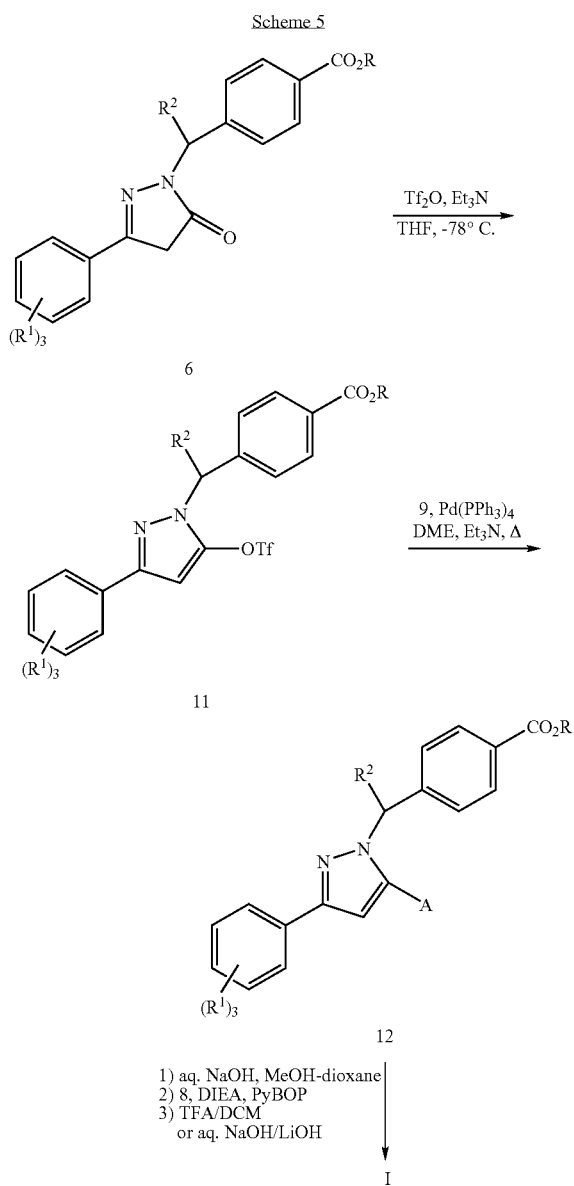

Scheme 5

1) aq. NaOH, MeOH-dioxane
2) 8, DIEA, PyBOP
3) TFA/DCM
   or aq. NaOH/LiOH

In some cases, the product I or the penultimate ester from the reactions described in the schemes above will be further modified. These manipulations may include, but are not limited to substitution, reduction, oxidation, alkylation, acylation, and hydrolysis reactions, which are commonly known to those skilled in the art. One such modification, illustrated here when $R^1$ is a protected phenol as in 13 (R is not hydrogen), involves release of the alcohol and subsequent etherification, Scheme 6. The hydroxyl group may be protected as a silyl ether, in which case a fluoride source, generally hydrofluoric acid or tetrabutylammonium fluoride is used for the reaction. Deprotection of a methoxy ether is routinely effected by treatment of the compound with boron tribromide in a solvent such as methylene chloride for a period of 1-16 h at ambient temperatures. Finally, if the alcohol is protected as an allyl ether, this is removed by treatment with dimethylbarbituric acid and a palladium catalyst, routinely tris(dibenzylideneacetone)dipalladium(0), with a ligand such as 1,4-bis-(diphenylphospino)butane in an aprotic solvent such as methylene chloride for 15 min to 2 h. See "Protective Groups in Organic Synthesis", Greene, published by Wiley and Sons.

Scheme 6

The free hydroxyl group may then be further modified to prepare ethers using an alcohol and coupling agent, such as diisopropylazodicarboxylate, and triphenylphosphine in a non polar solvent such as methylene chloride at temperatures of 0 to 40° C. for 1 to 16 h, Scheme 6. Intermediate 14 can then be converted to the desired products as previously described, vide supra.

An alternative approach to synthesizing the compounds of formula I involves alkylation of pyrazole III (vide infra),

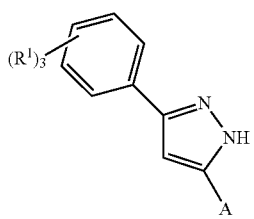

III where $R^1$ and A are as defined above.

Compounds III are known in the literature or may be conveniently prepared by a variety of methods familiar to those skilled in the art as described in Katritsky et al., Advances in Heterocyclic Chemistry, Vol. 6, pg 347-429. One route is illustrated in Scheme 7. Ester 15, which may be commercially available or readily prepared from the corresponding carboxylic acid by esterification using, for example, methanol or ethanol containing an acid such as sulphuric acid, is condensed with the anion of methyl ketone 16 to give diketone 17. The reaction is carried out using a base such as sodium hydride in a polar aprotic solvent such as tetrahydrofuran (THF) at 0 to 25° C. for 16 to 24 h, see March, Advanced Organic Chemistry, 3$^{rd}$ Ed., pg 439 and ref. therein. Compounds such as 16 are commercially available or can be prepared by a variety of methods familiar to those skilled in the art. Diketone 17 is then condensed with hydrazine in a polar solvent such as methanol which may contain an acid such as acetic or hydrochloric acid, for 16 to 24 h at a temperature of 0 to 25° C.

Other routes to ester 15 by a variety of methods known to those skilled in the art can be envisaged. One such method when the heteroaryl group is a 3-substituted quinoline is described in Scheme 8. An appropriately substituted aniline is treated with the diester of ethoxymethylene malonate (Reigel, B.; Lappin, B. H.; Adelson, B. H.; Jackson, R. I.; Albisetti, C. J.; Dodson, R. M.; Baker, R. H. JACS vol 68 p 1264 1946) at elevated temperatures in a solvent such as toluene. Further heating (>200° C.) leads to formation of 4-hydroxyquinoline 18. Treatment of this with a chlorinating agent such as phosphorus oxychloride at elevated temperatures gives the chloro analogue, which can then be reduced with hydrogen gas and a palladium catalyst such as palladium on carbon in an alcoholic solvent such as ethanol or ethanol/ethyl acetate mixtures. Saponification yields the acid if needed. If the heteroaryl group is a 2-substituted quinoline, an appropriately substituted aniline is treated with the diester of acetylenedicarboxylic acid (Edmont D., Rocher, R.; Plisson, C.; and Chenault, J. Bioorganic & Medicinal Chemistry Letters vol 10 p 1831-1834, 2000) at elevated temperatures in a solvent such as methanol followed by further heating at >200° C. to give the hydroxy intermediate 19. This is then converted to the ester 15b as described for the 3-substituted compounds, Scheme 8.

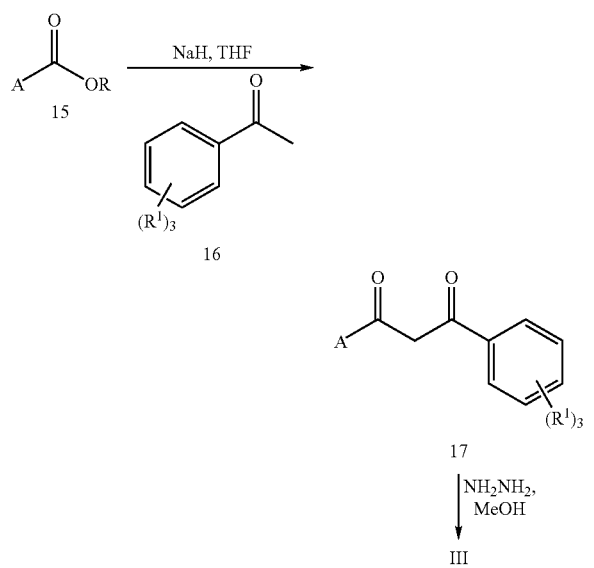

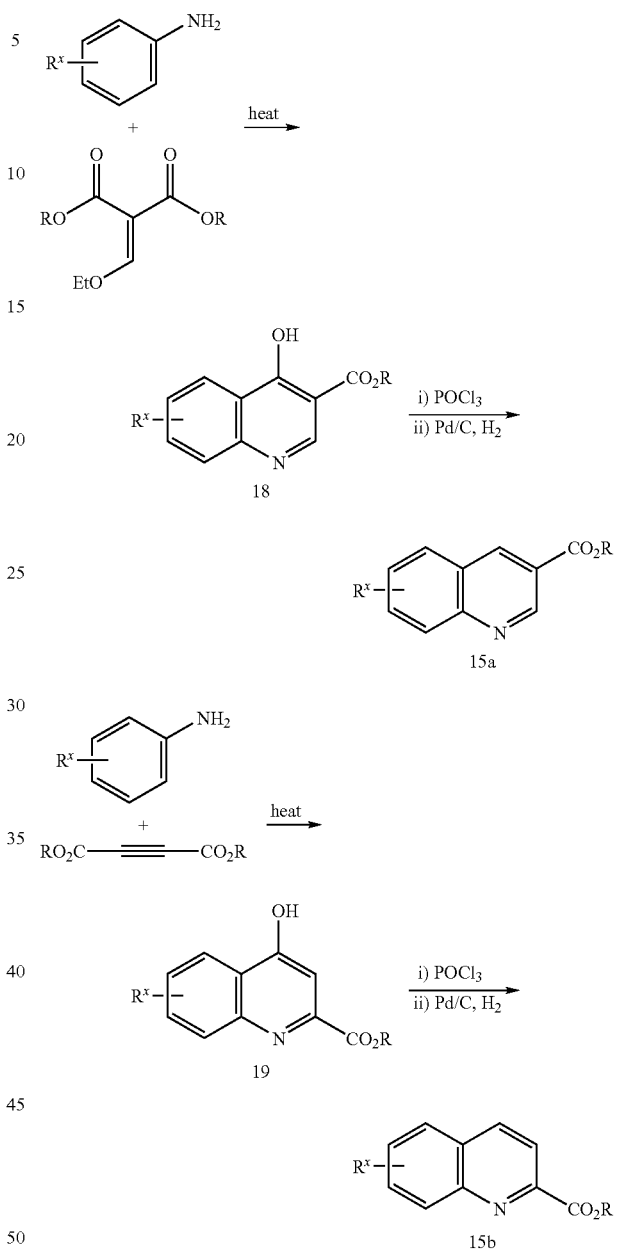

An alternate route to intermediate III involves condensation of alkynyl ketone 20 with hydrazine as shown in Scheme 9 and described in Cabarrocas et. al., Tetrahedron Asymmetry, Vol. 11, pg 2483-2493, 2000 and references therein. This is generally carried out in a polar solvent such as DMF at temperatures of 0-25° C. for 16-24 h. Preparation of the intermediates 20 involves coupling of the alkyne 21 with the Weinreb amide of an appropriately functionalised carboxylic acid using a hindered base such as lithium diisopropylamide or butyl lithium in a polar aprotic solvent such as THF at −78° C. This reaction is described in detail in Tetrahedron Lett., Vol. 22, pg 3815, 1981. Alkynes 21 are either commercially available, or prepared from the corresponding halide and alkynyl magnesium iodide, see Negishi et. al., J. Org. Chem., Vol. 62, pg 8957-8960, 1997 and Org. Lett. Vol. 3, pg 3111-3113, 2001.

Scheme 9

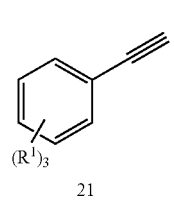 

21

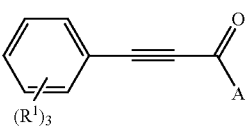

20

15 →

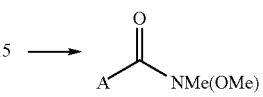

Intermediate III can then be converted via 12 to a compound of formula I as shown in Scheme 10. Alkylation of pyrazole III with a 4-carboalkoxy benzylbromide can be achieved following deprotonation of the pyrazole with a base such as sodium hydride or cesium carbonate in a polar solvent, generally dimethyl formamide (DMF), at 0 to 25° C. for 3 to 24 h. In some cases mixtures of isomers will be formed. These are generally separable by recrystallization, trituration, preparative thin layer chromatography, flash chromatography on silica gel as described by W. C. Still et al, *J. Org. Chem.*, 43, 2923, (1978), or HPLC. Compounds purified by HPLC may be isolated as the corresponding salt. Conversion to final compounds is then achieved as described previously for ester 12. In some cases, the product from the reactions described in Scheme 10 will be further modified. These manipulations may include, but are not limited to substitution, reduction, oxidation, alkylation, acylation, and hydrolysis reactions, which are commonly known to those skilled in the art.

Scheme 10

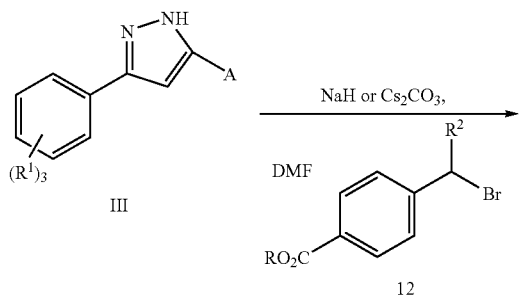

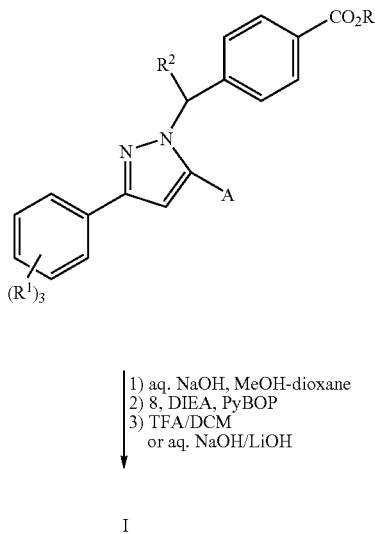

1) aq. NaOH, MeOH-dioxane
2) 8, DIEA, PyBOP
3) TFA/DCM
   or aq. NaOH/LiOH

I

In a further embodiment of the present invention, the compounds may be prepared from intermediate IV (vide infra),

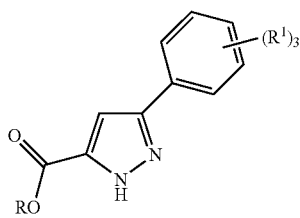

IV where $R^1$ is as defined above and R represents an alkyl group. Compounds IV, are known in the literature or may be conveniently prepared by a variety of methods familiar to those skilled in the art such as described in Katritsky et al., Advances in Heterocyclic Chemistry, Vol. 6, pg 347-429. One route is illustrated in Scheme 11. A diester of oxalic acid 22, which may be commercially available or readily prepared from the corresponding carboxylic acid by esterification using, for example, methanol or ethanol containing an acid such as sulphuric acid, is condensed with the anion of methyl ketone 23 to give diketoester 24, J. Heterocyclic Chem, 26, 1389 (1989). The reaction is carried out using a base such as lithium hexamethyldisilazide in a polar aprotic solvent such as tetrahydrofuran (THF) at −78° C. to 0° C. for 2 to 24 h, see March, Advanced Organic Chemistry, 3$^{rd}$ Ed., pg 439 and ref. therein. Compounds such as 23 are commercially available or can be prepared by a variety of methods familiar to those skilled in the art. Diketone 24 is then condensed with hydrazine in a polar solvent such as ethanol which may contain an acid such as acetic or hydrochloric acid, for 16 to 24 h at a temperature of 0 to 25° C.

Scheme 11

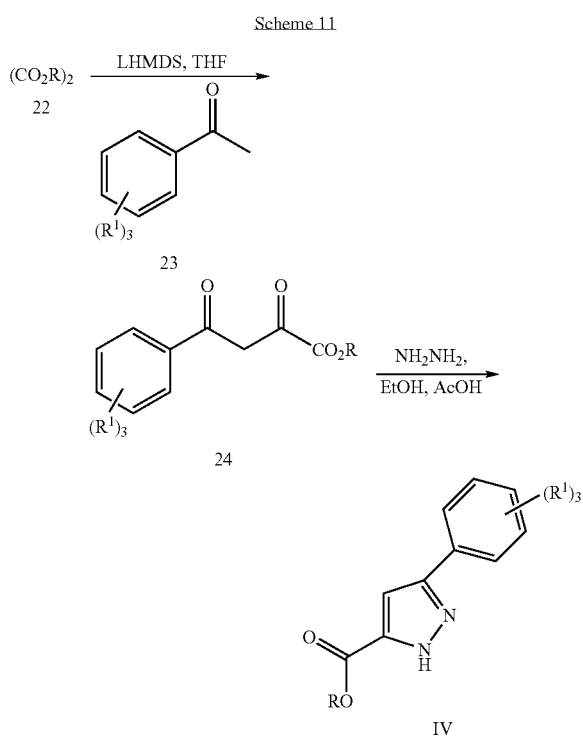

An alternate route to intermediate IV involves condensation of alkynyl ketone 25 with hydrazine as shown in Scheme 12 and described in Cabarrocas et. al., Tetrahedron Asymmetry, Vol. 11, pg 2483-2493, 2000 and references therein. This is generally carried out in a polar solvent such as DMF at temperatures of from about 0 to 25° C. for about 16 to 24 h. Preparation of the intermediate 25 involves coupling of the commercially available alkyne 26 with the Weinreb amide of an appropriately functionalised carboxylic acid using a hindered base such as lithium diisopropylamide or butyl lithium in a polar aprotic solvent such as THF at about −78° C. This reaction is described in detail in Tetrahedron Lett., Vol. 22, pg 3815, 1981.

Scheme 12

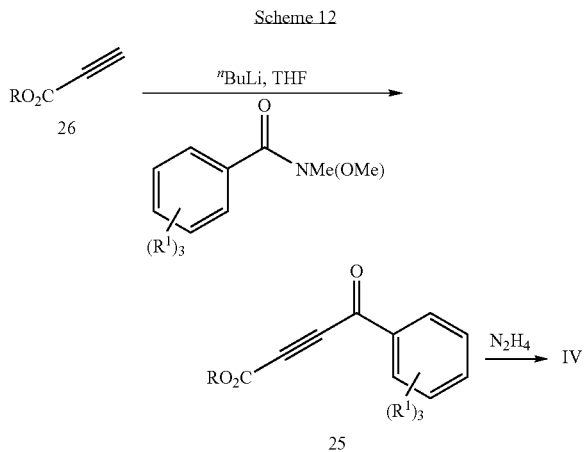

Intermediate IV can then be converted to compounds of formula Ic as shown below in Scheme 13. Alkylation of pyrazole IV with, for example, 4-carbomethoxy benzylbromide can be achieved following deprotonation of the pyrazole with a base such as sodium hydride or cesium carbonate in a polar solvent, generally dimethyl formamide (DMF), at about 0 to 25° C. for about 3 to 24 h. Alternatively, pyrazole IV can be alkylated using Mitsonobu conditions with a benzylic alcohol 27 which is prepared from reduction of a carbonyl derivative. In most cases the alkylation gives predominantly compound 28, however in some cases mixtures of isomers will be formed. These are generally separable by recrystallization, trituration, preparative thin layer chromatography, or flash chromatography on silica gel as described by W. C. Still et al, *J. Org. Chem.*, 43, 2923, (1978), or HPLC. Compounds purified by HPLC may be isolated as the corresponding salt.

Release of the pyrazole carboxylic acid 30 can be achieved selectively in the presence of the benzyl ester if the former is orthogonally protected ie R=$^t$Bu. This is achieved most conveniently by treatment with trifluoroacetic acid in methylene chloride for 0.5-3 h at ambient temperature. Coupling of the acid with an aromatic ortho substituted amine 29 is carried out with standard peptide coupling conditions, for example using 1-ethyl-3-(3-dimethylaminopropyl)-carbodiimide (EDC), 1-hydroxy-7-azabenzotriazole (HOAt), and a base, generally diisopropylethylamine, in a solvent such as N,N-dimethylformamide (DMF) or methylene chloride for 3 to 48 hours at ambient temperature to yield amide 31. If amine 29 was a diamine, intermediate 31 can be cyclized to a benzimidazole, by refluxing in a polar protic solvent such as acetic acid for 30 min to 6 h. In some cases mixtures of isomers were formed. To prepare a benzthiazole, 2-aminothiophenol was used, and following amide coupling the thiazole ring was formed by dropping the reaction mixture into acetic acid which may contain dithiothreitol. Heating was continued for a further 30 min to 6 h. Similarly if a 2-aminophenol was used cyclization resulted in formation of a benzoxazole. Saponification of the methyl ester of 31 is then achieved using a base such as aqueous lithium or sodium hydroxide in a polar solvent such as tetrahydrofuran, methanol, ethanol or a mixture of similar solvents. Coupling of the acid with beta alanine 8 is then achieved using 1-ethyl-3-(3-dimethylaminopropyl)-carbodiimide (EDC), 1-hydroxybenzotriazole (HOBt), and a base, generally diisopropylethylamine, in a solvent such as N,N-dimethylformamide (DMF) or methylene chloride for 3 to 48 hours at ambient temperature to yield after deprotection the compounds Ic.

The product is purified from unwanted side products by recrystallization, trituration, preparative thin layer chromatography, flash chromatography on silica gel as described by W. C. Still et al, *J. Org. Chem.*, 43, 2923, (1978), or HPLC. Purification of intermediates is achieved in the same manner. As will be understood by those skilled in the art, for the preparation of enantiomerically pure compounds, enantiomerically pure starting materials should be used.

In some cases, the product from the reactions described in Scheme 13 will be further modified. These manipulations may include, but are not limited to substitution, reduction, oxidation, alkylation, acylation, and hydrolysis reactions, which are commonly known to those skilled in the art. One such modification is saponification of a methyl or removal of a tert butyl ester, as shown, this is achieved using a base such as aqueous lithium or sodium hydroxide in a polar solvent such as tetrahydrofuran, methanol, ethanol or a mixture of similar solvents or by treatment with trifluoroacetic acid in methylene chloride at ambient temperatures for 0.5-3 h.

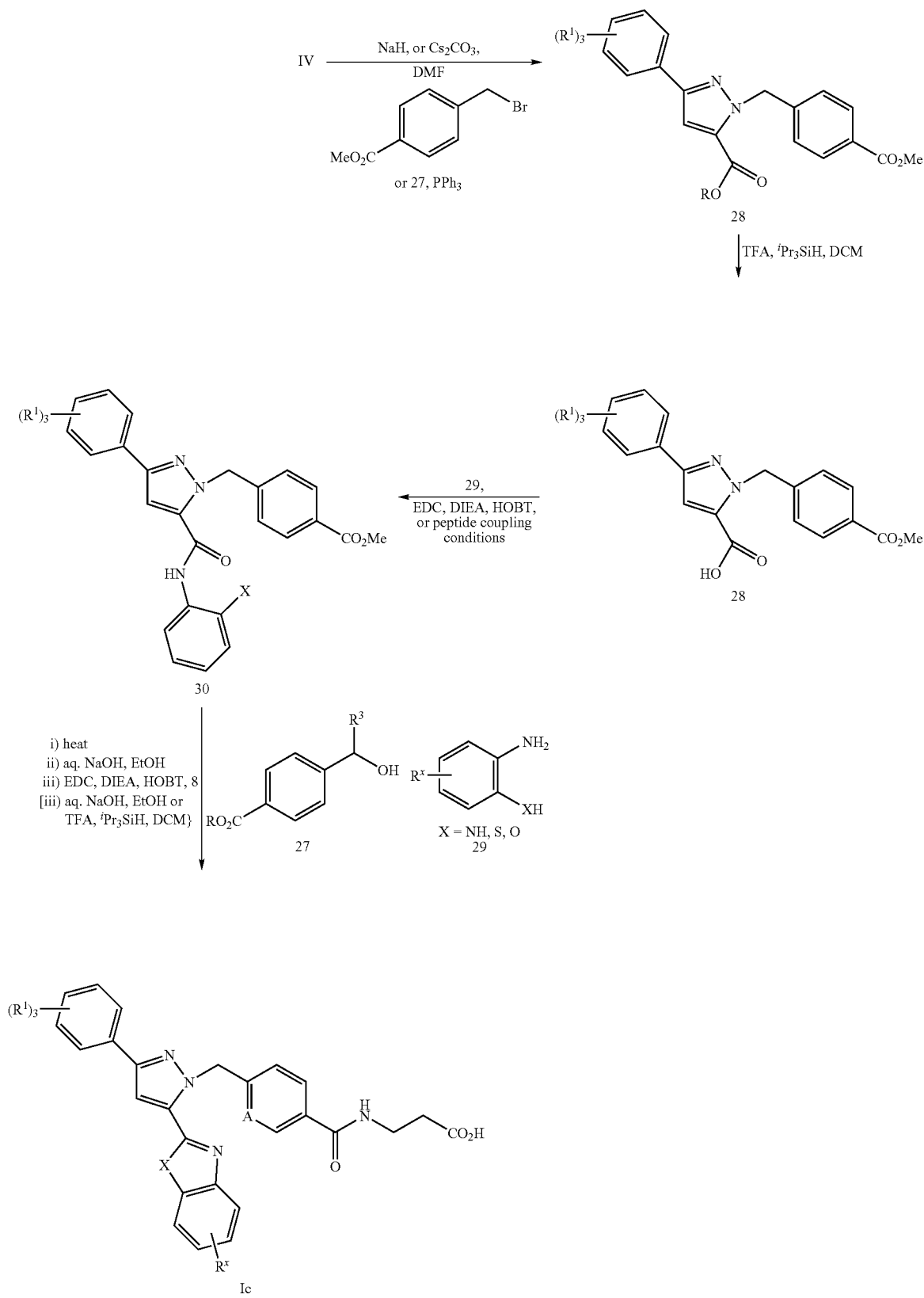

The invention is further illustrated with the following non-limiting examples.

Intermediate A

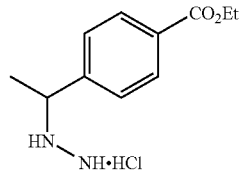

Step A tert-Butyl 2-{1-[4-(ethoxycarbonyl)phenyl]ethylidene}hydrazinecarboxylate A solution of tert-butyl carbazate (13.90 g, 105 mmol) and ethyl 4-acetylbenzoate (20.00 g, 0.104 mol) in toluene (120 mL) was stirred at 80° C. overnight (15 h). tert-butyl-2-{1-[4-(ethoxycarbonyl)phenyl]ethylidene}hydrazinecarboxylate separated as crystalline solid and was collected by filtration of the mixture. HPLC/MS: m/z=307.3 (M+1)+, $R_t$=3.47 min. $^1$H NMR (500 MHz, CDCl$_3$): δ 8.05 (2H, d, J=8.5 Hz), 7.88 (2H, d, J=8.5 Hz), 7.79 (1H, br s), 4.41 (2H, q, J=7.0 Hz), 2.24 (3H, s), 1.58 (9H, s), 1.43 (3H, t, J=7.0 Hz).

Step B tert-Butyl 2-{1-[4-(ethoxycarbonyl)phenyl]ethyl}hydrazinecarboxylate

In a N$_2$ filled round-bottomed flask equipped with serum caps and magnetic stirrer, NaBH$_3$CN (6.0 g, 0.095 mol) and tert-butyl-2-{1-[4-(ethoxycarbonyl)phenyl]-ethylidene}hydrazinecarboxylate (25.6 g, 0.084 mol) were dissolved in THF (200 mL). A solution of p-toluenesulfonic acid monohydrate (17.3 g, 0.091 mol) in THF (50 mL) was slowly added via syringe pump. Completion of addition required about 10 h. The mixture was diluted with EtOAc (200 mL) and the suspension extracted with brine (150 mL). The organic phase was separated, dried (Na$_2$SO$_4$) and concentrated on a rotovap to give white solid. The white solid was taken in CH$_2$Cl$_2$ (100 mL) and 1 N NaOH (100 mL) was added. The suspension was stirred vigorously at r.t. for 1 h and then diluted with CH$_2$Cl$_2$ (100 mL). The organic phase was separated and extracted with 1N HCl (2×150 mL), brine (2×150 mL), dried (Na$_2$SO$_4$) and concentrated to approximately 50 mL. Product precipitated as white solid and was collected by filtration and washed with hexane to yield tert-butyl 2-{1-[4-(ethoxycarbonyl)phenyl]ethyl}hydrazinecarboxylate. HPLC/MS: m/z=331.3 (M+Na)+, $R_t$=3.24 min. $^1$H NMR (500 MHz, CDCl$_3$): δ 8.03 (2H, d, J=8.0 Hz), 7.44 (2H, d, J=8.0 Hz), 5.99 (1H, br s), 4.40 (2H, q, J=7.0 Hz), 4.29 (1H, m), 1.45 (9H, s), 1.41 (3H, t, J=7.0 Hz), 1.35 (3H, d, J=6.5 Hz).

Step C {1-[4-(Ethoxycarbonyl)phenyl]ethyl}hydrazinium chloride tert-Butyl 2-{1-[4-(ethoxycarbonyl)phenyl]ethyl}hydrazinecarboxylate (29 g, 94 mmol) was treated with 100 ml of TFA-DCM-triisopropylsilane (20:20:1) at room temperature for one hour. The mixture was concentrated under reduced pressure, and the residue was dissolved in water (100 ml), washed with DCM 2×. The DCM was back extracted with water 3×. HCl (5N, 20 ml) was added to the combined water solution and concentrated to ~50 ml. CH$_3$CN (50 ml) was added and this was lyophilized to yield {1-[4-(ethoxycarbonyl)phenyl]ethyl}-hydrazinium chloride. NMR (500 MHz, acetone-d$_6$) δ: 1.34 (t, J=7.1 Hz, 3H); 1.67 (d, J=6.8 Hz, 3H); 4.33 (q, J=7.1 Hz, 2H), 4.97 (q, J=6.8 Hz, 1H), 7.76 (d, J=8.5 Hz, 2H), 7.97 (d, J=8.5 Hz, 2H). MS C$_{11}$H$_{16}$N$_2$O$_2$ Cald: 208.12; Obsd (M+1): 209.19.

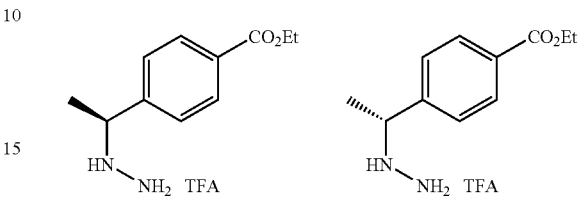

Step D {(1S)-1-[4-(ethoxycarbonyl)phenyl]ethyl}hydrazinium trifluoroacetate and {(1R)-1-[4-(ethoxycarbonyl)phenyl]ethyl}hydrazinium trifluoroacetate tert-Butyl 2-{1-[4-(ethoxycarbonyl)phenyl]ethyl}hydrazinecarboxylate was analyzed by chiral HPLC using two sets of conditions. 1) Daicel column Chiralcel OJ, 40° C., 0.75 mL/min, 10% EtOH/90% n-heptane: t$_1$ 6.66 min; t$_2$ 12.25 min. Enantiomers were resolved on a preparative scale using this column (30% EtOH/70% n-Heptane). 2) Daicel column ChiralPak AD, 0.75 mL/min, 10% EtOH/90% n-heptane: t, 12.17 min; t$_2$ 15.49 min. Enantiomers were resolved on a preparative scale using this column (20% EtOH/80% n-Heptane). The fast moving enantiomer was identical in each case and was subsequently established to be the (S)-enantiomer ($[α]_D^{20}$=−120° (c1.1, MeOH)), vide infra. The slower (R)-enantiomer was also isolated ($[α]_D^{20}$=+122° (c1.1, MeOH)).

Either enantiomer could be deprotected with 45:45:10 TFA:DCM:TIPS (40° C., 1.5 hr). The excess reagent and solvent was evaporated, and the residue was dissolved in water. The water solution was washed with DCM 2×. The DCM layers were back extracted with more water. The combined water solution was evaporated under vacuum (temp<45° C.), followed by azeotropic drying with toluene to give for the (S)-isomer-{(1S)-1-[4-(ethoxycarbonyl)phenyl]-ethyl}hydrazinium trifluoroacetate as a viscous oil. NMR (500 MHz, CD$_3$OD) δ: 1.38 (t, J=7.1 Hz, 3H); 1.49 (br d, J=7.0 Hz, 3H); 4.26 (br q, J=7.0 Hz, 1H); 4.37 (q, J=7.1 Hz, 2H); 7.54 (d, J=8.2 Hz, 2H); 8.07 (d, J=8.2 Hz, 2H). MS C$_{11}$H$_{16}$N$_2$O$_2$ Cald: 208.12; Obsd (M+1): 209.19. {(1R)-1-[4-(ethoxycarbonyl)phenyl]ethyl}hydrazinium trifluoroacetate could be prepared in an identical fashion.

Determination of Absolute Configuration of Enantiomeric Hydrazines

Absolute configuration of the enantiomers of tert-butyl 2-{1-[4-(ethoxycarbonyl)phenyl]ethyl}hydrazinecarboxylate was established by conversion to ethyl 4-[1-(2-benzoylhydrazino)ethyl]benzoate, followed by comparison of the sign of optical rotation with reported data [Burk et al., *Tetrahedron*, 1994, 50, 4399—(S)-1-p-carboethoxyphenyl-1-(2-benzoylhydrazino)ethane (95% ee; $[α]_D^{20}$=−200.00 (c1, CHCl$_3$), HPLC Daicel Chiracel OJ, 40° C., 0.5 mL/min, 10% 2-propanol/90% hexane: $R_t$=33.1 min). (R)-isomer $R_t$=37.4 min.].

Thus the slow moving enantiomer tert-butyl 2-{1-[4-(ethoxycarbonyl)phenyl]ethyl}hydrazinecarboxylate (0.74 g, 2.42 mmol) from a chiral separation as described above was treated with TFA/CH$_2$Cl$_2$ (1:1, 10 mL) for 1 h at r.t. The reaction was concentrated on a rotovap and the residual TFA was removed by co-evaporation from toluene. The resulting ethyl 4-(1-hydrazinoethyl)benzoate was then dissolved in CH$_2$Cl$_2$ (15 mL) and cooled to −78° C. A solution of benzoyl chloride (365 μL, 3.15 mmol) and 2,6-di-tert-butyl-4-methylpyridine (745 mg, 3.63 mmol) in CH$_2$Cl$_2$ (5 mL) was added slowly at −78° C. After 3 h at −78° C., the reaction mixture was loaded quickly on a SiO$_2$ column and eluted with 30% EtOAc/hexane. Fractions containing product were concentrated and purified further on HPLC using Kromasil C$_8$ column (10% to 70% CH$_3$CN/H$_2$O/0.1% TFA, 12 min), and again on silica gel column (30% EtOAc/Hexane) to give (R)-(+)-ethyl 4-[1-(2-benzoylhydrazino)ethyl]benzoate. HPLC/MS: m/z=313.3 (M+1)$^+$, R$_f$=3.08 min. Daicel column Chiralcel OJ, 40° C., 0.5 mL/min, 10% isopropanol/90% n-heptane: t 35.79 min; [α]$_D^{20}$=+192.40 (c1, CHCl$_3$); $^1$H NMR (500 MHz, CDCl$_3$): δ 8.03 (2H, d, J=8.0 Hz), 7.94 (1H, br s), 7.66 (2H, d, J=7.5 Hz), 7.51 (1H, t, J=7.5 Hz), 7.54 (2H, d, J=8.0 Hz), 7.40 (2H, t, J=8.0 Hz), 4.39 (2H, q, J=7.0 Hz), 4.36 (1H, q, J=7.0 Hz), 1.46 (3H, d, J=6.0 Hz), 1.41 (3H, t, J=7.0 Hz); $^{13}$C NMR (500 MHz, CDCl$_3$): δ 167.76, 166.69, 148.16, 132.70, 132.27, 130.21, 130.18, 128.94, 127.47, 127.15, 61.22, 60.21, 21.21, 14.58. (S)-(−)-ethyl 4-[1-(2-benzoylhydrazino)ethyl]-benzoate was similarly prepared from the faster moving isomer of tert-butyl 2-{1-[4-(ethoxycarbonyl)phenyl]ethyl}hydrazinecarboxylate. HPLC/MS: m/z=313.4 (M+1)$^+$, R$_f$=3.09 min. Daicel column Chiralcel OJ, 40° C., 0.5 mL/min, 10% isopropanol/90% n-heptane: t 34.99 min; [α]D$_{20}$=−194.4° (c1, CHCl$_3$); $^1$H NMR (500 MHz, CDCl$_3$): δ 8.02 (2H, d, J=8.0 Hz), 7.73 (1H, br s), 7.65 (2H, d, J=8.0 Hz), 7.49 (1H, t, J=8.0 Hz), 7.48 (2H, d, J=8.0 Hz), 7.39 (2H, t, J=8.0 Hz), 4.38 (2H, q, J=7.0 Hz), 4.34 (1H, q, J=7.0 Hz), 1.44 (3H, d, J=6.5 Hz), 1.41 (3H, t, J=7.0 Hz); $^{13}$C NMR (500 MHz, CDCl$_3$): δ 167.81, 166.74, 148.73, 132.92, 132.15, 130.13, 130.02, 128.90, 127.43, 127.12, 61.20, 60.09, 21.52, 14.58.

Intermediate B

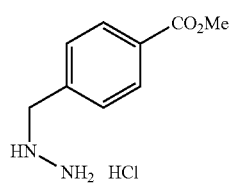

Step A tert-Butyl (2E)-2-[4-(methoxycarbonyl)benzylidene]hydrazinecarboxylate. Using chemistry described in Intermediate A, Step A above, the title compound was prepared. NMR (500 MHz, CDCl$_3$) δ: 1.55 (s, 9H); 3.92 (s, 3H); 7.74 (d, J=8.5 Hz, 2H), 7.88 (br s, 1H); 7.96 (br s, 1H); 8.04 (d, J=8.5 Hz, 2H).

Step B tert-Butyl 2-[4-(methoxycarbonyl)benzyl]hydrazinecarboxylate. Using chemistry described in Intermediate A, Step B above, the title compound was prepared. NMR (500 MHz, CDCl$_3$) δ: 1.46 (s, 9H); 3.91 (s, 3H); 4.06 (s, 2H); 6.03 (br s, 1H); 7.42 (q, J=8.3 Hz, 2H); 8.00 (d, J=8.3 Hz, 2H).

Step C [4-(Methoxycarbonyl)benzyl]hydrazinium chloride. Using chemistry described in Intermediate A, Step C above, the title compound was prepared. NMR (500 MHz, CD$_3$OD) δ: 3.91 (s, 3H); 4.19 (s, 2H); 7.54 (d, J=8.3 Hz, 2H); 8.05 (d, J=8.3 Hz, 2H). MS C$_9$H$_{12}$N$_2$O$_2$ Cald: 180.09; Obsd (M+1): 181.12.

Intermediate C 3-(3,5-dichlorophenyl)-1-[4-(methoxycarbonyl)benzyl]-1H-pyrazole-5-carboxylic acid

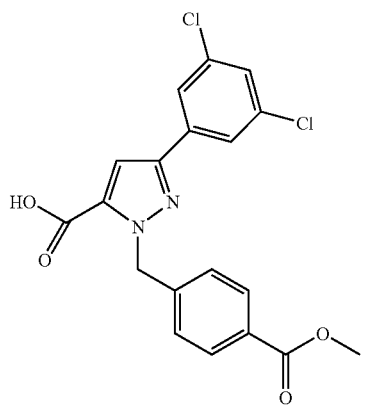

Step A 3,5-dichloro-N-methoxy-N-methylbenzamide

To a solution of 3,5-dichlorobenzoyl chloride (5 g, 23.9 mmol) in 50 mL of dichloromethane at 0° C. was added N,O-dimethylhydroxylamine hydrochloride (2.56 g, 26.3 mmol) and pyridine (4.3 mL, 52.6 mmol). The cold bath was removed and the mixture stirred at ambient temperature for 16 hours, diluted with water and extracted with two portions of dichloromethane. The combined organic layers were dried over magnesium sulfate, concentrated in vacuo, and the residue purified by flash column chromatography (SiO$_2$, 20% ethyl acetate/hexanes) to give the title compound as a colorless oil. $^1$H NMR (500 MHz, CDCl$_3$) δ: 7.61 (d, J=1.9 Hz, 2H); 7.50 (d, J=1.9 Hz, 1H); 3.60 (s, 3H); 3.40 (s, 3H).

Step B 1-(3,5-dichlorophenyl)ethanone

To the product from step A (5.42 g, 23.2 mmol) in 100 mL of tetrahydrofuran was added methylmagnesium bromide (11.6 mL, 34.8 mmol) drop-wise. After stirring at ambient temperature for 25 min, 1N hydrochloric acid was added and the mixture extracted with two portions of ethyl acetate. The combined organic layers were dried over magnesium sulfate and concentrated in vacuo to provide the title compound which was used without further purification. $^1$H NMR (500 MHz, CDCl$_3$) δ: 7.84 (d, J=1.9 Hz, 2H); 7.58 (d, J=1.8 Hz, 1H); 2.63 (s, 3H).

Step C tert-butyl 4-(3,5-dichlorophenyl)-2,4-dioxobutanoate

To a solution of the product from step B (4.1 g, 21.7 mmol) in 100 mL of diethyl ether at −78° C. was added lithium bis(trimethylsilyl)amide (23.9 mL, 23.9 mmol). After 50 min at −78° C. di-tert-butyl oxalate (4.18 g, 20.66 mmol) was added as a solid. The cold bath was removed and after 2 h an additional portion of di-tert-butyl oxalate (530 mg, 2.6 mmol) was added and stirring continued at ambient temperature for 16 h. The reaction was quenched by adding 150 mL of 1N hydrochloric acid and stirring for 1 h. The mixture was extracted with ethyl acetate and the organic layer washed with brine, dried over magnesium sulfate, and concentrated in vacuo to provide the title compound as an oil which was used without further purification. $^1$H NMR (500 MHz, CDCl$_3$) δ: 7.84 (d, J=1.9 Hz, 2H); 7.59 (d, J=1.9 Hz, 1H); 6.93 (s, 1H); 1.56 (s 9H).

Step D tert-Butyl 3-(3,5-dichlorophenyl)-1H-pyrazole-5-carboxylate

To a solution of the product from step C (6.8 g, 21.7 mmol) in 125 mL of ethanol was added hydrazine (0.75 mL, 23.9 mmol) and 10 mL of glacial acetic acid. The reaction mixture was stirred at ambient temperature for 16 h then was concentrated in vacuo and the residue suspended in ethyl acetate. The organic layer was washed successively with two portions of saturated aqueous sodium bicarbonate solution and one portion of brine. The organic layer was dried over magnesium sulfate, and concentrated in vacuo to provide the title compound as a pale yellow solid which was used without further purification.

Step E tert-Butyl 3-[3,5-dichlorophenyl]-1-[4-(methoxycarbonyl)benzyl]-1H-pyrazole-5-carboxylate To a solution of the product from step D (6.8 g, 21.7 mmol) in 50 mL of N,N-dimethylformamide was added cesium carbonate (10.6 g, 32.6 mmol) and the resultant mixture stirred at ambient temperature for 15 min. Methyl 4-(bromo-methyl)benzoate (5.46 g, 23.9 mmol) was added and stirring continued for 3 h. The reaction mixture was diluted with ethyl acetate and the organic layer washed successively with six portions of water and one portion of brine then dried over magnesium sulfate and concentrated in vacuo. The residue was purified by flash column chromatography (SiO$_2$, 5% ethyl acetate/hexanes) to give the title compound as a light tan solid. $^1$H NMR (500 MHz, CDCl$_3$) δ: 8.03 (d, J=8.4 Hz, 2H); 7.75 (d, J=1.8 Hz, 2H); 7.35 (m, 3H); 7.12 (s, 1H); 5.88 (s, 2H); 3.94 (s, 3H); 1.57 (s, 9H).

Step F

3-(3,5-dichlorophenyl)-1-[4-(methoxycarbonyl)benzyl]-1H-pyrazole-5-carboxylic acid To a solution of the product from step E (5.54 g, 12 mmol) in 30 mL of dichloromethane was added 13 mL of trifluoroacetic acid. The reaction mixture was stirred at ambient temperature for 16 h then was concentrated in vacuo and excess trifluoroacetic acid removed by azeotropic distillation with dichloromethane to provide the title compound as a white solid. $^1$H NMR (500 MHz, CDCl$_3$) δ: 8.00 (d, J=8.2 Hz, 2H); 7.83 (d, J=1.8 Hz, 2H); 7.41 (d, J=1.9 Hz, 1H); 7.36 (d, J=8.3 Hz, 2H); 7.32 (s, 1H); 5.94 (s, 2H); 4.87 (s, 3H).

Intermediate D

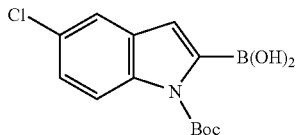

Step A tert-Butyl 5-chloro-1H-indole-1-carboxylate

2-Chloroindole (1.0 g, 6.6 mmol), and di-t-butyldicarbonate (2.2 g, 10 mmol), and Cs$_2$CO$_3$ (3.2 g, 9.9 mmol) were stirred in DMF (30 ml) at room temperature for 4 hr. The reaction mixture was diluted with ethyl acetate and washed with 1N HCl (2×), 5% K$_2$CO$_3$ (2×), and brine. The crude product was flash chromatographed (SiO$_2$ gel, 0% to 10% DCM in hexanes gradient) to give tert-butyl 5-chloro-1H-indole-1-carboxylate as a colorless oil. NMR (500 MHz, CDCl$_3$) δ: 1.67 (s, 9H); 6.51 (d, J=3.7 Hz, 1H); 7.26 (dd, J=2.3, 9 Hz, 1H); 7.53 (d, J=2.3 Hz, 1H); 7.61 (d, J=3.7 Hz, 1H); 8.07 (d, J=9 Hz, 1H).

Step B

[1-(tert-Butoxycarbonyl)-5-chloro-1H-indol-2-yl]boronic acid

A solution of LDA (3.4 ml, 7 mmol) was added slowly to a mixture of tert-butyl 5-chloro-1H-indole-1-carboxylate (0.5 g, 2 mmol), triisopropylborate (0.7 ml, 3 mmol) in THF (5 ml) at 0° C. The mixture was stirred for 30 min at 0° C., and quenched with 2N HCl. The crude product was purified with reverse phase HPLC to give, after lyophilization, [1-(tert-Butoxycarbonyl)-5-chloro-1H-indol-2-yl]boronic acid as a white powder. NMR (500 MHz, CDCl$_3$) δ: 1.51 (s, 9H); 6.7 (br s, 2H); 7.01 (s, 1H); 7.25 (d, J=8.3 Hz, 1H); 7.45 (d, J=8.3 Hz, 1H); 8.12 (s, 1H).

Intermediate E

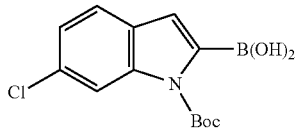

[1-(tert-Butoxycarbonyl)-6-chloro-1H-indol-2-yl]boronic acid

This compound was made in a similar way as intermediate D. NMR (500 MHz, CDCl$_3$) δ: 1.75 (s, 9H); 6.9 (br s, 2H); 7.24 (dd, J=2.0, 8.5 Hz, 1H); 7.44 (s, 1H); 7.51 (d, J=8.5 Hz, 1H); 8.04 (d, J=2.0 Hz, 1H).

Intermediate F

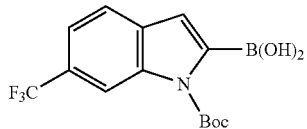

[1-(tert-butoxycarbonyl)-6-(trifluoromethyl)-1H-indol-2-yl]boronic acid

This compound was made in a similar way as intermediate D. NMR (500 MHz, CDCl$_3$) δ: 1.49 (s, 9H); 7.01 (s, 2H); 7.04 (dd, J=2.3, 9.0 Hz, 1H); 7.15 (s, 1H); 7.31 (d, J=2.3 Hz, 1H); 7.67 (d, J=9.0 Hz, 1H).

Example 1

N-(4-{(1S)-1-[3-(3,5-DICHLOROPHENYL)-5-QUINOLIN-3-YL-1H-PYRAZOL-1-YL]ETHYL}BENZOYL)-β-ALANINE

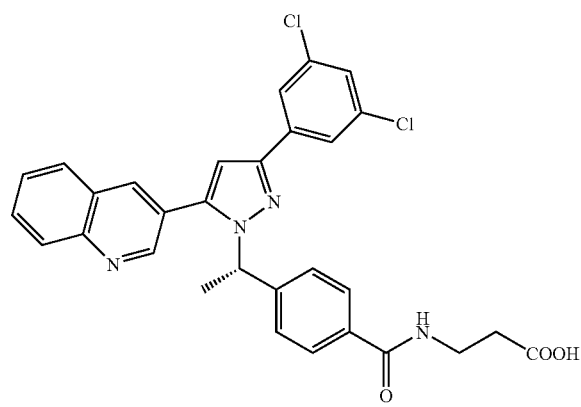

Step A

N-methoxy-N-methylquinoline-3-carboxamide

To a suspension of the quinoline-3-carboxylic acid (480 mg, 2.77 mmol) and N,O-dimethyhydroxylamine hydrochloride (405 mg, 4.15 mmol), in dichloromethane (10 mL) was added triethyl amine (1.93 mL, 13.8 mmol) followed by bromo(trispyrrolidin-1yl)phosphonium hexafluorophosphate (1.55 g, 3.32 mmol). After stirring the reaction mixture at room temperature for 1 hour, it was quenched by the addition of water (10 mL). The resulting mixture was extracted with DCM. The organic layer dried over anhydrous Na$_2$SO$_4$, filtered and concentrated in vacuo. The residue was purified by flash chromatography using 75% ethyl acetate-hexanes. $^1$H NMR (500 MHz, CDCl$_3$): 8.25 (d, J=1.8 Hz, 1H), 8.67 (d, J=1.3 Hz, 1H), 8.18 (d, J=8.5 Hz, 1H), 7.96 (d, J=8.2 Hz, 1H), 7.84 (t, J=8.0 Hz, 1H), 7.65 (t, J=8.5 Hz, 1H), 3.61 (s, 3H), 3.48 (s, 3H). LC-MS: 1.24 min; (M+H)=217.1.

Step B 1,3-dichloro-5-ethynyl benzene

To a solution of zinc, bromide (5.0 g, 22.2 mmol) in anhydrous THF (100 mL) at room temperature under a nitrogen atmosphere was added a solution of ethynyl magnesium bromide (0.5 M in THF, 44.4 mL, 44.4 mmol). After 5 minutes 3,5-dichloro-iodobenzene was added (4.03 g, 14.8 mmol) followed by tetrakis-triphenyl phosphine palladium (0) (855 mg, 0.74 mmol). The reaction was stirred at room temperature for 18 hours. The reaction mixture was poured into brine and extracted with ether (4×100 mL). The ether layer was washed with brine, dried over anhydrous MgSO$_4$, filtered and concentrated in vacuo. The residue was purified by flash chromatography with 100% hexanes to give the title compound as a yellow solid. $^1$H NMR (CDCl$_3$, 500 MHz): 7.4 (d, J=1.6 Hz, 2H), 7.3 (d, J=1.6 Hz, 1H), 3.19 (s, 1H).

Step C 3-(3,5-dichlorophenyl)-1-quinolin-3-ylprop-2-yn-1-one

To a solution of the 1,3-dichloro-5-ethynylbenzene (200 mg, 1.16 mmol) in anhydrous THF cooled to −78° C. under a N$_2$ atmosphere was added nButLi (800 μL, 1.28 mmol). After 5 minutes a solution of the intermediate from step A (380 mg, 1.75 mmol) in THF (3 mL) was added. The reaction was gradually warmed to room temperature over 30 minutes and quenched with saturated NH$_4$Cl solution. The resulting biphasic mixture was extracted with ethyl acetate, washed with saturated NaCl solution, dried over anhydrous Na$_2$SO$_4$, filtered and concentrated in vacuo. The residue was purified by flash chromatography using 15% ethyl acetate-hexanes to afford the product as a light yellow solid. $^1$H NMR (CDCl$_3$, 500 MHz): 9.63 (s, J=2.1 Hz, 1H), 8.96 (d, J=1.6 Hz, 1H), 8.24 (d, J=8.5 Hz, 1H), 8.07 (d, J=8.3 Hz, 1H), 7.94 (t, J=8.0 Hz, 1H), 7.73 (t, J=7.8 Hz, 1H), 7.64 (d, J=1.8 Hz, 2H), 7.55 (t, J=2.0 Hz, 1H). LC-MS: 3.99 min; (M+H)=326.0.

Step D ethyl 4-{(1S)-1-[3-(3,5-dichlorophenyl)-5-quinolin-3-yl-1H-pyrazol-1-yl]ethyl}benzoate To a solution of the intermediate from step C (152 mg, 0.46 mmol) in DMF (5 mL) was added the ethyl 4-[(1S)-1-hydrazinoethyl]benzoate hydrochloride (126 mg, 0.51 mmol) and triethyl amine (86 μL, 0.61 mmol). After stirring, the reaction mixture at room temperature for 2 hours it was concentrated in vacuo. The residue was diluted with water and ethyl acetate. The organic layer was washed with brine, dried over anhydrous Na$_2$SO$_4$, filtered and concentrated in vacuo. The residue was purified by flash chromatography using 10% ethyl acetate-hexanes. This material was then re-purified with 75% hexanes-dichloromethane to give the desired compound as the major product. $^1$H NMR (CDCl$_3$, 500 MHz): 8.84 (d, J=2.0 Hz, 1H), 8.18 (d, J=8.5 Hz, 1H), 8.03 (d, J=8.2 Hz, 2H), 7.99 (d, J=2.1 Hz, 1H), 7.83 (d, J=1.8 Hz, 2H), 7.78 (m, 1H), 7.62 (t, J=8.0 Hz, 1H), 7.34 (t, J=1.8 Hz, 1H), 7.28 (d, J=8.2 Hz, 2H), 6.77 (s, 1H), 5.58 (q, J=7.1 Hz, 1H), 4.41 (q, J=7.1 Hz, 2H), 2.02 (d, J=7.1 Hz, 3H), 1.4 (t, J=7.0 Hz, 3H). LC-MS: 4.64 min; (M+H)=516.3.

Step E

4-{(1S)-1-[3-(3,5-dichlorophenyl)-5-quinolin-3-yl-1H-pyrazol-1-yl]ethyl}benzoic acid To a solution of the intermediate from step D (125 mg, 0.24 mmol) in 5 mL of THF was added MeOH (1 mL) followed by sodium hydroxide (5N, 0.5 mL). After stirring the reaction at room temperature for 18 hours, it was concentrated in vacuo to remove THF/MeOH. The resulting aqueous mixture was acidified with 1N HCl until the pH was slightly acidic (pH=5). The resulting solution was extracted with EtOAc (3×), and the combined organic layers were then washed with brine, dried over anhydrous MgSO$_4$, filtered and concentrated in vacuo. The resulting white solid was used without further purification. LC-MS: 4.03 min; (M+H)=488.3.

Step F tert-butyl N-(4-{(1S)-1-[3-(3,5-dichlorophenyl)-5-quinolin-3-yl-1H-pyrazol-1-yl]ethyl}benzoyl)-β-alaninate To a solution of the intermediate form step E (120 mg, 0.24 mmol) in 2 mL of anhydrous DMF was added tert-butyl β-alaninate hydrochloride (66 mg, 0.36 mmol), 1-hydroxy-7-azabenzo-triazole (50 mg, 0.36 mmol), N,N-diisopropyl-ethyl amine (127 μL, 0.72 mmol), and 1-[3-(dimethylamino)propyl]-3-ethyl carbodiimide hydrochloride (70 mg, 0.36 mmol). The reaction was left stirring at room temperature for 4 hours then diluted with EtOAc and washed with 1N HCl (2×), saturated sodium bicarbonate (2×), and brine (1×). The organic layer was then dried over anhydrous MgSO$_4$, filtered and concentrated in vacuo. The resulting solid was purified by flash chromatography (45% EtOAc/Hexanes). $^1$H NMR (CDCl$_3$, 500 MHz): 8.86 (d, J=1.8 Hz, 1H), 8.2 (d, J=8.5 Hz, 1H), 8.0 (d, J=1.8 Hz, 1H), 7.84 (d, J=1.8 Hz, 2H), 7.78 (m, 1H), 7.75 (d, J=8.2 Hz, 2H), 7.66 (t, J=7.1 Hz, 1H), 7.35 (t, J=1.8 Hz, 1H), 7.29 (d, J=8.2 Hz, 2H), 6.91 (bt, J=1.8 Hz, 1H), 6.77 (s, 1H), 5.57 (q, J=7.0 Hz, 1H), 3.72 (q, J=5.9 Hz, 2H), 2.58 (t, J=6.0 Hz, 2H), 2.01 (d, J=7.1 Hz, 3H), 1.48 (s, 9H). LC-MS: 4.3 min; (M+H)=615.0.

Step G

N-(4-{(1S)-1-[3-(3,5-dichlorophenyl)-5-quinolin-3-yl-1H-pyrazol-1-yl]ethyl}benzoyl)-β-alanine To a solution of the intermediate from step F (128 mg) in CH$_2$Cl$_2$ (2 mL) was added TFA (2 mL). After the reaction was stirred at room temperature for 30 minutes, it was concentrated in vacuo and azeotroped with toluene (3×). The resulting light yellow solid was dissolved in 1,4-dioxane and lyophilized overnight to afford the title compound as a white solid. $^1$H NMR (CD$_3$OD, 500 MHz) 8.82 (d, J=1.8 Hz, 1H), 8.42 (s, 1H), 8.12 (d, J=8.5 Hz, 1H), 7.99 (d, J=8.0 Hz, 1H), 7.93 (t, J=7.3 Hz, 1H), 7.90 (d, J=1.6 Hz, 2H), 7.77 (t, J=7.5 Hz, 2H), 7.71 (d, J=8.3 Hz, 2H), 7.4 (s, 1H), 7.24 (d, J=8.3 Hz, 2H), 7.06 (s, 1H), 5.71 (q, J=6.8 Hz, 1H), 3.66 (t, J=6.9 Hz, 2H), 2.63 (t, J=7.1 Hz, 2H), 2.01 (d, J=6.8 Hz, 3H). LC-MS: 3.68 min; (M+H)=559.1.

Example 2

N-(4-{(1S)-1-[3-(3,5-DICHLOROPHENYL)-5-(7-METHOXYQUINOLIN-3-YL)-1H-PYRAZOL-1-YL]ETHYL}BENZOYL)-β-ALANINE

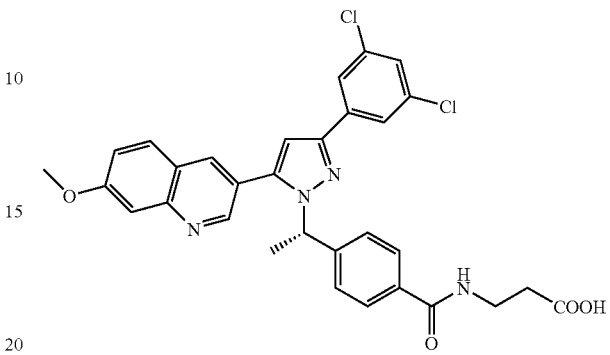

Step A

Ethyl 4-hydroxy-7-methoxyquinoline-3-carboxylate

To a solution of m-anisidine (1.1 μg, 8.94 mmol) in toluene (5 mL) was added diethylethoxymethylene malonate (1.93 g, 8.94 mmol). After refluxing the reaction for 45 minutes, it was concentrated in vacuo. The residue was dissolved in phenyl ether (5 mL) and added to a solution of refluxing phenyl ether (10 mL). After 1 hour, the reaction was cooled to room temperature. A precipitate crashed out. The reaction was diluted with hexanes and filtered to give a yellow solid. LC-MS: 2.08 min; (M+H)=248.2.

Step B

Ethyl 4-chloro-7-methoxyquinoline-3-carboxylate

The intermediate from step A (890 mg, mmol) was suspended in POCl$_3$ (5 mL) and refluxed for 1 hour. The reaction was cooled to room temperature and poured into an erlenmeyer flask containing ice and 5 N NaOH (30 mL). The resulting mixture was extracted with ethyl acetate (3×). The organic layer was washed with saturated NaHCO$_3$, saturated NaCl solution dried over anhydrous Na$_2$SO$_4$, filtered and concentrated in vacuo. The residue was purified by flash chromatography using 30% ethyl acetate-hexanes to afford the product as a white solid. $^1$H NMR (500 MHz, CDCl$_3$): 9.19 (s, 1H), 8.33 (s, J=9.2 Hz, 1H), 7.46 (d, J=2.5 Hz, 1H), 7.36 (dd, J=2.5, 9.1 Hz, 1H), 4.53 (q, J=7.1 Hz, 2H), 4.01 (s, 3H), 1.5 (t, J=7.4 Hz, 3H). LC-MS: 3.22 min; (M+H)=266.1.

Step C

Ethyl 7-methoxyquinoline-3-carboxylate

To a solution of the intermediate from step, B (400 mg) in 1:1 ethanol-ethyl acetate was added Pd/C (20 mg) and the resulting reaction stirred under a hydrogen balloon for 3 hours. The reaction was diluted with ethyl acetate and filtered through celite. The filtrate was concentrated in vacuo to give the desired product. This material was used in the next step without any further purification. $^1$H NMR (500 MHz, CDCl$_3$): 9.37 (s, 1H), 9.26 (s, 1H), 8.1 (s, 1H), 8.09 (d, J=10.3 Hz, 1H), 7.51 (d, J=9.3 Hz, 1H), 4.49 (q, J=7.1 Hz, 2H), 4.06 (s, 3H), 1.42 (t, J=7.1 Hz, 3H). LC-MS: 2.31 min; (M+H)= 232.1.

Step D

7-methoxyquinoline-3-carboxylic acid

To a solution of the intermediate from step C (399 mg, mmol) in THF (6 mL) was added methanol (1 mL) followed by NaOH (5N, 1.5 mL). After stirring at room temperature for 18 hours the reaction was concentrated in vacuo. The residue was acidified with 1N HCl (10 mL). The solution was concentrated in vacuo and azeotroped with toluene (4×). This material was used in the next step without any further purification.

Step E

N,7-dimethoxy-N-methylquinoline-3-carboxamide

To a suspension of the intermediate from step D (1.5 mmol) and N,O-dimethyhydroxylamine hydrochloride (219 mg, 2.25 mmol), in dichloromethane (20 mL) was added triethyl amine (1.04 mL, 7.5 mmol) followed by bromo(trispyrrolidin-1yl)phosphonium hexafluorophosphate (840 mg, 1.8 mmol). After stirring the reaction mixture at room temperature for 3 hours, it was quenched by the addition of 1N HCl (10 mL). The resulting mixture was extracted with DCM. The organic layer was washed with saturated NaHCO$_3$ solution, dried over anhydrous Na$_2$SO$_4$, filtered and concentrated in vacuo. The residue was purified by flash chromatography using 70% ethyl acetate-hexanes. $^1$H NMR (500 MHz, CDCl$_3$): 9.15 (d, J=1.8 Hz, 1H), 8.5 (d, J=1.8 Hz, 1H), 8.0 (s, 1H), 7.7 (d, J=9.0 Hz, 1H), 7.43 (d, J=2.2 Hz, 1H), 7.24 (dd, J=2.5, 9.0 Hz, 1H), 3.96 (s, 3H), 3.57 (s, 3H), 3.43 (s, 3H). LC-MS: 1.6 min; (M+H)=247.1.

Step F

3-(3,5-dichlorophenyl)-1-(7-methoxyquinolin-3-yl) prop-2-yn-1-one

To a solution of the 1,3-dichloro-5-ethynylbenzene (185 mg, 1.08 mmol) in anhydrous THF cooled to −78° C. under a N$_2$ atmosphere was added nButLi (750 µL, 1.18 mmol). After 5 minutes, a solution of the intermediate from step E (320 mg, 1.3 mmol) in THF (5 mL) was added. The reaction was gradually warmed to room temperature over 30 minutes and quenched with saturated NH$_4$Cl solution. The resulting biphasic mixture was extracted with ethyl acetate, washed with saturated NaCl solution, dried over anhydrous Na$_2$SO$_4$, filtered and concentrated in vacuo. The residue was purified by flash chromatography using 20% ethyl acetate-hexanes to afford the product as a light yellow solid. $^1$H NMR (500 MHz, CDCl$_3$): 9.54 (d, J=2.3 Hz, 1H), 8.85 (d, J=2.1 Hz, 1H), 7.92 (d, J=9.2 Hz, 1H), 7.62 (d, J=2.0 Hz, 2H), 7.5 (m, 2H), 7.34 (dd, J=2.5, 8.9 Hz, 1H), 4.04 (s, 3H). LC-MS: 3.92 min; (M+H)=356.0.

Step G

Ethyl 4-{(1S)-1-[3-(3,5-dichlorophenyl)-5-(7-methoxyquinolin-3-yl)-1H-pyrazol-1-yl]ethyl}benzoate To a solution of the intermediate from step F (118 mg, 0.33 mmol) in DMF was added the ethyl 4-[(1S)-1-hydrazinoethyl]benzoate hydrochloride (89 mg, 0.36 mmol) and triethyl amine (55 µL, 0.39 mmol). After stirring the reaction mixture at room temperature for 18 hours it was concentrated in vacuo. The residue was diluted with water and ethyl acetate. The organic layer was washed with brine, dried over anhydrous Na$_2$SO$_4$, filtered and concentrated in vacuo. The residue was purified by flash chromatography using 25% ethyl acetate-hexanes. This material was then re-purified with 3% acetonitrile-dichloromethane to give the desired compound. $^1$H NMR (500 MHz, CDCl$_3$): 8.76 (d, J=2.0 Hz, 1H), 8.04 (d, J=8.2 Hz, 2H), 7.92 (1.8 Hz, 1H), 7.85 (d, J=1.8 Hz, 2H), 7.68 (d, J=8.9 Hz, 1H), 7.5 (d, J=2.1 Hz, 1H), 7.36 (t, J=1.8 Hz, 1H), 7.31 (d, J=8.0 Hz, 2H), 6.76 (s, 1H), 4.42 (q, J=7.0 Hz, 1H), 4.03 (s, 3H), 2.04 (s, 3H), 2.01 (t, J=7.1 Hz, 2H), 1.43 (t, J=7.1 Hz, 3H). LC-MS: 4.28 min; (M+H)=546.0.

Step H

4-{(1S)-1-[3-(3,5-dichlorophenyl)-5-(7-methoxyquinolin-3-yl)-1H-pyrazol-1-yl]ethyl}benzoic acid To a solution of the intermediate from step G (67 mg, 0.12 mmol) in 4 mL of 1:1 THF/MeOH was added sodium hydroxide (5N, 1 mL). After stirring the reaction at room temperature for 1 hour it was concentrated in vacuo to remove THF/MeOH. The resulting aqueous mixture was acidified with 1N HCl until the pH was slightly acidic (pH=5). The resulting solution was extracted with EtOAc (3×), and the combined organic layers were then washed with brine, dried over anhydrous MgSO$_4$, filtered and concentrated in vacuo. The resulting white solid was used without further purification.

Step I tert-butyl N-(4-{(1S)-1-[3-(3,5-dichlorophenyl)-5-(7-methoxyquinolin-3-yl)-1H-pyrazol-1-yl]ethyl}benzoyl)-β-alaninate To a solution of the intermediate form step H (59 mg, 0.11 mmol) in 2 mL of anhydrous DMF was added tert-butyl β-alaninate hydrochloride (33 mg, 0.18 mmol), 1-hydroxy-7-azabenzo-triazole (25 mg, 0.18 mmol), N,N-diisopropylethyl amine (64 µL, 0.36 mmol), and 1-[3-(dimethylamino)propyl]-3-ethyl carbodiimide hydrochloride (35 mg, 0.18 mmol). The reaction was left stirring at room temperature for 12 hours then diluted with EtOAc and washed with 1N HCl (2×), saturated sodium bicarbonate (2×), and brine (1×). The organic layer was then dried over anhydrous MgSO$_4$, filtered and concentrated in vacuo. The resulting solid was purified by flash chromatography (50% EtOAc/Hexanes) to afford a white solid. $^1$H NMR (500 MHz, CDCl$_3$): 8.75 (bs, 1H), 7.9 (s, 1H), 7.83 (d, J=1.8 Hz, 2H), 7.75 (d, J=8.2 Hz, 2H), 7.67 (d, J=9.0 Hz, 1H), 7.48 (s, 1H), 7.34 (t, J=1.9 Hz, 1H), 7.3 (d, J=8.3 Hz, 2H), 6.92 (t, J=5.7 Hz, 1H), 6.73 (s, 1H), 5.56 (q, J=6.8 Hz, 2H), 4.01 (s, 3H), 3.71 (q, J=6.0 Hz, 2H), 2.58 (t, J=5.7 Hz, 2H), 2.0 (d, J=6.9 Hz, 3H), 1.48 (s, 9H). LC-MS: 4.07 min; (M+H)=645.0.

Step J

N-(4-{(1S)-1-[3-(3,5-dichlorophenyl)-5-(7-methoxyquinolin-3-yl)-1H-pyrazol-1-yl]ethyl}benzoyl)-β-alanine To a solution of the intermediate from step I (64 mg) in CH$_2$Cl$_2$ (2 mL) was added TFA (2 mL). After the reaction was stirred at room temperature for 30 minutes it was concentrated in vacuo and azeotroped with toluene (3×). The resulting light yellow solid was dissolved in 1,4-dioxane and lyophilized overnight to afford the product as a white solid. $^1$H NMR (DMSO, 500 MHz) 8.8 (d, J=1.6 Hz, 1H), 8.45 (t, J=5.5

Hz, 1H), 8.38 (s, 1H), 7.94 (s, 2H), 7.92 (d, J=8.4 Hz, 2H), 7.72 (d, J=8.0 Hz, 2H), 7.58 (s, 1H), 7.45 (d, J=2.1 Hz, 1H), 7.37 (dd, J=2.3, 8.7 Hz, 1H), 7.28 (s, 1H), 7.2 (d, J=8.0 Hz, 2H), 5.8 (q, J=6.9 Hz, 1H), 3.95 (s, 3H), 3.41 (q, J=6.9 Hz, 2H), 2.45 (t, J=7.1 Hz, 2H), 1.93 (d, J=6.9 Hz, 3H). LC-MS: 3.53 min; (M+H)=588.9.

Example 3

N-(4-{1-[3-(3,5-DICHLOROPHENYL)-5-QUINOXALIN-6-YL-1H-PYRAZOL-1-YL]ETHYL}BENZOYL)-β-ALANINE-ISOMER 1

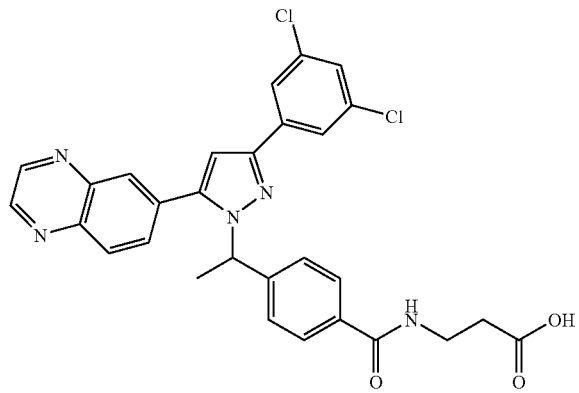

Step A

Quinoxaline-6-carboxylic acid

To a solution of methyl quinoxaline-6-carboxylate (500 mg, 2.66 mmol) in 10 mL of THF was added sodium hydroxide (5N, 2.5 mL, 12.5 mmol) followed by methanol (2.5 mL). The reaction was stirred at room temperature overnight and then concentrated in vacuo to remove THF/MeOH. The resulting aqueous mixture was acidified with 1N HCl until the pH was slightly acidic (pH=5). The resulting solution was extracted with EtOAc (3×), and the combined organic layers were then washed with brine, dried over anhydrous MgSO₄, filtered and concentrated in vacuo. The resulting white solid was used without further purification. LC-MS: 3.50 min. (M+H)=175.16.

Step B

Quinoxaline-6-carbonyl chloride

To a solution of quinoxaline-6-carboxylic acid (438 mg, 2.51 mmol) in benzene (16 mL) was added oxalyl chloride (0.26 mL, 3.02 mmol) and anhydrous DMF (0.1 mL). The reaction was stirred at room temperature for 30 minutes after which the mixture was concentrated in vacuo. The resulting yellow solid was azeotroped 3× with toluene and the product was used immediately without further purification.

Step C

N-methoxy-N-methylquinoxaline-6-carboxamide

To a solution of intermediate from step B (484 mg, 2.51 mmol) in 17 mL anhydrous methylene chloride cooled to 0° C. was added N,O-dimethylhydroxylamine hydrochloride (368 mg, 3.77 mmol) followed by pyridine (0.61 mL, 7.54 mmol). The reaction was warmed to room temperature and stirred overnight after which it was quenched with water. The aqueous layer was extracted with methylene chloride (2×) and the combined organic layers were dried over anhydrous MgSO₄, filtered and concentrated in vacuo. The resulting oil was purified by flash column chromatography using 40% EtOAc/Hexanes to give the product as a colorless oil. ¹H NMR (CDCl₃, 500 MHz): 3.45 (d, J=2.5 Hz, 3H), 3.59 (d, J=2.5 Hz, 3H), 8.05 (m, 1H), 8.15 (dd, J=8.7, 3.2 Hz, 1H), 8.46 (d, J=1.8 Hz, 1H), 8.91 (d, J=2.5, 2H). LC-MS: 1.11 min. (M+H)=111.

Step D

3-(3,5-dichlorophenyl)-1-quinoxalin-6-ylprop-2-yn-1-one

This compound was synthesized using the procedure described in example 1 step C. ¹H NMR (CDCl₃, 500 MHz): 7.55 (t, J=1.8 Hz, 1H), 7.66 (d, J=1.9 Hz, 2H), 8.27 (d, J=8.9 Hz, 1H), 8.51 (dd, J=8.95, 1.8 Hz, 1H), 9.03 (dd, J=7.35, 1.8 Hz, 3H).

Step E

6-[5-(3,5-dichlorophenyl)-1H-pyrazol-3-yl]quinoxaline

To a solution of the intermediate from step D (316 mg, 0.97 mmol) in 7 mL of anhydrous DMF was added hydrazine (0.03 mL, 1.06 mmol). The reaction was stirred at room temperature overnight and then concentrated in vacuo. The resulting residue was azeotroped 2× with toluene then dissolved in EtOAc and washed with water (1×), brine (1×), dried over anhydrous MgSO₄, filtered and concentrated in vacuo. The resulting solid was used without further purification. LC-MS: 3.62 min. (M+H)=342.19.

Step F

Tert-butyl 4-{1-[3-(3,5-dichlorophenyl)-5-quinoxalin-6-yl-1H-pyrazol-1-yl]ethyl}benzoate To a solution of the intermediate from step E (330 mg, 0.97 mmol) in 8 mL of anhydrous DMF was added Cs₂CO₃ (473 mg, 1.45 mmol) followed by tert-butyl 4-(1-bromoethyl)benzoate (331 mg, 1.16 mmol). The reaction was stirred at room temperature overnight and then diluted with water. The aqueous layer was then extracted with EtOAc (3×) and the combined organic layers were then washed with brine, dried over anhydrous MgSO₄, filtered and concentrated in vacuo. The resulting oil was purified by flash chromatography (20% EtOAc/Hexanes) to give the product as a yellow oil. ¹H NMR (CDCl₃, 500 MHz): 1.60 (s, 9H), 2.02 (d, J=7.1 Hz, 3H), 5.67 (q, J=7.1 Hz, 1H), 6.78 (s, 1H), 7.26 (d, J=8.2 Hz, 2H), 7.34 (t, J=1.8 Hz, 1H), 7.68 (dd, J=8.7, 1.9 Hz, 1H), 7.83 (d, J=1.8, 2H), 7.95 (d, J=8.2 Hz, 2H), 8.10 (d, J=1.9, 1H), 8.18 (d, J=8.7, 1H), 8.94 (s, 2H). LC-MS: 4.74, 4.89 min. (M+H)=546.46.

Step G

4-{1-[3-(3,5-dichlorophenyl)-5-quinoxalin-6-yl-1H-pyrazol-1-yl]ethyl}benzoic acid The intermediate from step F (40 mg, 0.07 mmol) was dissolved in 1:1 CH$_2$Cl$_2$:TFA (4 mL) and stirred at room temperature for 30 minutes. The reaction mixture was concentrated in vacuo and azeotroped with toluene (3×). The resulting light yellow solid was used without further purification. LC-MS: 4.18 min. (M+H)=490.35.

Step H

Ethyl N-(4-{1-[3-(3,5-dichlorophenyl)-5-quinoxalin-6-yl-1H-pyrazol-1-yl]ethyl}benzoyl)-β-alaninate To a solution of the intermediate from step G (39.7 mg, 0.08 mmol) in 3 mL of anhydrous DMF was added ethyl β-alaninate hydrochloride (19 mg, 0.12), 1-hydroxy-7-azabenzo-triazole (17 mg, 0.12 mmol), N,N-diisopropylethyl amine (0.04 mL, 0.24 mmol), and 1-[3-(dimethylamino)propyl]-3-ethyl carbodiimide hydrochloride (24 mg, 0.12 mmol). The reaction was left stirring at room temperature for 12 hours then diluted with EtOAc and washed with 1N HCl (2×), saturated sodium bicarbonate (2×), and brine (1×). The organic layer was then dried over anhydrous MgSO$_4$, filtered and concentrated in vacuo. The resulting solid was purified by flash chromatography (30% EtOAc/Hexanes) to afford a light yellow solid. Enantiomers were then separated using SFC-HPLC semi-prep methodology with the conditions as follows: column=ChiralCel OJ 10×250 mm 10 micron, flow rate=10.0 mL/min, mobile Phase=40% MeOH (0.1% TFA)/CO$_2$, column temperature=40° C., UV wavelength=248 nm, outlet pressure=100 bar, concentration=50 mg/mL in MeOH. Retention time: Isomer A=4.03 min; Isomer B=5.01 min. LC-MS: 4.20 min. (M+H)=589.48.

Step I

N-(4-{(1-[3-(3,5-dichlorophenyl)-5-quinoxalin-6-yl-1H-pyrazol-1-yl]ethyl}benzoyl)-β-alanine—isomer 1

To a solution of isomer A from step H (17.1 mg, 0.03 mmol) in 2 mL of THF was added sodium hydroxide (5N, 1.5 mL, 7.5 mmol) followed by methanol (2.5 mL). The reaction was stirred at room temperature overnight and then concentrated in vacuo to remove THF/MeOH. The resulting aqueous mixture was acidified with 1N HCl until the pH was slightly acidic (pH=5). The resulting solution was extracted with EtOAc (3×), and the combined organic layers were then washed with brine, dried over anhydrous MgSO$_4$, filtered and concentrated in vacuo. The resulting light yellow solid was dissolved in 1,4-dioxane and lyophilized overnight to afford the product as a white solid. $^1$H NMR (DMSO, 500 MHz): 1.93 (d, J=6.8 Hz, 3H), 2.2 (m, 2H), 3.15 (m, 2H), 5.84 (q, J=6.7 Hz, 1H), 7.22 (d, J=8.2 Hz, 2H), 7.34 (s, 1H), 7.59 (t, J=1.9 Hz, 1H), 7.73 (d, J=8.5 Hz, 2H), 7.88 (dd, J=8.6, 2.1 Hz, 1H), 7.96 (d, J=1.8 Hz, 2H), 8.07 (d, J=2.1 Hz, 1H), 8.21 (d, J=8.5 Hz, 1H), 8.46 (t, J=5.3 Hz, 1H), 9.01 (t, J=2.3 Hz, 1H). LC-MS: 3.84 min. (M+H)=559.9.

Example 4

N-(4-{1-[3-(3,5-DICHLOROPHENYL)-5-QUINOXALIN-6-YL-1H-PYRAZOL-1-YL]ETHYL}BENZOYL)-β-ALANINE-ISOMER 2

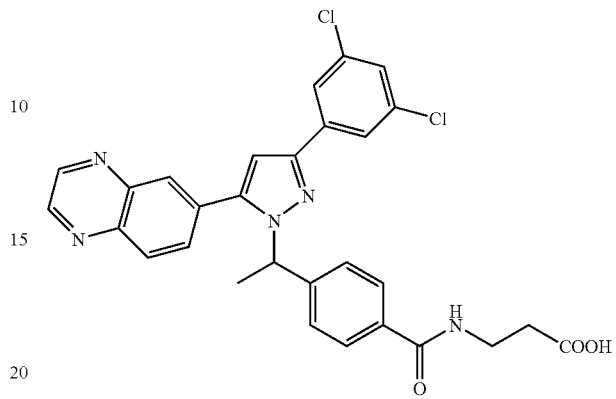

To a solution of isomer B from example 3 step H (14.7 mg, 0.02 mmol) in 2 mL of THF was added sodium hydroxide (5N, 1.5 mL, 7.5 mmol) followed by methanol (2.5 mL). The reaction was stirred at room temperature overnight and then concentrated in vacuo to remove THF/MeOH. The resulting aqueous mixture was acidified with 1N HCl until the pH was slightly acidic (pH=5). The resulting solution was extracted with EtOAc (3×), and the combined organic layers were then washed with brine, dried over anhydrous MgSO$_4$, filtered and concentrated in vacuo. The resulting light yellow solid was dissolved in 1,4-dioxane and lyophilized overnight to afford the product as a white solid. $^1$H NMR (DMSO, 500 MHz): 1.92 (d, J=6.9 Hz, 3H), 2.2 (m, 2H), 3.15 (m, 2H), 5.84 (q, J=6.8 Hz, 1H), 7.22 (d, J=8.4 Hz, 2H), 7.34 (s, 1H), 7.59 (t, J=1.8 Hz, 1H), 7.73 (d, J=8.2 Hz, 2H), 7.88 (dd, J=8.7, 1.9 Hz, 1H), 7.96 (d, 1.8, 1H), 8.07 (d, J=1.9 Hz, 1H), 8.21 (d, J=8.5 Hz, 1H), 8.46 (t, J=5.3 Hz, 1H), 9.01 (s, 1H). LC-MS: 3.84 min. (M+H)=559.9.

Example 5

N-(4-{(1S)-1-[3-[2-CHLORO-5-(TRIFLUOROMETHYL)PHENYL]-5-(7-METHOXYQUINOLIN-3-YL)-1H-PYRAZOL-1-YL]ETHYL}BENZOYL)-β-ALANINE

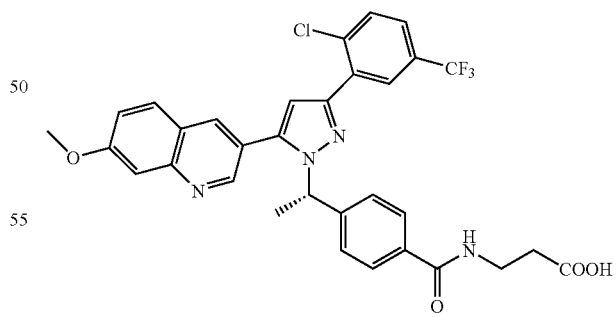

Step A

{[2-chloro-5-(trifluoromethyl)phenyl]ethynyl}(trimethyl)silane

To a solution of 1-bromo-2-chloro 4-(trifluoromethyl)benzene (1.5 mL, 10 mmol) in 30 mL of anhydrous THF was added Pd(PPh$_3$)$_2$Cl$_2$ (351 mg, 0.5 mmol), triphenylphosphine (65 mg, 0.25 mmol), ethynyl(trimethyl)silane (2.12 mL, 15 mmol), and triethylamine (2.1 mL, 15 mmol). The reaction was stirred at room temperature for 20 minutes after which CuI (23 mg, 0.12 mmol) was added to the solution and the reaction was stirred at room temperature for 16 hours. The reaction was then concentrated in vacuo and the resulting residue was dissolved in hexanes, filtered through Celite and again concentrated in vacuo. The residue was purified by flash column chromatography using 100% hexanes to afford the desired product as a dark brown oil. $^1$H NMR (CDCl$_3$, 500 MHz: 7.8 (d, J=1.6 Hz, 1H), 7.5 (m, 2H), 0.23 (s, 9H).

Step B 1-chloro-2-ethynyl-4-(trifluoromethyl)benzene

To a solution of the intermediate from step A (2.7 g, 10 mmol) in 10:1 MeOH:H$_2$O (60 mL) was added potassium carbonate (2.76 g, 20 mmol). The reaction was stirred at room temperature for 15 minutes after which the mixture was poured into a pH 7-phosphate buffer and extracted with methylene chloride (3×). The combined organic layers were then dried over anhydrous MgSO$_4$, filtered and concentrated in vacuo. The resulting oil was used without further purification. $^1$H NMR (CDCl$_3$, 500 MHz): 7.8 (d, J=1.9 Hz, 1H), 7.5 (m, 2H), 3.48 (s, 1H).

Step C

3-[2-chloro-5-(trifluoromethyl)phenyl]-1-(7-methoxyquinolin-3-yl)prop-2-yn-1-one The title compound was prepared with the alkyne from step B and N,7-dimethoxy-N-methylquinoline-3-carboxamide the intermediate from example 2 step E following the procedure described in example 2 step F. $^1$H NMR (CDCl$_3$, 500 MHz): 9.62 (d, J=2.1 Hz, 1H), 8.97 (d, J=2.1 Hz, 1H), 8.03 (s, 1H), 7.87 (d, J=8.9 Hz, 1H), 7.69 (d, J=3.0 Hz, 2H), 7.51 (d, J=2.3 Hz, 1H), 7.31 (dd, J=2.3, 8.9 Hz, 1H), 4.03 (s, 3H). LC-MS: 3.85 min. (M+H)=389.9.

Step D

N-(4-{(1S)-1-[3-[2-chloro-5-(trifluoromethyl)phenyl]-5-(7-methoxyquinolin-3-yl)-1H-pyrazol-1-yl]ethyl}benzoyl)-β-alanine The title compound was prepared following the procedure described in example 2 steps G-J. $^1$H NMR (CD$_3$OD, 500 MHz): 8.76 (d, J=1.8 Hz, 1H), 8.48 (d, J=1.7 Hz, 1H), 8.21 (d, J=1.7 Hz, 1H), 7.96 (m, 5H), 7.44 (m, 2H), 7.21 (d, J=8.3 Hz, 2H), 7.16 (s, 1H), 5.76 (q, J=6.9 Hz, 1H), 4.02 (s, 3H), 3.55 (t, J=6.9 Hz, 2H), 2.6 (t, J=6.9 Hz, 2H), 1.98 (d, J=6.9 Hz, 3H). LC-MS: 3.35 min. (M+H)=623.0.

Example 6

N-[4-({3-(3,4-DICHLOROPHENYL)-5-[7-(TRIFLUOROMETHYL)QUINOLIN-3-YL]-1H-PYRAZOL-1-YL}METHYL)BENZOYL]-β-ALANINE

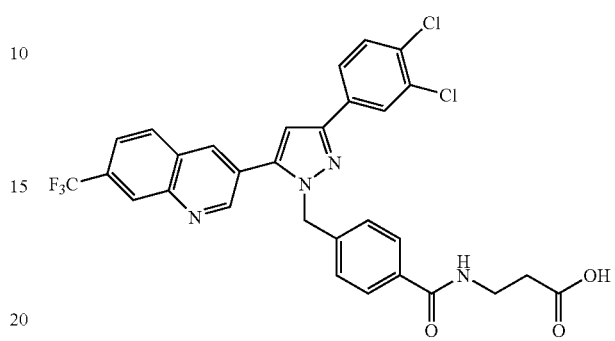

Step A 1,2-dichloro-4-ethynylbenzene

This intermediate was prepared from 3,4-dichloro-iodobenzene by following the procedure described in example 1 step A. $^1$H NMR (CDCl$_3$, 500 MHz): 7.6 (d, J=2.8 Hz, 1H), 7.43 (d, J=8.2 Hz, 1H), 7.34 (dd, J=1.9, 8.4 Hz, 1H), 3.2 (s, 1H).

Step B

N-methoxy-N-methyl-6-(trifluoromethyl)-2-naphthamide

This intermediate was prepared from ethyl 4-hydroxy-7-(trifluoromethyl)quinoline-3-carboxylate using the procedure described in example 2 steps B-E. $^1$H NMR (CDCl$_3$, 500 MHz): 3.49 (s, 3H), 3.60 (s, 3H), 7.80 (d, J=8.5 Hz, 1H), 8.05 (d, J=8.5 Hz, 1H), 8.47 (s, 1H), 8.64 (d, J=1.6 Hz, 1H), 9.32 (d, J=2.0 Hz, 1H). LC-MS: 1.11 min. (M+H)=111.

Step C 3-(3,4-dichlorophenyl)-1-[7-(trifluoromethyl)quinolin-3-yl]prop-2-yn-1-one This intermediate was prepared using the alkyne from step A and the amide from step B by following the procedure described in example 2 step F. $^1$H NMR (CDCl$_3$, 500 MHz): 7.60 (s, 2H), 7.87 (s, 1H), 7.89 (d, J=9.8 Hz, 1H), 8.20 (d, J=8.5 Hz, 1H), 8.55 (s, 1H), 9.02 (d, J=2.3 Hz, 1H), 9.73 (d, J=2.1 Hz, 1H).

Step D ethyl 4-({3-(3,4-dichlorophenyl)-5-[7-(trifluoromethyl)quinolin-3-yl]-1H-pyrazol-1-yl}methyl)benzoate To a solution of the intermediate from step C (40 mg, 0.10 mmol) in 3 mL of anhydrous DMF was added methyl 4-(hydrazinomethyl)benzoate hydrochloride (26 mg, 0.12 mmol) followed by triethylamine (0.02 mL, 0.12 mmol). The reaction was stirred at room temperature overnight after which the reaction was quenched with water and extracted with EtOAc (3×). The combined organic layers were washed with brine, dried over anhydrous MgSO$_4$, filtered and concentrated in vacuo. The resulting solid was purified by flash chromatography (15% EtOAc/Hexanes) to afford a light yellow solid. This material was re-purified by flash chromatography (100% CH$_2$Cl$_2$) to give two pyrazole isomers that were assigned by no difference spectroscopy. Isomer A: $^1$H NMR (CDCl$_3$, 500 MHz): 3.92 (s, 3H), 5.52 (s, 3H), 6.87 (s, 1H), 7.20 (d, J=8.2 Hz, 2H), 7.52 (d, J=8.3 Hz, 2H), 7.74 (dd, J=8.4, 1.7 Hz, 1H), 7.79 (d, J=8.7 Hz, 1H), 7.88 (d, J=8.7 Hz, 1H), 8.01 (d, J=8.1 Hz, 3H), 8.09 (d, J=1.8 Hz, 1H), 8.47 (s, 1H), 9.01 (d, J=1.8 Hz, 1H). LC-MS: 4.71 min. (M+H)=555.99. Isomer B: $^1$H NMR (CDCl$_3$, 500 MHz): 3.94 (s, 3H), 5.50 (s, 3H), 6.91 (s, 1H), 7.18 (dd, J=8.3, 2.1 Hz, 1H), 7.23 (d, J=8.3 Hz, 2H), 7.48 (d, J=2.1 Hz, 1H), 7.52 (d, J=8.2 Hz, 1H), 7.76 (dd, J=8.7, 1.1 Hz, 1H), 8.03 (m, 3H), 8.46 (s, 1H), 8.64 (d, J=1.8 Hz, 1H), 9.54 (d, J=2.0 Hz, 1H). LC-MS: 4.61 min. (M+H)=555.99.

Step E

N-[4-({3-(3,4-dichlorophenyl)-5-[7-(trifluoromethyl) quinolin-3-yl]-1H-pyrazol-1-yl}methyl)benzoyl]-β-alanine The title compound was prepared using the isomer A from step D following the procedure described for example 2 steps H-J. $^1$H NMR (DMSO, 500 MHz): 2.46 (t, J=7.1 Hz, 2H), 3.40 (q, J=6.9 Hz, 2H), 5.68 (s, 2H), 7.13 (d, J=8.2 Hz, 2H), 7.44 (s, 1H), 7.72 (m, 2H), 7.89 (dd, J=8.4, 1.9 Hz, 1H), 7.96 (d, J=8.3 Hz, 1H), 8.12 (d, J=1.9 Hz, 1H), 8.25 (d, J=8.2 Hz, 1H), 8.42 (s, 1H), 8.44 (t, J=5.3 Hz, 1H), 8.68 (d, J=2.0 Hz, 1H), 9.14 (d, J=2.3 Hz, 1H). LC-MS: 3.95 min. (M+H)=613.27.

Example 8

N-(4-{(1S)-1-[3-(3,5-DICHLOROPHENYL)-5-(6-METHOXYQUINOLIN-2-YL)-1H-PYRAZOL-1-YL]ETHYL}BENZOYL)-β-ALANINE

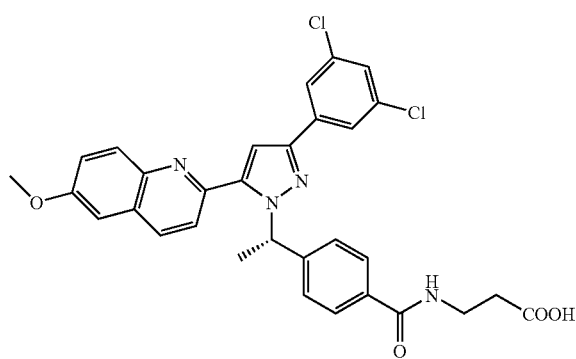

Step A

Ethyl 4-hydroxy-6-methoxyquinoline-2-carboxylate

To a solution of p-anisidine (2.7 g, 22 mmol) in methanol (50 mL) was added diethyl-acetylene dicarboxylate (3.74 g, 22 mmol). The resulting solution was heated at 55° C. for 1 hour. The reaction mixture was concentrated in vacuo. The residue was dissolved in phenyl ether (40 mL) and refluxed at 240° C. for 1 hour. The reaction mixture was cooled to room temperature, diluted with hexanes and filtered. A light brown solid was obtained. LC-MS: 1.39 min; (M+H)=248.1.

Step B

Ethyl 4-chloro-6-methoxyquinoline-2-carboxylate

This intermediate was prepared using the ester from step A by following the procedure described in example 2 step B. $^1$H NMR (CDCl$_3$, 500 MHz): 8.24 (s, 1H), 8.2 (d, J=8.9 Hz, 1H), 7.47 (dd, J=2.8, 9.1 Hz, 1H), 7.44 (t, J=2.7 Hz, 1H), 4.55 (q, J=7.1 Hz, 2H), 4.0 (s, 3H), 1.5 (t, J=7.1 Hz, 3H). LC-MS: 3.42 min; (M+H)=266.3.

Step C

N,6-dimethoxy-N-methylquinoline-2-carboxamide

This compound was prepared from the intermediate in step B using the procedure described in example 2 steps C-E. $^1$H NMR (CDCl$_3$, 500 MHz): 8.17 (d, J=8.5 Hz, 1H), 8.07 (d, J=9.2 Hz, 1H), 7.74 (bs, 1H), 7.45 (dd, J=2.7, 9.1 Hz, 1H), 7.14 (d, J=2.7 Hz, 1H), 3.98 (s, 3H), 3.85 (bs, 3H), 3.51 (bs, 3H). LC-MS: 2.44 min; (M+H)=247.4

Step D 3-(3,5-dichlorophenyl)-1-(6-methoxyquinolin-2-yl) prop-2-yn-1-one

This compound was prepared using the alkyne from example 1 step B and the amide from step C by following the procedure described in example 2 step F. $^1$H NMR (CDCl$_3$, 500 MHz): 8.26 (d, J=9.4 Hz, 1H), 8.21 (s, 1H), 7.67 (d, J=1.9 Hz, 2H), 7.5 (m, 2H), 7.4 (m, 1H), 7.17 (d, J=2.8 Hz, 1H), 4.02 (s, 3H). LC-MS: 4.35 min; (M+H)=356.2.

Step E

Ethyl 4-{(1S)-1-[3-(3,5-dichlorophenyl)-5-(6-methoxyquinolin-2-yl)-1H-pyrazol-1-yl]ethyl}benzoate This compound was prepared using the intermediate from step D by following the procedure described in example 2 step G. $^1$H NMR (CDCl$_3$, 500 MHz): 8.1 (d, J=8.7 Hz, 1H), 8.02 (d, J=9.2 Hz, 1H), 7.97 (d, J=8.2 Hz, 2H), 7.84 (d, J=1.8 Hz, 2H), 7.63 (d, J=8.5 Hz, 1H), 7.46 (dd, J=2.7, 9.4 Hz, 1H), 7.44 (d, J=8.5 Hz, 2H), 7.35 (t, J=1.8 Hz, 1H), 7.16 (q, J=7.1 Hz, 1H), 7.11 (d, J=2.7 Hz, 1H), 7.02 (s, 1H), 4.38 (q, J=7.1 Hz, 2H), 3.99 (s, 3H), 2.1 (s, J=7.1 Hz, 3H), 1.39 (t, J=7.0 Hz, 3H). LC-MS: 4.85 min (M+H)=496.0.

Step F

N-(4-{(1S)-1-[3-(3,5-dichlorophenyl)-5-(6-methoxyquinolin-2-yl)-1H-pyrazol-1-yl]ethyl}benzoyl)-β-alanine The title compound was prepared using the intermediate from step E by following the procedure described in example 2 steps H-J. $^1$H NMR (DMSO, 500 MHz): 8.42 (t, J=5.3 Hz, 1H), 8.37 (d, J=8.9 Hz, 1H), 8.03 (d, J=9.1 Hz, 1H), 7.97 (d, J=1.8 Hz, 2H), 7.91 (d, J=8.7 Hz, 1H), 7.76 (s, 1H), 7.69 (m, 2H), 7.60 (t, J=1.8 Hz, 1H), 7.47 (dd, J=2.7, 9.1 Hz, 1H), 7.4

(m, 3H), 7.3 (q, J=7.1 Hz, 1H), 3.92 (s, 3H), 3.4 (q, J=7.1 Hz, 2H), 2.46 (t, J=7.1 Hz, 2H), 1.98 (t, J=6.9 Hz, 3H). LC-MS: 2.81 min; (M+H)=589.2.

The following examples in Table I can be synthesized according to the procedures described above for Examples 1-8.

TABLE 1

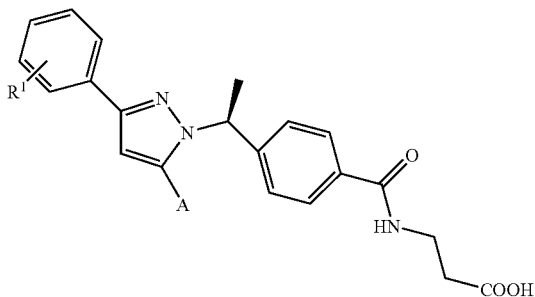

| Example | A | R¹ | LC-MS, min. (M + H) |
|---|---|---|---|
| 9 | isoquinolin-3-yl | 3,5-dichloro | 4.11 min; 559.0 |
| 10 | quinolin-2-yl | 3,5-dichloro | 4.23 min; 558.9 |
| 11 | quinoxalin-2-yl | 3,5-dichloro | 4.11 min; 559.9 |
| 12 | quinoxalin-2-yl | 2Cl-5-CF₃ | 3.96 min; 594.13 |
| 13 | quinolin-6-yl | 3,5-dichloro | 3.39 min; 558.9 |
| 14 | 7-CF₃-quinolin-3-yl | 3,5-dichloro | 4.21 min; 626.9 |
| 15 | 6-OCF₃-quinolin-3-yl | 3,5-dichloro | 4.20 min; 642.9 |

TABLE 1-continued
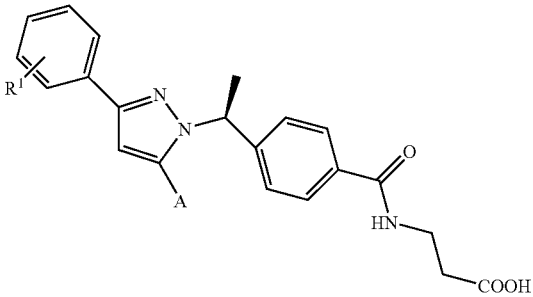
| Example | A | R¹ | LC-MS, min. (M + H) |
|---|---|---|---|
| 16 | 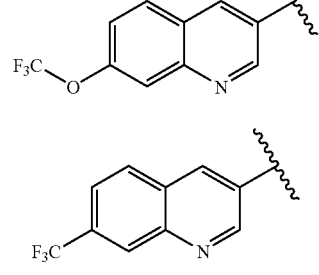 | 3,5-dichloro | 4.14 min; 642.9 |
| 17 | 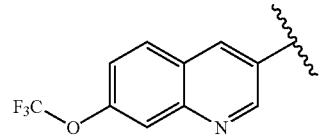 | 2F-5-CF₃ | 4.01 min; 645.5 |
| 18 | 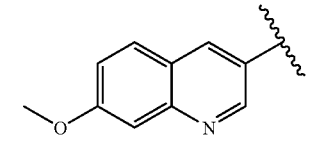 | 2F-5-CF₃ | 4.03 min; 661.0 |
| 19 | 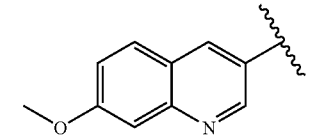 | 2F-5-CF₃ | 3.37 min; 606.8 |
| 20 | 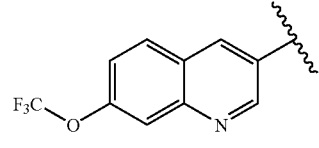 | 3,4-dichloro | 3.44 min; 589.1 |
| 21 | 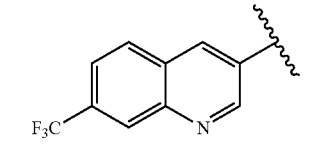 | 3,4-dichloro | 4.18 min; 643.2 |
| 22 | 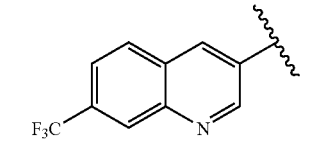 | 3,4-dichloro | 4.08 min; 626.9 |
| 23 | | 2F-4-CF₃ | 4.09 min; 645.5 |

TABLE 1-continued

| Example | A | R¹ | LC-MS, min. (M + H) |
|---------|---|----|----|
| 24 | 7-CF₃-quinolin-3-yl | 2Cl-5-CF₃ | 4.10 min; 661.9 |
| 25 | 8-F-7-CF₃-quinolin-3-yl | 3,5-dichloro | 4.20 min; 646.4 |
| 26 | 8-OMe-7-CF₃-quinolin-3-yl | 3,5-dichloro | 4.28 min; 658.5 |
| 27 | 7-Cl-quinolin-3-yl | 3,5-dichloro | 4.17 min; 593.3 |
| 28 | 7-Cl-quinolin-3-yl | 3,4-dichloro | 4.09 min; 593.3 |
| 29 | 7-Cl-quinolin-3-yl | 2F-4-CF₃ | 4.05 min; 611.4 |
| 30 | 6,7,8-trifluoroquinolin-3-yl | 3,5-dichloro | 2.56 min; 613.4 |

TABLE 1-continued
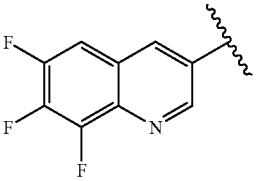
| Example | A | R¹ | LC-MS, min. (M + H) |
|---|---|---|---|
| 31 | 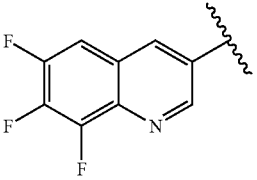 | 3,4-dichloro | 2.51 min; 613.1 |
| 32 | 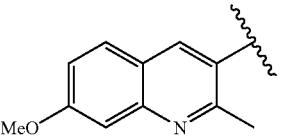 | 2Cl-5-CF₃ | 2.49 min; 647.2 |
| 33 | 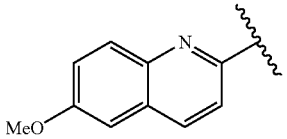 | 3,5-dichloro | 2.26 min; 603.2 |
| 34 | 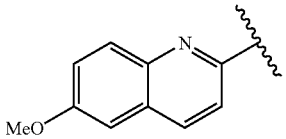 | 2-F-4-CF₃ | 2.73 min; 607.2 |
| 35 | 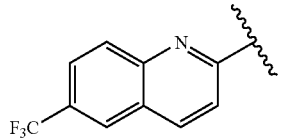 | 2-Cl-5-CF₃ | 4.26 min; 623.1 |
| 36 | 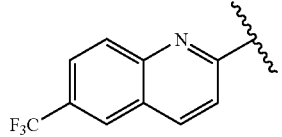 | 3,5-dichloro | 4.37 min; 627.1 |
| 37 | 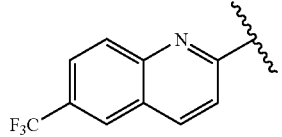 | 2-F-4-CF₃ | 4.27 min; 645.01 |

TABLE 1-continued

| Example | A | R¹ | LC-MS, min. (M + H) |
|---|---|---|---|
| 38 | 6-(trifluoromethyl)quinolin-2-yl | 2-Cl-5-CF₃ | 4.28 min; 661.1 |
| 39 | 6-(trifluoromethoxy)quinolin-2-yl | 3,5-dichloro | 4.47 min; 644.95 |
| 40 | 6-(trifluoromethoxy)quinolin-2-yl | 3,4-dichloro | 4.39 min; 644.96 |
| 41 | 6-(trifluoromethoxy)quinolin-2-yl | 2-Cl-5-CF₃ | 4.35 min; 677.1 |

Example 42

N-[4-({3-(3,5-DICHLOROPHENYL)-5-[6-(TRIFLUOROMETHOXY)-1H-BENZIMIDAZOL-2-YL]-H-PYRAZOL-1-YL}METHYL)BENZOYL]-β-ALANINE

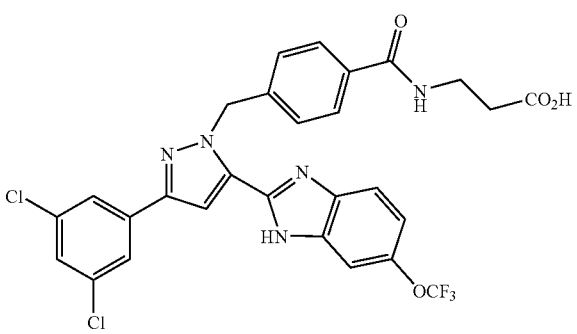

Step A

Methyl 4-({3-(3,5-dichlorophenyl)-5-[6-(trifluoromethoxy)-1H-benzimidazol-2-yl]-1H-pyrazol-1-yl}methyl)benzoate 3-(3,5-Dichlorophenyl)-1-[4-(methoxycarbonyl)benzyl]-1H-pyrazole-5-carboxylic acid (36.7 mg, 91 umol), 4-(trifluoromethoxy)benzen-1,2-diamine (52 mg, 3 eq.), DIEA (25 ul, 1.5 eq.) were dissolved in DMF (0.7 ml). A solution of PyBOP (66 mg, 1.4 eq.) in DMF (0.2 ml) was added. The mixture was stirred for 30 min, and quenched with CH₃CN:water (5% TFA), and purified with reverse phase HPLC. The product was collected and lyophilized to give a solid amide as a mixture of two isomers. MS cald for C₂₆H₁₉Cl₂F₃N₄O₄: 578.07; Obsd (M+1): 579.09. This amides were refluxed in acetic acid (10 ml) for 1 hr to methyl 4-({3-(3,5-dichlorophenyl)-5-[6-(trifluoromethoxy)-1H-benzimidazol-2-yl]-1H-pyrazol-1-yl}methyl)benzoate as a white solid after lyophilization. MS Cald for C₂₆H₁₇Cl₂F₃N₄O₃: 560.06; Obsd (M+1): 561.14.

Step B 4-({3-(3,5-Dichlorophenyl)-5-[6-(trifluoromethoxy)-1H-benzimidazol-2-yl]-1H-pyrazol-1-yl}methyl)benzoic acid Methyl 4-({3-(3,5-dichlorophenyl)-5-[6-(trifluoromethoxy)-1H-benzimidazol-2-yl]-1H-pyrazol-1-yl}methyl)benzoate (45 mg, 82 umol) was dissolved in dioxane:methanol (1:1, 1.6 ml), and treated with a solution of NaOH (40 mg in 0.4 ml). The reaction was heated to 65° C. for 1 hr. The mixture was acidified with 5% TFA in CH3CN. The mixture was evaporated to dryness, and the residue dissolved in DMF:water (10:1), and purified with reverse phase HPLC to give, after lyophilization, 4-({3-(3,5-dichlorophenyl)-5-[6-(trifluoromethoxy)-1H-benzimidazol-2-yl]-1H-pyrazol-1-yl}methyl)benzoic acid as a white powder.

Step C

N-[4-({3-(3,5-Dichlorophenyl)-5-[6-(trifluoromethoxy)-1H-benzimidazol-2-yl]-1H-pyrazol-1-yl}methyl)benzoyl]-β-alanine A solution of PyBOP (38 mg, 70 umol) in DMF (0.1 ml) was added to a mixture of 4-({3-(3,5-dichlorophenyl)-5-[6-(trifluoromethoxy)-1H-benzimidazol-2-yl]-1H-pyrazol-1-yl}methyl)benzoic acid (20 mg, 36 umol), tert-butyl β-alanine hydrochloride (27 mg, 4 eq.), DIEA (40 ul, 6 eq.) in DMF (0.3 ml). The reaction was quenched with CH$_3$CN:water (5% TFA) and purified with reverse phase HPLC to give tert-butyl N-[4-({3-(3,5-dichlorophenyl)-5-[6-(trifluoromethoxy)-1H-benzimidazol-2-yl]-1H-pyrazol-1-yl}methyl)benzoyl]-β-alaninate as an oil residue. This was treated with TFA/DCM (1:2) and the product was lyophilized to give N-[4-({3-(3,5-Dichlorophenyl)-5-[6-(trifluoromethoxy)-1H-benzimidazol-2-yl]-1H-pyrazol-1-yl}methyl)benzoyl]-β-alanine as a white powder. NMR (500 MHz, DMSO-d$_6$) δ: 2.43 (t, 2H); 3.4 (q, 2H); 6.18 (s, 2H); 7.26 (br d, J=9.2 Hz, 1H); 7.38 (d, J=8.5 Hz, 2H); 7.59 (s, 1H); 7.61 (t, J=1.9 Hz, 1H); 7.67 (br s, 1H); 7.72 (d, J=8.5 Hz, 2H); 7.74 (br d, J=9.2 Hz, 1H); 7.82 (d, J=1.9 Hz, 2H). MS Cald for C$_{28}$H$_{20}$Cl$_2$F$_3$N$_5$O$_4$: 617.08; Obsd (M+1): 618.21.

Example 43

N-[4-({3-(3,5-DICHLOROPHENYL)-5-[5-(TRIFLUOROMETHYL)-1H-BENZIMIDAZOL-2-YL]-1H-PYRAZOL-1-YL}METHYL)BENZOYL]-β-ALANINE

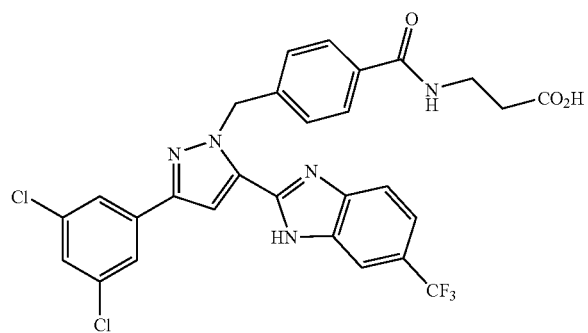

This compound was made in the same manner as the compound described in Example 42 above. $^1$H NMR (500 MHz, CD$_3$OD) δ: 7.98 (s, 1H); 7.87 (d, J=1.8 Hz, 2H); 7.79 (d, J=8.5 Hz, 1H); 7.71 (d, J=8.3 Hz, 2H); 7.59 (dd, J=1.4, 8.5 Hz, 1H); 7.45 (m, 1H); 7.39 (m, 3H); 6.23 (s, 2H); 3.59 (t, J=7.1 Hz, 2H); 2.60 (t, J=7.1 Hz, 2H). HPLC/MS Calcd.: 601.09. Found: 601.90.

Example 44

N-[4-({3-(3,5-DICHLOROPHENYL)-5-[1-METHYL-5-(TRIFLUOROMETHYL)-1H-BENZIMIDAZOL-2-YL]-1H-PYRAZOL-1-YL}METHYL)BENZOYL]-β-ALANINE AND N-[4-({3-(3,5-DICHLOROPHENYL)-5-[1-METHYL-6-(TRIFLUOROMETHYL)-1H-BENZIMIDAZOL-2-YL]-1H-PYRAZOL-1-YL}METHYL)BENZOYL]-β-ALANINE

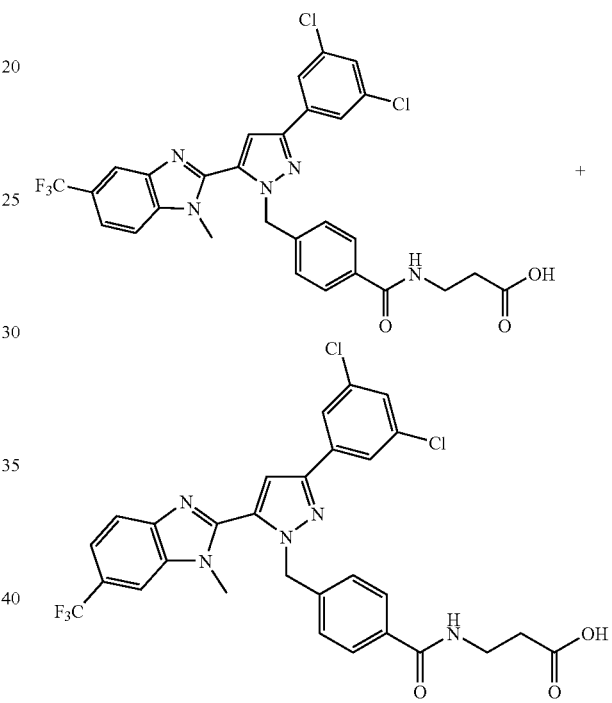

To a solution of N-[4-({3-(3,5-dichlorophenyl)-5-[5-(trifluoromethyl)-1H-benzimidazol-2-yl]-1H-pyrazol-1-yl}methyl)benzoyl]-β-alanine (8 mg, 0.011 mmol) in 1 mL of N,N-dimethylformamide was added cesium carbonate (16 mg, 0.048 mmol) and iodomethane (5 mL, 0.063 mmol). The resultant mixture was stirred at ambient temperature for 4 h, diluted with ethyl acetate, and washed successively with four portions of water and one portion of brine. The organic layer was dried over magnesium sulfate, concentrated in vacuo and the residue suspended in 1 mL of tetrahydrofuran and 1 mL of water. Lithium hydroxide (5 mg, 0.12 mmol) was added and the mixture stirred at ambient temperature for 48 hours. The mixture was diluted with ethyl acetate and water and acidified with 1N hydrochloric acid. The organic phase was washed with brine, dried over magnesium sulfate, and concentrated in vacuo. The residue was purified by reverse phase preparative HPLC to provide the title compounds as a mixture of regioisomers. $^1$H NMR (500 MHz, CD$_3$OD) δ: 8.09 (s, 1H); 7.95 (m, 4H); 7.76-7.62 (m, 10H); 7.46 (m, 1H); 7.41 (s, 2H); 7.16 (d, J=7.4 Hz, 4H); 5.85 (s, 4H); 3.79 (s, 3H); 3.77 (s, 3H); 3.58 (t, J=6.8 Hz, 4H); 2.61 (t, J=6.8 Hz, 4H). Calcd.: 615.11. Found: 615.88.

Example 45

N-[4-({3-(3,5-DICHLOROPHENYL)-5-[1-ME-THYL-5-(TRIFLUOROMETHOXY)-1H-BENZ-IMIDAZOL-2-YL]-1H-PYRAZOL-1-YL}METHYL)BENZOYL]-β-ALANINE AND N-[4-({3-(3,5-DICHLOROPHENYL)-5-[1-METHYL-6-(TRIFLUOROMETHOXY)-1H-BENZIMIDAZOL-2-YL]-1H-PYRAZOL-1-YL}METHYL)BENZOYL]-β-ALANINE

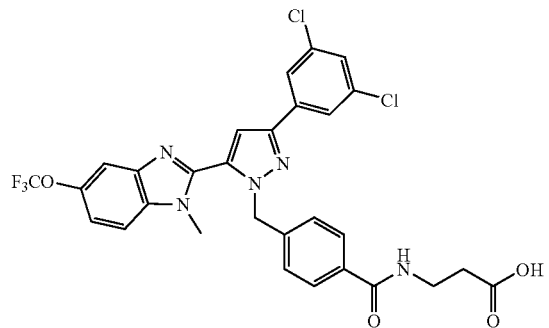

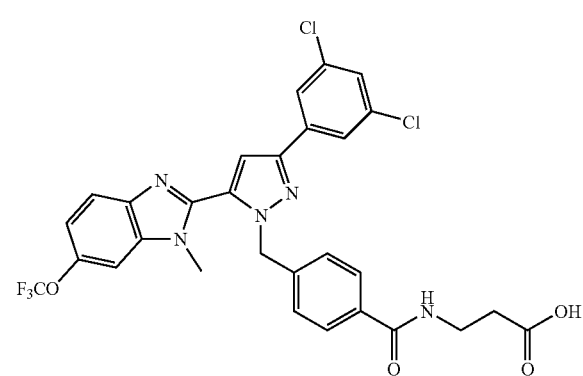

These compounds were made in the same manner as the compounds described in Example 44. $^1$H NMR (500 MHz, CD$_3$OD) δ: 7.93 (m, 6H); 7.84 (d, J=8.7 Hz, 1H); 7.69-7.62 (m, 6H); 7.45 (m, 1H); 7.38-7.30 (m, 4H); 7.14 (d, J=8.3 Hz, 4H); 5.82 (s, 2H); 5.81 (s, 2H); 3.73 (s, 3H); 3.72 (s, 3H); 3.59 (t, J=6.9 Hz, 4H); 2.61 (t, J=6.9 Hz, 4H). HPLC/MS Calcd.: 631.10. Found: 631.93.

Example 46

N-(4-{[3-(3,5-DICHLOROPHENYL)-5-(5,6-DIFLUORO-1,3-BENZOXAZOL-2-YL)-1H-PYRAZOL-1-YL]METHYL}BENZOYL)-β-ALANINE

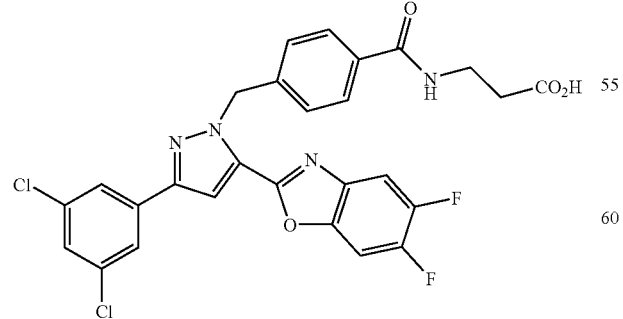

3-(3,5-Dichlorophenyl)-1-[4-(methoxycarbonyl)benzyl]-1H-pyrazole-5-carboxylic acid (15.5 mg, 38 umol), 2-amino-4,5-difluorophenol (16 mg, 3 eq.), and DIEA (10 ul, 1.5 eq.) were dissolved in DMF (450 ul). A solution of PyBOP (24 mg, 1.2 eq.) in DMF (150 ul) was added dropwise. After 30 min, the reaction mixture was quenched with CH$_3$CN:H$_2$O (5% TFA) and injected to reverse phase HPLC to give, after lyophilization, methyl 4-[(3-(3,5-dichlorophenyl)-5-{[(4,5-difluoro-2-hydroxyphenyl)amino]carbonyl}-1H-pyrazol-1-yl)methyl]benzoate as a white powder.

Methyl 4-[(3-(3,5-dichlorophenyl)-5-{[(4,5-difluoro-2-hydroxyphenyl)amino]carbonyl}-1H-pyrazol-1-yl)methyl] benzoate (6.7 mg) was dissolved in MeOH-dioxane (1:1, 800 ul). A solution of NaOH (20 mg, 200 ul) was added. After 1 hr, the mixture was acidified with 5% TFA in CH$_3$CN:H$_2$O and purified via reverse phase HPLC to give, after lyophilization, 4-[(3-(3,5-dichlorophenyl)-5-{[(4,5-difluoro-2-hydroxyphenyl)-amino]carbonyl}-1H-pyrazol-1-yl)methyl]benzoic acid as a white powder.

The above acid was dissolved in DMF (200 ul) containing t-butyl beta-alanine hydrochloride (6.5 mg, 4 eq.), DIEA (7 ul, 4 eq.) and PyBOP (5.7 mg, 1.5 eq.). The reaction was quenched after 1 hr with CH$_3$CN:H2O (5% TFA) and purified through reverse phase HPLC to give, after lyophilization, tert-butyl N-{4-[(3-(3,5-dichlorophenyl)-5-{[(4,5-difluoro-2-hydroxyphenyl)-amino]carbonyl}-1H-pyrazol-1-yl)methyl]benzoyl}-β-alaninate as a white powder.

tert-Butyl N-{4-[(3-(3,5-dichlorophenyl)-5-{[(4,5-difluoro-2-hydroxyphenyl)-amino]-carbonyl}-1H-pyrazol-1-yl)methyl]benzoyl}-β-alaninate (6 mg) was heated in HOAc (0.5 ml) to 200 C in microwave oven for 3 hr. The mixture was diluted with CH$_3$CN:H$_2$O and purified through reverse phase HPLC to give, after lyophilization, N-(4-{[3-(3,5-dichlorophenyl)-5-(5,6-difluoro-1,3-benzoxazol-2-yl)-1H-pyrazol-1-yl]methyl}benzoyl)-β-alanine as a white powder. MS Cald for C$_{27}$H$_{18}$Cl$_2$F$_2$N$_4$O$_4$: 570.07; Obsd: 571.15.

Example 47

N-(4-{[5-(1,3-BENZOTHIAZOL-2-YL)-3-(3,5-DICHLOROPHENYL)-1H-PYRAZOL-1-YL]METHYL}BENZOYL)-β-ALANINE

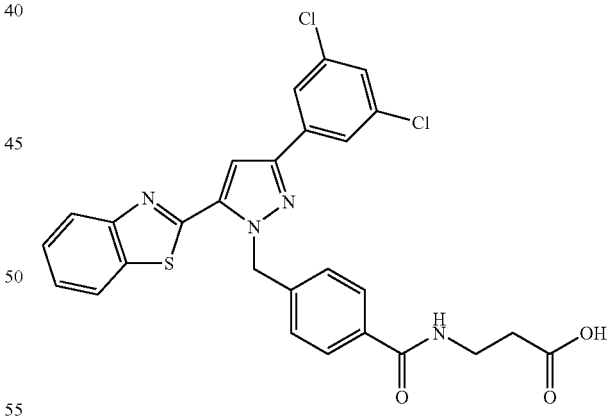

Step A

4-{[5-(1,3-benzothiazol-2-yl)-3-(3,5-dichlorophenyl)-1H-pyrazol-1-yl]methyl}-benzoic acid To a mixture of 3-(3,5-dichlorophenyl)-1-[4-(methoxycarbonyl)benzyl]-1H-pyrazole-5-carboxylic acid (20 mg, 0.049 mmol), and PyBOP (36 mg, 0.069 mmol) in 1 mL of N,N-dimethylformamide was added N,N-diisopropylethylamine (15 μL, 0.088 mmol). After stirring at ambient temperature for 10 min, 2-aminothiophenol (7 μL, 0.059 mmol) was added, and stirring continued for 1 h. The resultant mixture was added drop-wise to 10 mL of glacial acetic acid containing dithiothreitol (15 mg, 0.097 mmol), and the mixture heated at 110° C. for 1 h. The acetic acid was removed in vacuo, the residue suspended in ethyl acetate and the organic layer washed successively with two portions of aqueous saturated sodium bicarbonate solution and one portion of brine. The organic layer was dried over magnesium sulfate, concentrated in vacuo, and the residue suspended in 2 mL of dioxane and 1 mL of water. Lithium hydroxide monohydrate (42 mg, 1.02 mmol) was added and the mixture heated at 50° C. for 2 h. The mixture was diluted with ethyl acetate and water and acidified with 1N hydrochloric acid solution. The organic layer was washed with one portion of brine, dried over magnesium sulfate, and concentrated in vacuo to provide the title compound which was used without purification. HPLC/MS: m/z=479.91 (M+1).

Step B

N-(4-{[5-(1,3-benzothiazol-2-yl)-3-(3,5-dichlorophenyl)-1H-pyrazol-1-yl]methyl}benzoyl)-β-alanine To a solution of 23 mg (0.049 mmol) of the product from above in 1 mL of N,N-dimethylformamide was added N,N-diisopropylethylamine (68 µL, 0.39 mmol), β-alanine-tert-butyl ester (53 mg, 0.29 mmol), and pyBOP (51 mg, 0.098 mmol). The resultant solution was stirred at ambient temperature for 16 h, diluted with ethyl acetate, and washed successively with four portions of water and one portion of brine. The organic layer was dried over magnesium sulfate, and concentrated in vacuo. The residue was suspended in 1 mL of dichloromethane, and treated with 1 mL of trifluoroacetic acid at ambient temperature for 1.5 h. The mixture was concentrated in vacuo and purified by reverse phase preparative HPLC to provide the title compound as a white powder. $^1$H NMR (500 MHz, DMSO) δ: 8.47 (br t, 1H); 8.21 (d, J=7.8 Hz, 1H); 8.12 (d, J=8.3 Hz, 1H); 8.01 (d, J=2.0 Hz, 2H); 7.89 (s, 1H); 7.75 (d, J=8.3 Hz, 2H); 7.61 (m, 2H), 7.55 (m, 1H); 7.37 (d, J=8.5 Hz, 2H); 6.13 (s, 2H); 3.40 (m, 2H); 2.46 (t, J=7.1 Hz, 2H).

Example 48

N-(4-{[5-(6-CHLORO-1,3-BENZOTHIAZOL-2-YL)-3-(3,5-DICHLOROPHENYL)-1H-PYRAZOL-1-YL]METHYL}BENZOYL)-β-ALANINE

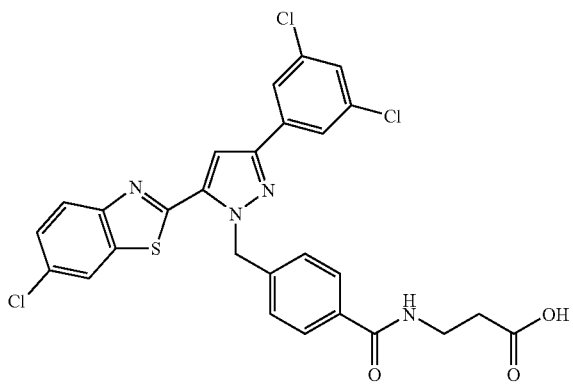

This compound was made in the same manner as the compound described in example 4 above. $^1$H NMR (500 MHz, DMSO) δ: 8.45 (t, J=5.5 Hz, 1H); 8.39 (d, J=2.3 Hz, 1H); 8.12 (d, J=8.7 Hz, 1H); 8.01 (d, J=1.9 Hz, 2H); 7.92 (s, 1H); 7.75 (d, J=8.2 Hz, 2H); 7.63 (m, 2H); 7.37 (d, J=8.3 Hz, 2H); 6.11 (s, 2H); 3.42 (m, 2H); 2.47 (t, J=7.1 Hz, 2H). HPLC/MS: Calcd.: 584.02. Found: 586.80.

Example 49

N-(4-{[5-(5-CHLORO-1,3-BENZOTHIAZOL-2-YL)-3-(3,5-DICHLOROPHENYL)-1H-PYRAZOL-1-YL]METHYL}BENZOYL)-β-ALANINE

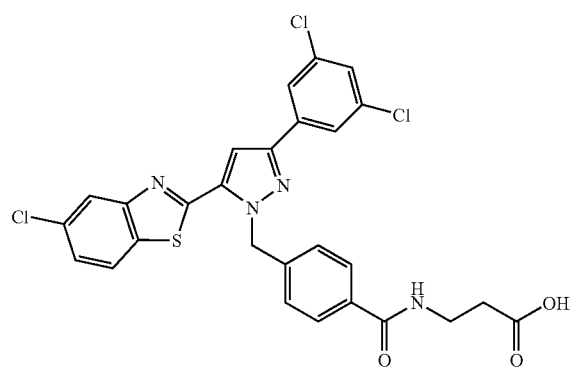

This compound was made in the same manner as the compound described in example 4 above. $^1$H NMR (500 MHz, DMSO) δ: 8.24 (m, 2H); 8.01 (d, J=1.8 Hz, 2H); 7.92 (s, 1H); 7.75 (d, J=8.5 Hz, 2H); 7.63 (t, J=1.8 Hz, 1H); 7.58 (dd, J=2.0, 8.7 Hz, 1H); 7.39 (d, J=8.2 Hz, 2H); 6.11 (s, 2H); 3.40 (t, J=7.1 Hz, 2H); 2.44 (t, J=7.1 Hz, 2H). HPLC/MS Calcd.: 584.02. Found: 586.78.

Example 50

N-[4-({3-(3,5-DICHLOROPHENYL)-5-[5-TRIFLUOUROMETHYL)-1,3-BENZOTHIAZOL-2-YL]-1H-PYRAZOL-1-YL}METHYL)BENZOYL]-β-ALANINE

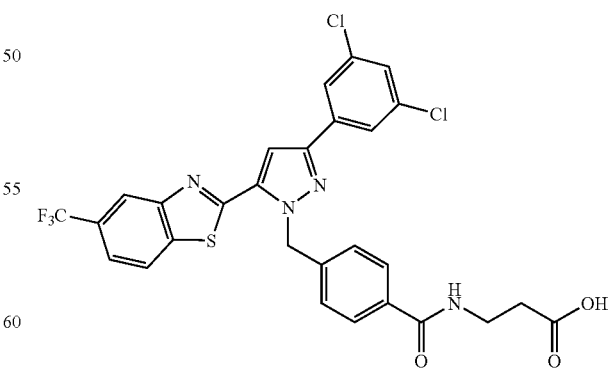

This compound was made in the same manner as the compound described in example 4 above. $^1$H NMR (500 MHz, DMSO) δ: 8.48 (m, 2H); 8.01 (d, J=1.8 Hz, 2H); 7.96 (s, 1H); 7.85 (d, J=8.4 Hz, 1H); 7.76 (d, J=8.3 Hz, 2H); 7.62 (m, 1H);

7.42 (d, J=8.2 Hz, 2H); 6.14 (s, 2H); 3.42 (m, 2H); 2.46 (d, J=7.1 Hz, 2H). HPLC/MS Calcd.: 618.05. Found: 618.84.

Example 51

N-(4-{[3-(3,5-DICHLOROPHENYL)-5-[6-METHOXY-1,3-BENZOTHIAZOL-2-YL]-1H-PYRAZOL-1-YL]METHYL}BENZOYL)-β-ALANINE

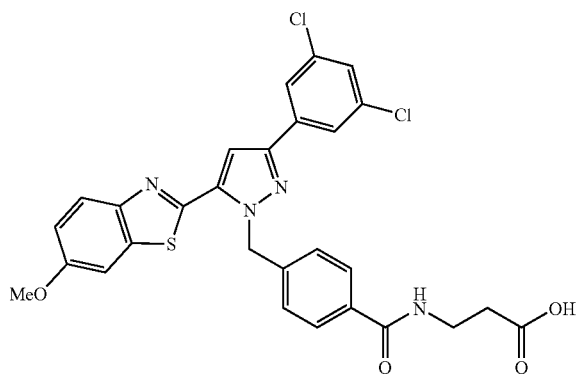

This compound was made in the same manner as the compound described in example 4 above. $^1$H NMR (500 MHz, DMSO) δ: 8.45 (t, J=5.5 Hz, 1H); 8.00 (m, 2H); 7.80 (m, 3H); 7.75 (d, J=8.2 Hz, 2H); 7.61 (d, J=1.9 Hz, 1H); 7.36 (d, J=8.2 Hz, 2H); 7.19 (dd, J=2.5 Hz, 8.9 Hz, 1H); 6.10 (s, 2H); 3.87 (s, 3H); 3.41 (m, 2H); 2.47 (t, J=7.1 Hz, 2H). HPLC/MS Calcd.: 580.07. Found: 580.87.

Example 52

N-(4-{(1S)-1-[5-(5-CHLORO-1H-INDOL-2-YL)-3-(3,5-DICHLOROPHENYL)-1H-PYRAZOL-1-YL]ETHYL}BENZOYL)-β-ALANINE

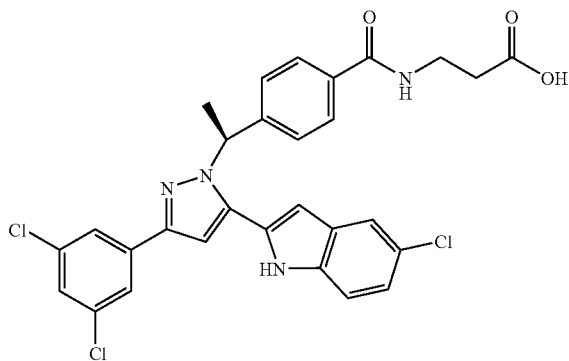

Step A Ethyl 4-{1-[3-(3,5-dichlorophenyl)-5-oxo-4,5-dihydro-1H-pyrazol-1-yl]ethyl}benzoate. A solution of ethyl (3,5-dichlorobenzoyl)acetate (3.0 g, 11.5 mmol) and {1-[4-(ethoxycarbonyl)phenyl]ethyl}hydrazinium chloride (2.55 g, 10.4 mmol) was refluxed in HOAc (80 ml) for 4 hr. The solvent was removed under reduced pressure, and the residue taken up with ethyl acetate, washed with sat. NaHCO$_3$ 2×, brine, and dried over Na$_2$SO$_4$. Flash column chromatography (SiO$_2$, 0-5% ethyl acetate in DCM gradient) gave ethyl 4-{1-[3-(3,5-dichlorophenyl)-5-oxo-4,5-dihydro-1H-pyrazol-1-yl]ethyl}benzoate as a white solid. TLC (5% ethyl acetate-DCM) R$_f$ 0.43. NMR (500 MHz, CDCl$_3$) δ: 1.38 (t, J=7.1 Hz, 3H); 1.78 (d, J=7.0 Hz, 3H); 3.55 (d, J=22.6 Hz, 1H); 3.60 (d, J=22.6 Hz, 1H); 4.36 (q, J=7.1 Hz, 2H); 5.57 (q, J=7.0 Hz, 1H); 7.39 (t, J=1.9 Hz, 1H); 7.50 (d, J=8.4 Hz, 2H). 7.52 (d, J=1.9 Hz, 2H); 8.02 (d, J=8.4 Hz, 2H). MS C$_{20}$H$_{18}$Cl$_2$N$_2$O$_3$ Cald: 404.07; Obsd (M+1): 405.20.

Step B tert-Butyl N-(4-{1-[3-(3,5-dichlorophenyl)-5-oxo-4,5-dihydro-1H-pyrazol-1-yl]ethyl}benzoyl)-β-alaninate. Ethyl 4-{1-[3-(3,5-dichlorophenyl)-5-oxo-4,5-dihydro-1H-pyrazol-1-yl]ethyl}benzoate (2.23 g, 5.50 mmol) was dissolved in MeOH-dioxane (1:1, 50 ml). A solution of NaOH (0.7 g/15 ml) was added. The mixture was heated to 60° C. for 1 hr. This was acidified with 2N HCl (10 ml), and the solvent was removed and residue vacuum dried to give a pale yellow solid (mixture of product acid and NaCl). This solid was suspended in DMF (15 ml), followed with DIEA (4.8 ml), beta-alanine t-butyl ester hydrochloride (3 g). A solution of PyBOP (3.43 g) in DMF (5 ml) was then added. After stirring at room temperature for 3 hr, more PyBOP (1 g) was added and the reaction mixture was stirred overnight. After addition of water (5 ml), the mixture was heated to 60° C. for 30 min. Ethyl acetate (150 ml) was added, and the organic layer was washed with 0.5 N HCl 2×, 5% K$_2$CO$_3$ 2×, brine 2×. Evaporation of solvent gave an oily residue, which after flash column chromatography (SiO$_2$, 0-30% ethyl acetate in DCM) afforded tert-butyl N-(4-{1-[3-(3,5-dichlorophenyl)-5-oxo-4,5-dihydro-1H-pyrazol-1-yl]ethyl}benzoyl)-β-alaninate as a white solid. NMR (500 MHz, DMSO-d$_6$) δ: 1.37 (s, 9H); 1.78 (d, J=7.1 Hz, 3H); 2.45 (t, J=7.0 Hz, 2H); 3.42 (q, J=7.0 Hz, 2H); 5.56 (q, J=7.1 Hz, 1H); 5.99 (s, 1H); 7.30 (d, J=8.3 Hz, 2H); 7.47 (t, J=1.0 Hz, 1H). 7.73 (d, J=8.3 Hz, 2H); 7.76 (d, J=1.9 Hz, 2H); 8.43 (t, J=5.6 Hz, 1H); 11.34 (s, 1H). MS C$_{25}$H$_{27}$Cl$_2$N$_3$O$_4$ Cald: 503.14; Obsd (M+Na): 526.05.

Step C tert-Butyl N-{4-[1-(3-(3,5-dichlorophenyl)-5-{[(trifluoromethyl)sulfonyl]oxy}-1H-pyrazol-1-yl)ethyl]benzoyl}-β-alaninate tert-Butyl N-(4-{1-[3-(3,5-dichlorophenyl)-5-oxo-4,5-dihydro-1H-pyrazol-1-yl]ethyl}benzoyl)-β-alaninate (2.05 g, 4.06 mmol), TEA (1.7 ml, 12 mmol) were dissolved in THF (35 ml) at −78° C. Triflic anhydride (1.1 ml, 6.2 mmol) was added. The cooling bath was removed and the reaction mixture was stirred for 1 hr. The reaction was quenched by adding ethyl acetate, water. The organic layer was washed with 0.5 N HCl 2×, brine 2×, and dried over Na$_2$SO$_4$. Evaporation of solvent and flash column chromatography (SiO$_2$, 0-10% ethyl acetate in DCM gradient) gave tert-butyl N-{4-[1-(3-(3,5-dichlorophenyl)-5-{[(trifluoromethyl)sulfonyl]oxy}-1H-pyrazol-1-yl)ethyl]benzoyl}-β-alaninate as a colorless dry film. NMR (500 MHz, CDCl$_3$) δ: 1.45 (s, 9H); 1.97 (d, J=7.1 Hz, 3H); 2.53 (t, J=5.9 Hz, 2H); 3.67 (q, J=5.9 Hz, 2H); 5.54 (q, J=7.1 Hz, 1H); 6.43 (s, 1H); 6.86 (t, J=6.2 Hz, 1H); 7.33 (t, J=2.0 Hz, 1H); 7.36 (d, J=8.4 Hz, 2H). 7.67 (d, J=2.0 Hz, 2H); 7.74 (d, J=8.4 Hz, 2H). MS C$_{26}$H$_{26}$Cl$_2$F$_3$N$_3$O$_6$S Cald: 635.09; Obsd (M+Na): 657.89.

tert-Butyl N-{4-[1-(3-(3,5-dichlorophenyl)-5-{[(trifluoromethyl)sulfonyl]oxy}-1H-pyrazol-1-yl)ethyl]benzoyl}-β-alaninate can be resolved via chiral HPLC (ChiralPak AD column, analytical conditions—6% isopropanol/heptane, (S)-isomer R$_f$=16.1 and (R)-isomer 18.1 min, or using SFC chromatography 15% MeOH:CO$_2$, 1.5 mL/min—(R)-isomer R$_f$=5.5 and (S)-isomer 6.1 min, preparative conditions using SFC chromatography 15% MeOH:CO$_2$, 50 mL/min). The (S) isomer was used in Step D.

Alternatively Steps A-C can be carried out using {(1S)-1-[4-(ethoxycarbonyl)phenyl]-ethyl}hydrazinium trifluoroacetate, directly.

Step D. N-(4-{(1S)-1-[5-(5-chloro-1H-indol-2-yl)-3-(3,5-dichlorophenyl)-1H-pyrazol-1-yl]ethyl}benzoyl)-β-alanine tert-butyl N-{4-[(1S)-1-(3-(3,5-dichlorophenyl)-5-{[(trifluoromethyl)sulfonyl]oxy}-1H-pyrazol-1-yl)ethyl]benzoyl}-β-alaninate (15 mmol, 0.024 mmol), triethylamine (14 ul, 0.1 mmol), [1-(tert-Butoxycarbonyl)-5-chloro-1H-indol-2-yl]boronic acid (14 mg, 0.048 mmol) were dissolved DME (0.6 ml). The mixture was de-oxygenated by vacuum-N2 fill cycles. Catalyst Pd(PPh$_3$)$_4$ (3 mg, 10%) was added quickly, and the mixture was de-oxygenated again. After heating in microwave to 100° C. for 10 min, the mixture was diluted with CH$_3$CN:water (containing 5% TFA) and purified with reverse phase HPLC. The collected product was treated with TFA/DCM (1:1, 1 ml) to give, after lyophilization, N-(4-{(1S)-1-[5-(5-chloro-1H-indol-2-yl)-3-(3,5-dichlorophenyl)-1H-pyrazol-1-yl]ethyl}benzoyl)-β-alanine as a white powder. H$^1$-NMR (DMSO-d$_6$, 500 MHz) δ: 8.42 (1H, t); 7.90 (2H, s); 7.75 (2H, d); 7.60 (2H, d); 7.40 (1H, d); 7.28 (1H, s); 7.22 (2H, d); 7.18 (1H, d); 6.58 (1H, s), 6.50 (1H, s); 6.02 (1H, dd); 3.40 (2H, dd); 1.95 (3H, d). MS Cald for C$_{29}$H$_{23}$Cl$_3$N$_4$O$_3$: 580.08. Obsd: 581.13.

Example 53

N-(4-{(1S)-1-[5-(6-CHLORO-1H-INDOL-2-YL)-3-(3,5-DICHLOROPHENYL)-1H-PYRAZOL-1-YL]ETHYL}BENZOYL)-β-ALANINE

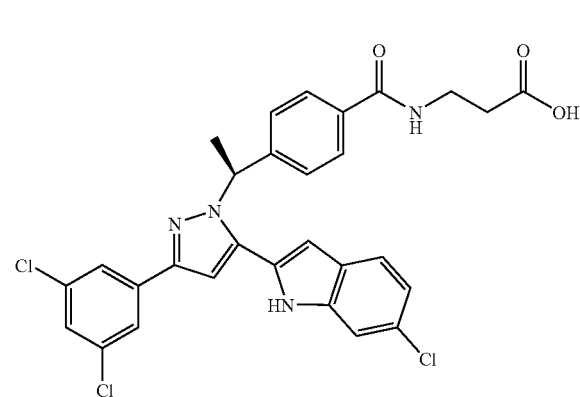

This compound was made in a similar method as example 52. H$^1$-NMR (DMSO-d$_6$, 500 MHz): δ: 8.42 (1H, t); 7.90 (2H, s); 7.75 (2H, d); 7.58 (2H, m); 7.41 (1H, s); 7.30 (1H, s); 7.22 (2H, d); 7.05 (1H, d); 6.60 (1H, s); 6.05 (1H, dd); 3.40 (1H, dd); 1.85 (3H, d).

MS Cald for C$_{29}$H$_{23}$Cl$_3$N$_4$O$_3$: 580.08. Obsd: 581.09.

Example 54

N-[4-((1S)-1-{3-(3,5-DICHLOROPHENYL)-5-[6-(TRIFLUOROMETHYL)-1H-INDOL-2-YL]-1H-PYRAZOL-1-YL}ETHYL)BENZOYL]-β-ALANINE

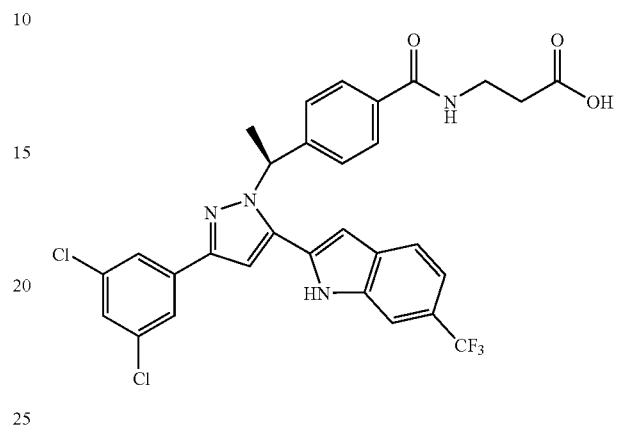

This compound was made in a similar method as example 52. H$^1$-NMR (DMSO-d$_6$, 500 MHz) δ: 8.42 (1H, t); 7.92 (2H, s); 7.78 (1H, d); 7.75 (3H, m); 7.35 (2H, s); 7.22 (2H, d); 6.76 (1H, s); 6.05 (1H, dd); 3.40 (2H, dd); 1.95 (3H, d). MS Cald for C$_{30}$H$_{23}$Cl$_2$F$_3$N$_4$O$_3$: 614.11; Obsd: 637.09.

Example 55

N-(4-{(1S)-1-[3-(3,5-DICHLOROPHENYL)-5-(5-METHOXY-1H-INDOL-2-YL)-1H-PYRAZOL-1-YL]ETHYL}BENZOYL)-β-ALANINE

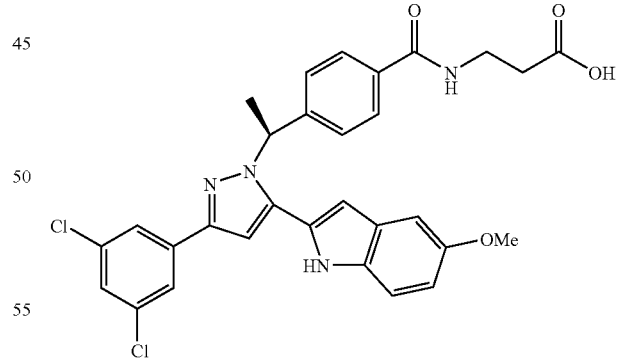

This compound was made in a similar method as example 52. H$^1$-NMR (DMSO-d$_6$, 500 MHz): δ: 8.42 (1H, t); 7.90 (2H, s); 7.75 (2H, d); 7.59 (1H, s); 7.30 (1H, d); 7.22 (3H, m); 7.02 (1H, s); 6.80 (1H, d); 6.45 (1H, s); 6.05 (1H, dd); 3.72 (3H, s); 3.40 (2H, dd); 1.95 (3H, d); MS Cald for C$_{30}$H$_{26}$Cl$_2$N$_4$O$_4$: 576.13; Obsd: 577.23.

Example 56

N-(4-{(1S)-1-[3-(3,5-DICHLOROPHENYL)-5-(1H-INDOL-2-YL)-1H-PYRAZOL-1-YL]ETHYL}BENZOYL)-β-ALANINE

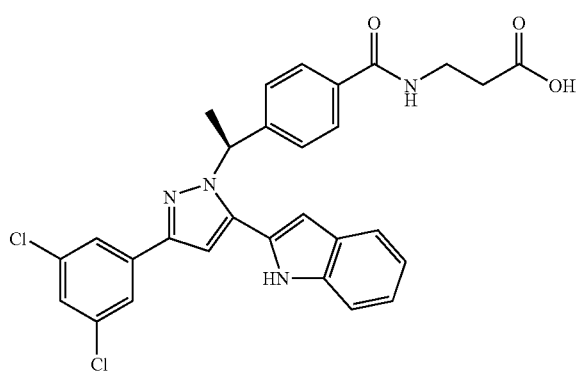

This compound was made in a similar method as example 52. $H^1$-NMR (DMSO-$d_6$, 500 MHz): δ 8.42 (1H, t); 7.90 (2H, s); 7.77 (2H, d); 7.59 (1H, s); 7.58 (1H, d); 7.40 (1H, d); 7.23 (1H, s); 7.22 (2H, d); 7.18 (1H, t); 7.01 (1H, t); 6.59 (1H, s); 6.05 (1H, dd); 3.4 (2H, dd); 2.48 (2H, dd); 1.95 (3H, d). MS Cald for $C_{29}H_{24}Cl_2N_4O_3$: 546.12; Obsd: 547.17.

Example 57

N-(4-{(1S)-1-[3-[2-FLUORO-5-(TRIFLUOROMETHYL)PHENYL]-5-(1H-INDOL-2-YL)-1H-PYRAZOL-1-YL]ETHYL}BENZOYL)-β-ALANINE

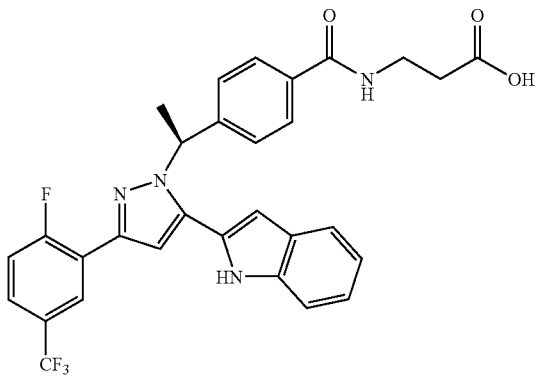

This compound was made in a similar method as example 52. $H^1$-NMR (DMSO-$d_6$, 500 MHz) δ: 8.42 (1H, t); 8.35 (1H, d); 7.80 (1H, m); 7.75 (2H, d); 7.60 (1H, t); 7.55 (1H, d); 7.40 (1H, d), 7.25 (2H, d); 7.22 (1H, d); 7.15 (1H, t); 7.00 (1H, t); 6.60 (1H, s); 6.18 (1H, dd); 1.98 (3H, d). MS Cald for $C_{30}H_{24}F_4N_4O_3$: 564.18; Obsd: 565.26.

Example 58

N-(4-{[5-(1-BENZOFURAN-2-YL)-3-(3,5-DICHLOROPHENYL)-1H-PYRAZOL-1-YL]METHYL}BENZOYL)-β-ALANINE

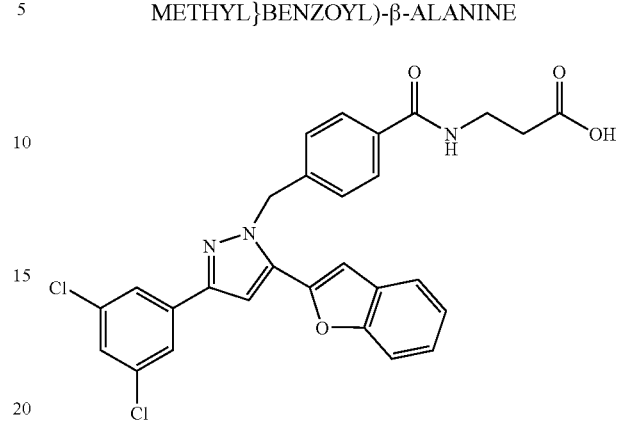

This compound was made in a similar method as example 52 starting from commercially available 2-benzofuran boronic acid. NMR (500 MHz, DMSO-$d_6$)) δ: 2.44 (t, J=7.0 Hz, 2H); 3.39 (q, J=7 Hz, 2H); 5.83 (s, 2H); 7.23 (s, 1H); 7.26 (d, J=8.2 Hz, 2H); 7.29 (t, J=8.0 Hz, 1H); 7.37 (t, J=7.6 Hz, 1H); 7.59 (t, J=1.9 Hz, 1H); 7.60 (s, 1H); 7.63 (d, J=8.0 Hz, 1H); 7.68 (d, J=7.6 Hz, 1H); 7.75 (d, J=8.2 Hz, 2H); 7.94 (d, J=1.9 Hz, 2H); 8.46 (t, J=6 Hz, 1H). MS Cald for $C_{30}H_{24}F_4N_4O_3$: 533.09; Obsd: 534.28.

Example 59

N-[4-({5-(1-BENZOFURAN-2-YL)-3-[2-PROPOXY-4-(TRIFLUOROMETHYL)PHENYL]-1H-PYRAZOL-1-YL}METHYL)BENZOYL]-β-ALANINE

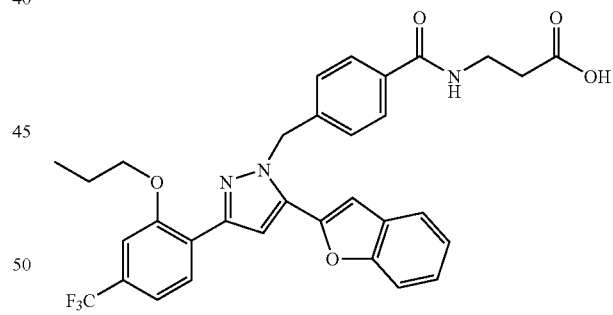

This compound was made in a similar method as example 52. NMR (500 MHz, DMSO-$d_6$)) δ: 1.07 (t, J=7.3 Hz, 3H); 1.88 (h, J=7.3 Hz, 2H); 2.43 (t, J=7.0 Hz, 2H); 3.39 (q, J=7 Hz, 2H); 4.19 (t, J=6.6 Hz, 2H); 5.84 (s, 2H); 7.2-7.3 (m, 4H); 7.34-7.41 (m, 4H); 7.64 (d, J=8.6 Hz, 1H); 7.67 (d, J=7.6 Hz, 1H); 7.75 (d, J=8.2 Hz, 2H); 8.17 (d, J=8.1 Hz, 1H); 8.47 (t, J=5.2 Hz, 1H). MS Cald for $C_{32}H_{28}F_3N_3O_5$: 591.20; Obsd: 592.36.

Biological Assays

The ability of the compounds of the present invention to inhibit the binding of glucagon and their utility in treating or preventing type 2 diabetes mellitus and the related conditions can be demonstrated by the following in vitro assays.

Glucagon Receptor Binding Assay

A stable CHO (Chinese hamster ovary) cell line expressing cloned human glucagon receptor was maintained as described (Chicchi et al. *J Biol Chem* 272, 7765-9 (1997); Cascieri et al. *J Biol Chem* 274, 8694-7 (1999)). To determine antagonistic binding affinity of compounds 0.002 mg of cell membranes from these cells were incubated with $^{125}$I-Glucagon (New England Nuclear, Mass.) in a buffer containing 50 mM Tris-HCl (pH 7.5), 5 mM $MgCl_2$, 2 mM EDTA, 12% Glycerol, and 0.200 mg WGA coated PVT SPA beads (Amersham), +/− compounds or 0.001 mM unlabeled glucagon. After 4-12 hours incubation at room temperature, the radioactivity bound to the cell membranes was determined in a radioactive emission detection counter (Wallac-Microbeta). Data was analyzed using the software program Prism® from GraphPad. The $IC_{50}$ were calculated using non-linear regression analysis assuming single site competition.

Inhibition of Glucagon-Stimulated Intracellular cAMP Formation

Exponentially growing CHO cells expressing human glucagon receptor were harvested with the aid of enzyme-free dissociation media (Specialty Media), pelleted at low speed, and re-suspended in cell suspension buffer [75 mM Tris-HCl pH7.5, 250 mM Sucrose, 25 mM $MgCl_2$, 1.5 mM EDTA, 0.1 mM Ro-20-1724 (Biomol, Inc.), 0.2% bovine serum albumin and one tablet of completed (Boehringer), which contains a cocktail of protease inhibitors, for each 50 ml of buffer]. An adenylate cyclase assay was setup using an Adenylate Cyclase Assay kit (SMP-004B) from New England Nuclear (NEN) as per manufacturer instructions. Briefly, compounds were diluted from stocks in a cell stimulation buffer supplied with the kit. Cells prepared as above were preincubated in flash plates coated with anti-cAMP antibodies (NEN) in presence of compounds or DMSO controls for 40 minutes, and then stimulated with glucagon (250 pM) for an additional 40 minutes. The cell stimulation was stopped by addition of equal amount of a detection buffer containing lysis buffer as well as $^{125}$I-labeled cAMP tracer (NEN). After 3-6 h of incubation at room temperature the bound radioactivity was determined in a liquid scintillation counter (TopCount-Packard Instruments). Activity of test compounds was calculated by comparing to the total scintillation signal (CPM) of control samples with no compound and with 0.001 mM unlabeled-glucagon.

Certain embodiments of the invention has been described in detail; however, numerous other embodiments are contemplated as falling within the invention. Thus, the claims are not limited to the specific embodiments described herein. All patents, patent applications and publications that are cited herein are hereby incorporated by reference in their entirety.

What is claimed is:

1. A compound represented by formula I:

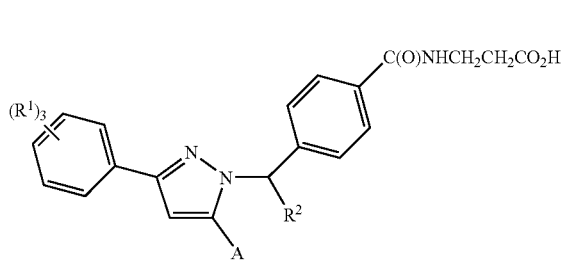

I or a pharmaceutically acceptable salt or solvate thereof, wherein:

A represents a 9-10 membered bicyclic heteroaryl group containing 1-4 heteroatoms, 0-4 of which are N and 0-1 of which are O or S, said bicyclic heteroaryl group being optionally substituted as follows:

e) 1-5 halo groups;

f) 1 $CO_2R^a$; $S(O)_pR^d$; OH, CN, $NO_2$; $C(O)NR^bR^c$ and $NR^bR^c$;

c) 1-2 $C_{1-10}$alkyl or $OC_{1-10}$alkyl, said groups being optionally substituted with:

(1) 1-5 halo groups up to a perhaloalkyl group;

(2) 1 oxo group;

(3) 1-2 OH groups;

(4) 1-2 $C_{1-10}$alkoxy groups, each optionally substituted with:
up to five halo or a perhaloalkoxy, 1 OH or $CO_2R^a$ group;

(5) 1 $CO_2R^a$ or $S(O)_pR^d$;

(6) 1-2 Aryl, Hetcy or HAR groups, each optionally substituted as follows:

(a) 1-5 halo groups, (b) 1 OH, $CO_2R^a$, CN, $S(O)_pR^d$, $NO_2$ or $C(O)NR^bR^c$, and (c) 1-2 $C_{1-10}$alkyl or alkoxy groups, each optionally substituted with:

1-5 halo, up to perhaloalkyl, and 1-2 OH or $CO_2R^a$ groups; and d) Aryl, HAR, Hetcy, each optionally substituted as set forth below:

(1) 1-3 $C_{1-10}$alkyl or alkoxy groups optionally substituted as follows: 1-5 halo groups; 1-2 OH groups; $CO_2R^a$; CN; $S(O)_pR^d$; phenyl optionally substituted as follows: (i) 1-5 halo groups, (ii) 1 $CO_2R^a$, CN, $S(O)_pR^d$, $NO_2$ or $C(O)NR^bR^c$ group, (iii) 1-2 $C_{1-10}$alkyl or alkoxy groups, each optionally substituted with: 1-5 halo, up to perhaloalkyl, and 1-2 OH or $CO_2R^a$ groups; and said Aryl, HAR, Hetcy group d) being further optionally substituted on carbon by a group selected from the group consisting of;

(2) 1-5 halo groups;

(3) 1-2 OH groups;

(4) 1 $S(O)_pR^d$, $NO_2$ or CN group;

(5) 1-2 $CO_2R^a$; and (6) —$C(O)NR^bR^c$;

$R^a$ is H or $C_{1-10}$alkyl, optionally substituted with phenyl, OH, $OC_{1-6}$alkyl, $CO_2H$, $CO_2C_{1-6}$alkyl and 1-3 halo groups;

$R^b$ is H or $C_{1-10}$alkyl;

$R^c$ is H or is independently selected from:

(a) $C_{1-10}$alkyl, optionally substituted with OH, $OC_{1-6}$alkyl, $CO_2H$, $CO_2C_{1-6}$alkyl, and 1-3 halo groups;

(b) Aryl or Ar—$C_{1-6}$alkyl, each optionally substituted with 1-5 halos and 1-3 members selected from the group consisting of: CN, OH, $C_{1-10}$alkyl and $OC_{1-10}$alkyl, said alkyl and alkoxy being further optionally substituted with 1-5 halo groups up to perhalo;

(c) Hetcy or Hetcy-$C_{1-6}$alkyl, optionally substituted with 1-5 halo groups and 1-3 groups selected from: oxo, $C_{1-10}$alkyl and $OC_{1-10}$alkyl, said alkyl and alkoxy being further optionally substituted with 1-5 halo groups up to perhalo; and (d) HAR or HAR-$C_{1-6}$alkyl, optionally substituted with 1-5 halo groups and 1-3 groups selected from: $C_{1-10}$alkyl and $OC_{1-10}$ alkyl, said alkyl and alkoxy being further optionally substituted with 1-5 halo groups up to perhalo;

$R^d$ is $C_{1-10}$alkyl, Aryl or Ar—$C_{1-10}$alkyl; and p is an integer selected from 0, 1 and 2;

each $R^1$ represents H or is selected from the group consisting of:

a) halo; $CO_2R^a$; $S(O)_pR^d$; OH, CN, $NO_2$; $C(O)NR^bR^c$ and $NR^bR^c$;

b) $C_{1-10}$alkyl or $OC_{1-10}$alkyl, said groups being optionally substituted with:
  (1) 1-5 halo groups up to a perhaloalkyl group;
  (2) 1 oxo group;
  (3) 1-2 OH groups;
  (4) 1-2 $C_{1-10}$alkoxy groups, each optionally substituted with:
    up to five halo or a perhaloalkoxy, 1 OH or $CO_2R^a$ group;
  (5) 1 $CO_2R^a$ or $S(O)_pR^d$;
  (6) 1-2 Aryl, Hetcy or HAR groups, each optionally substituted as follows:
    (a) 1-5 halo groups,
    (b) 1 OH, $CO_2R^a$, CN, $S(O)_pR^d$, $NO_2$ or $C(O)NR^bR^c$, and
    (c) 1-2 $C_{1-10}$alkyl or alkoxy groups, each optionally substituted with:
1-5 halo, up to perhaloalkyl, and 1-2 OH or $CO_2R^a$ groups;

c) Aryl, HAR, Hetcy, each optionally substituted as set forth below:
  (1) 1-3 $C_{1-10}$alkyl or alkoxy groups optionally substituted as follows: 1-5 halo groups; 1-2 OH groups; $CO_2R^a$; CN; $S(O)_pR^d$, phenyl optionally substituted as follows: (i) 1-5 halo groups, (ii) 1 $CO_2R^a$, CN, $S(O)_pR^d$, $NO_2$ or $C(O)NR^bR^c$ group, (iii) 1-2 $C_{1-10}$alkyl or alkoxy groups, each optionally substituted with: 1-5 halo, up to perhaloalkyl, and 1-2 OH or $CO_2R^a$ groups; and said Aryl, HAR, Hetcy group c) being further optionally substituted on carbon by a group selected from the group consisting of:
  (2) 1-5 halo groups;
  (3) 1-2 OH groups;
  (4) 1 $S(O)_pR^d$, $NO_2$ or CN group;
  (5) 1-2 $CO_2R^a$; and
  (6) —$C(O)NR^bR^c$, wherein $R^a$, $R^b$, $R^c$, $R^d$, and p are as previously defined, and $R^2$ is selected from hydrogen and $C_{1-6}$alkyl.

2. A compound in accordance with claim 1 wherein:

A represents a 9-10 membered bicyclic heteroaryl group containing 1-3 heteroatoms, 0-3 of which are N and 0-1 of which are O or S, said bicyclic heteroaryl group being optionally substituted as follows:
a) 1-5 halo groups;
b) 1 $CO_2R^a$; $S(O)_pR^d$; OH, CN;
c) 1-2 $C_{1-10}$alkyl or $OC_{1-10}$alkyl, said groups being optionally substituted with:
  (1) 1-5 halo groups up to a perhaloalkyl group;
  (2) 1-2 $C_{1-10}$alkoxy groups, each optionally substituted with:
    up to five halo or a perhaloalkoxy, 1 OH or $CO_2R^a$ group.

3. A compound in accordance with claim 1 wherein:

each $R^1$ represents H or is selected from the group consisting of:
a) halo; $CO_2R'$; $S(O)_pR^d$; OH, CN;
b) $C_{1-10}$alkyl or $OC_{1-10}$alkyl, said groups being optionally substituted with:
  (1) 1-5 halo groups up to a perhaloalkyl group;
  (2) 1 oxo group;
  (3) 1-2 OH groups;
  (4) 1-2 $C_{1-10}$alkoxy groups, each optionally substituted with:
    up to five halo or a perhaloalkoxy, 1 OH or $CO_2R^a$ group; and
  (5) 1 $CO_2R^a$ or $S(O)_pR^d$.

4. A compound in accordance with claim 1 wherein

A represents a 9-10 membered bicyclic heteroaryl group containing 1-3 heteroatoms, 0-3 of which are N and 0-1 of which are O or S, said bicyclic heteroaryl group being optionally substituted as follows:
a) 1-5 halo groups;
b) 1 $CO_2R^a$; $S(O)_pR^d$; OH, CN;
c) 1-2 $C_{1-10}$alkyl or $OC_{1-10}$alkyl, said groups being optionally substituted with:
  (1) 1-5 halo groups up to a perhaloalkyl group;
  (2) 1-2 $C_{1-10}$alkoxy groups, each optionally substituted with:
    up to five halo or a perhaloalkoxy, 1 OH or $CO_2R^a$ group; and each $R^1$ represents H or is selected from the group consisting of:
a) halo; $CO_2R^a$; $S(O)_pR^d$; OH, CN;
b) $C_{1-10}$alkyl or $OC_{1-10}$alkyl, said groups being optionally substituted with:
  (1) 1-5 halo groups up to a perhaloalkyl group;
  (2) 1 oxo group;
  (3) 1-2 OH groups;
  (4) 1-2 $Cl_{1-10}$alkoxy groups, each optionally substituted with:
    up to five halo or a perhaloalkoxy, 1 OH or $CO_2R^a$ group; and
  (5) 1 $CO_2R^a$ or $S(O)_pR^d$.

5. A compound in accordance with claim 1 wherein:

A represents a 9-10 membered bicyclic heteroaryl group selected from the group consisting of: indole, benzimidazole, benzthiazole, benzoxazole, benzofuran, quinoline, isoquinoline and quinaxoline, said group being optionally substituted as follows:
a) 1-5 halo groups
b) 1 OH group;
c) 1-2 $C_{1-10}$alkyl or $OC_{1-10}$alkyl groups, said groups being optionally substituted with 1-5 halo groups, up to perhaloalkyl;

and each R1 represents H or is selected from the group consisting of:
a) halo;
b) $C_{1-10}$alkyl or $OC_{1-10}$ alkyl, optionally substituted with 1-5 halo groups up to perhaloalkyl; and $R_2$ is H or methyl.

6. A compound in accordance with claim 1 selected from the group consisting of:
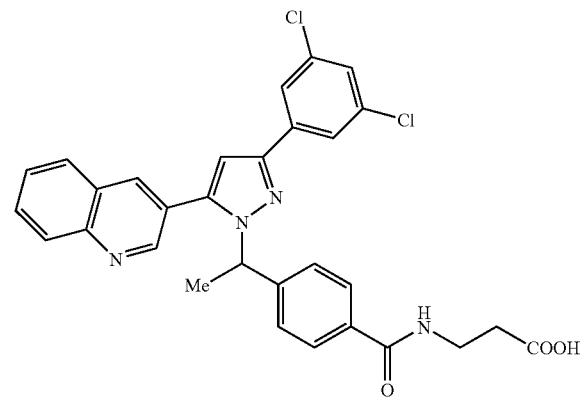
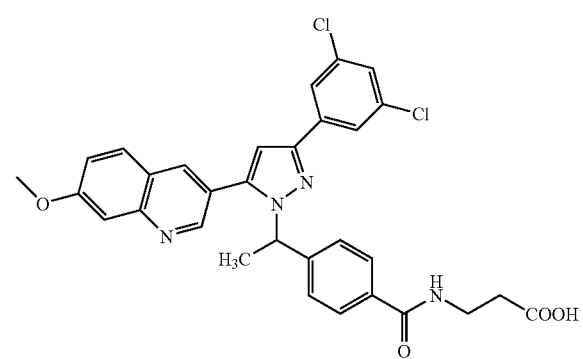
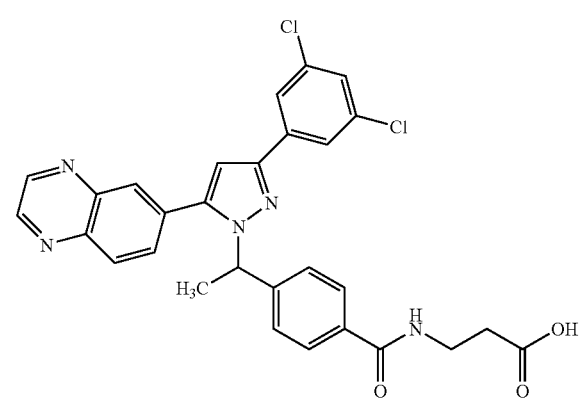
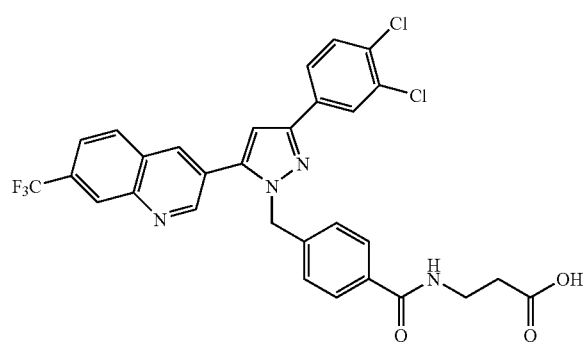
-continued
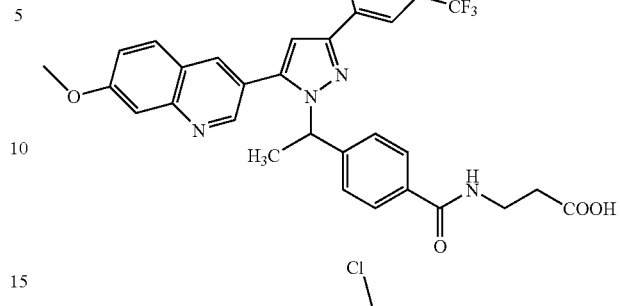
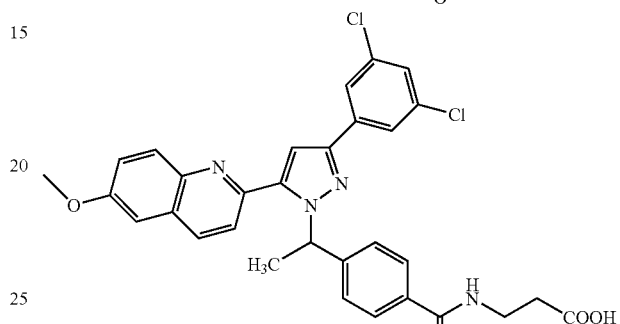
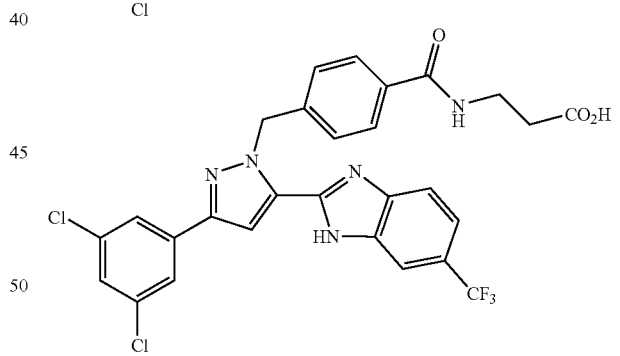
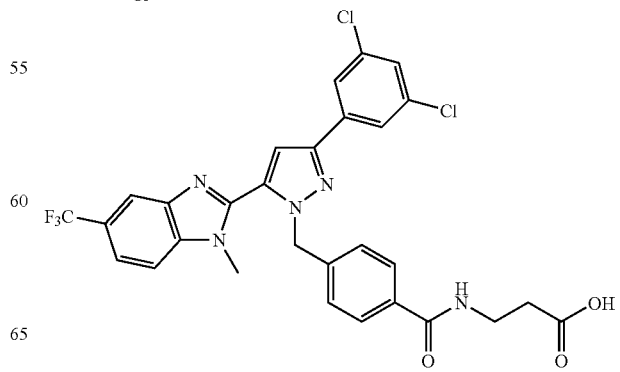

-continued
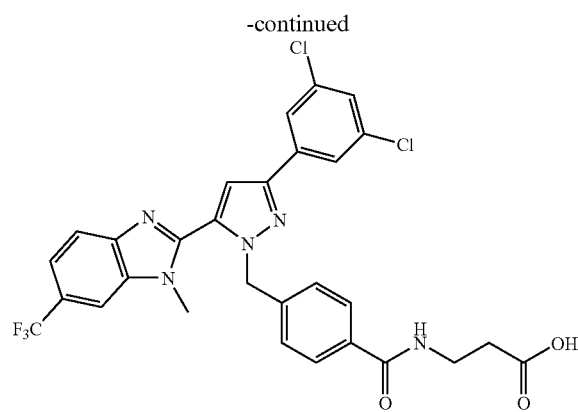
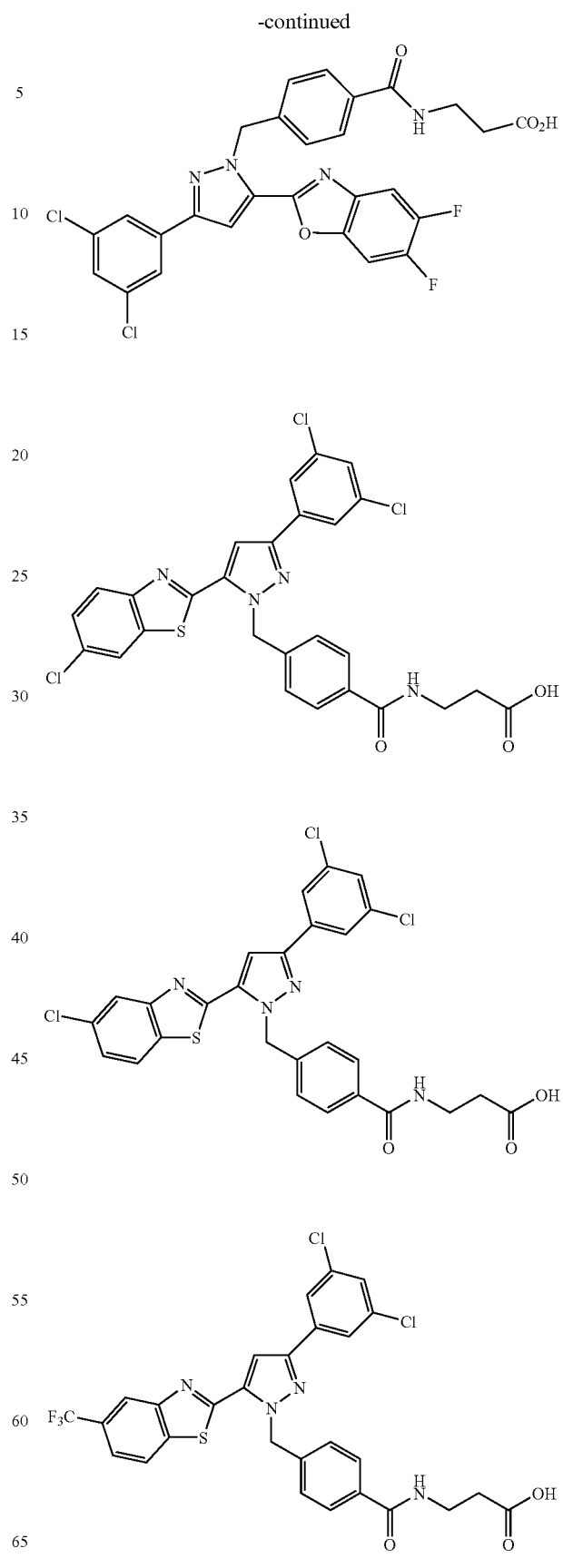

81
-continued
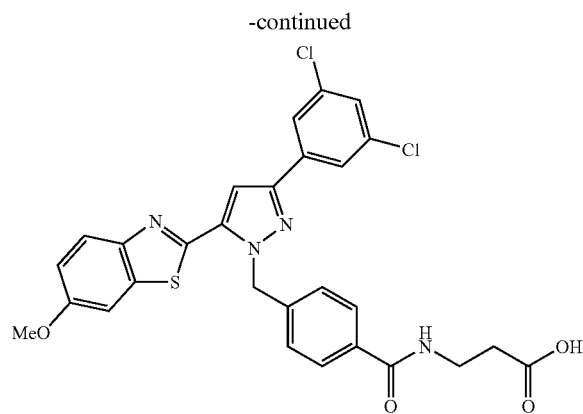
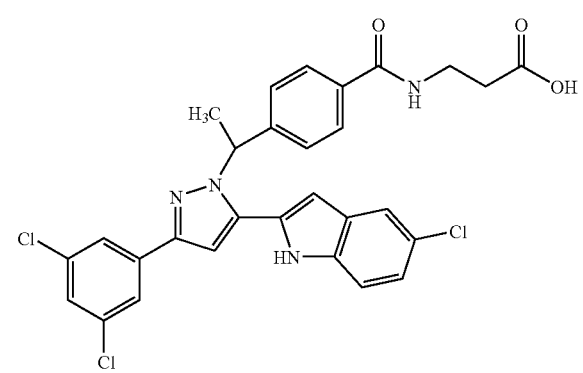
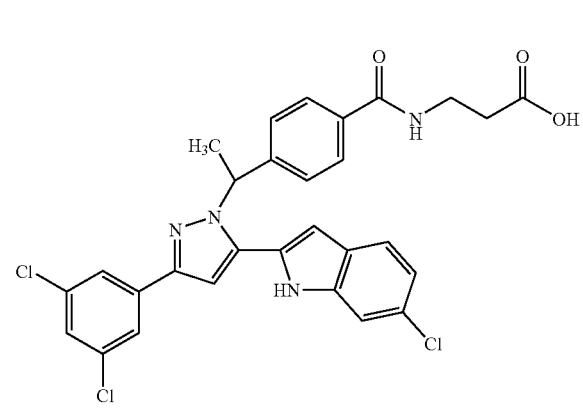
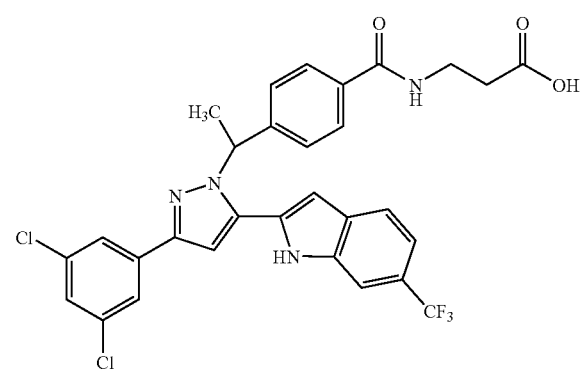
82
-continued
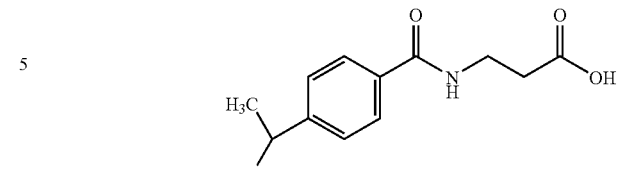
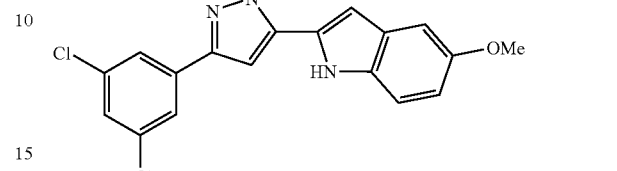
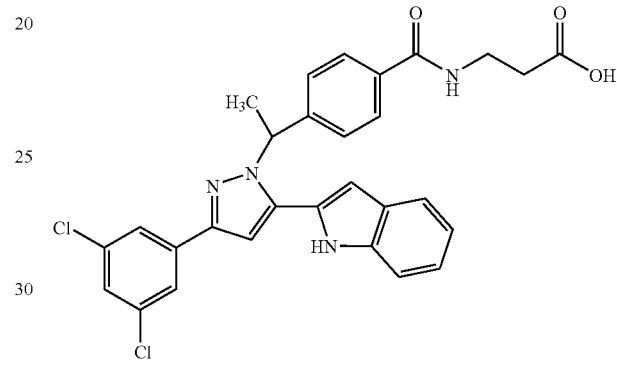
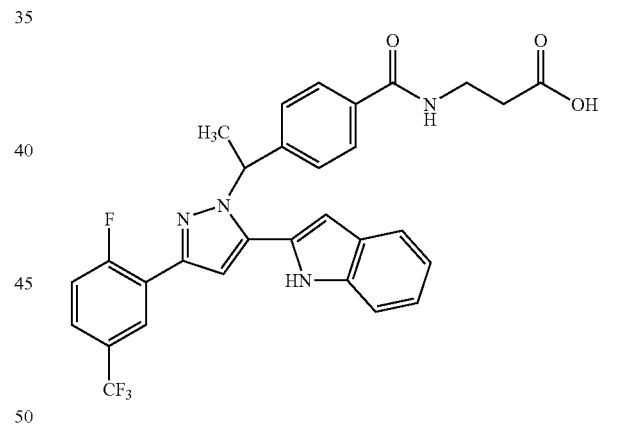
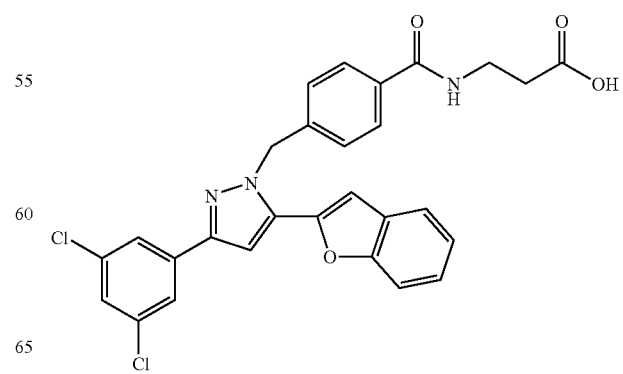

-continued
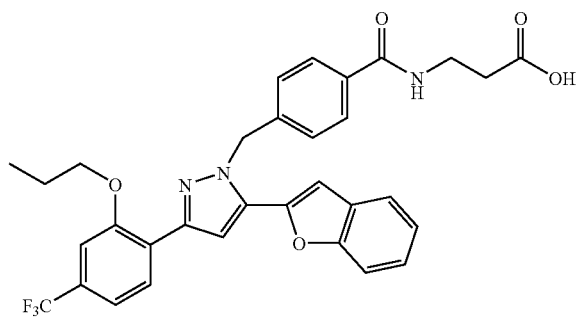
TABLE 1
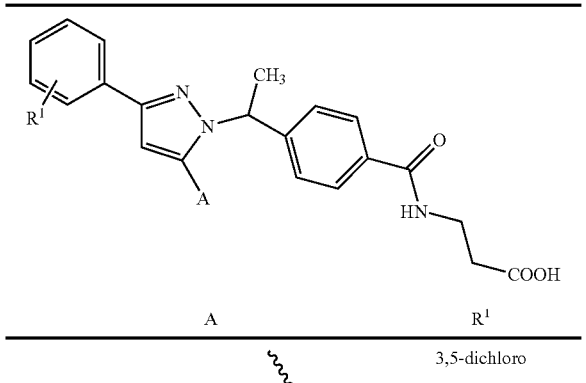
| A | R[1] |
|---|---|
| isoquinolin-3-yl | 3,5-dichloro |
| quinolin-2-yl | 3,5-dichloro |
| quinoxalin-2-yl | 3,5-dichloro |
| quinoxalin-2-yl | 2Cl-5-CF3 |
| quinolin-6-yl | 3,5-dichloro |
| 7-CF3-quinolin-3-yl | 3,5-dichloro |
TABLE 1-continued
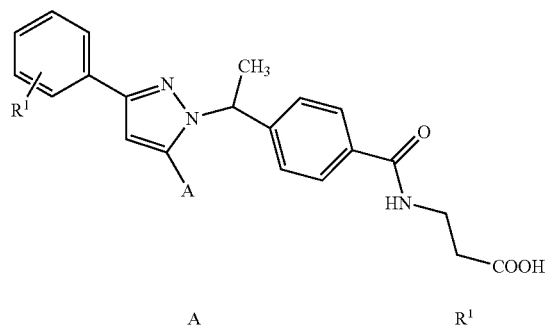
| A | R[1] |
|---|---|
| 6-OCF3-quinolin-3-yl | 3,5-dichloro |
| 7-OCF3-quinolin-3-yl | 3,5-dichloro |
| 7-CF3-quinolin-3-yl | 2F-5-CF3 |
| 7-OCF3-quinolin-3-yl | 2F-5-CF3 |
| 7-OMe-quinolin-3-yl | 2F-5-CF3 |
| 7-OMe-quinolin-3-yl | 3,4-dichloro |
| 7-OCF3-quinolin-3-yl | 3,4-dichloro |
| 7-CF3-quinolin-3-yl | 3,4-dichloro |

TABLE 1-continued
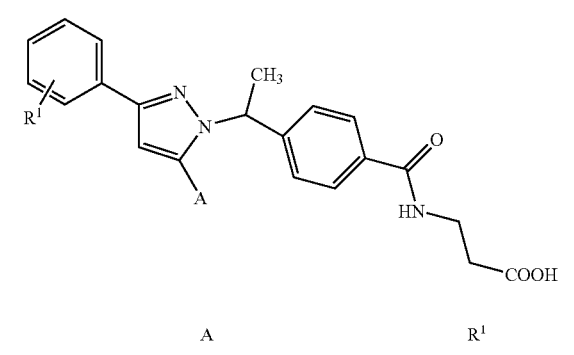
| A | R¹ |
|---|---|
| 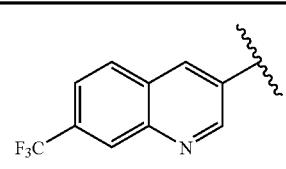 | 2F-4-CF₃ |
| 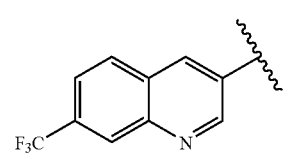 | 2Cl-5-CF₃ |
| 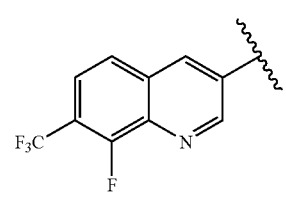 | 3,5-dichloro |
| 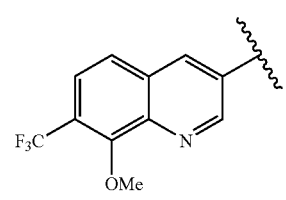 | 3,5-dichloro |
| 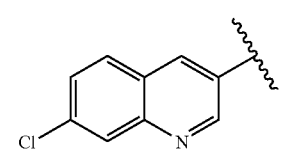 | 3,5-dichloro |
| 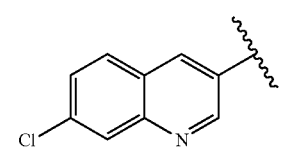 | 3,4-dichloro |
| 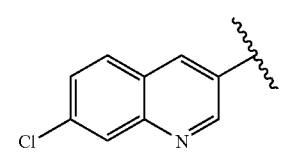 | 2F-4-CF₃ |
TABLE 1-continued
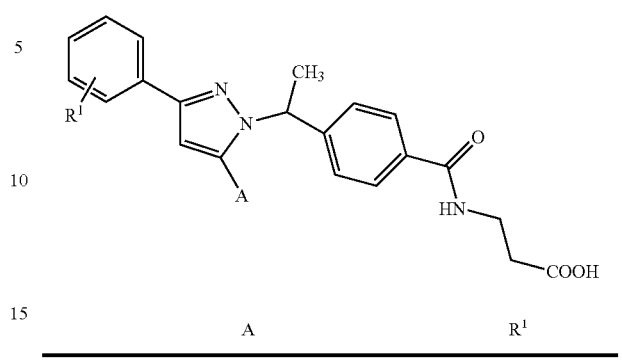
| A | R¹ |
|---|---|
| 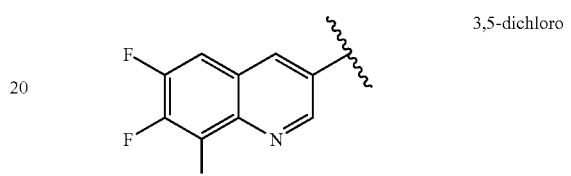 | 3,5-dichloro |
| 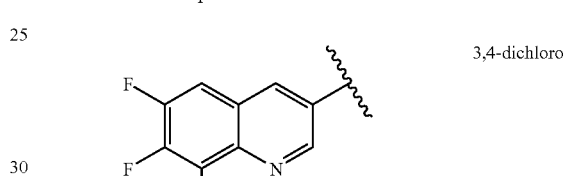 | 3,4-dichloro |
| 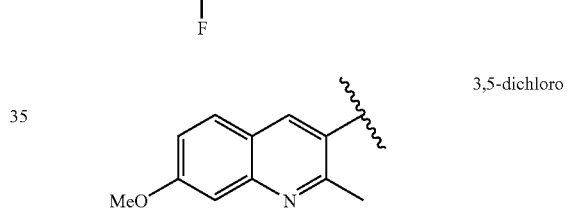 | 3,5-dichloro |
| 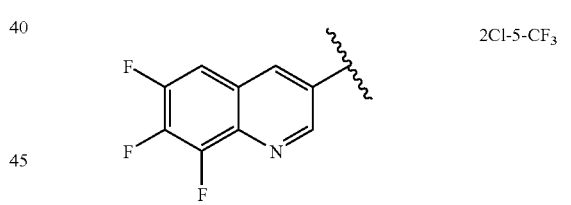 | 2Cl-5-CF₃ |
| 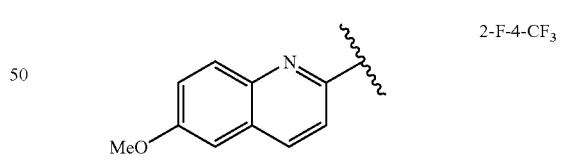 | 2-F-4-CF₃ |
| 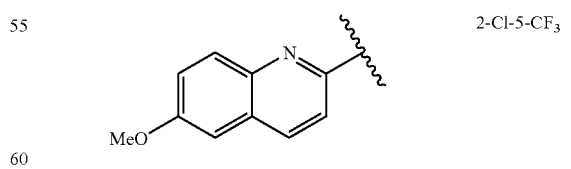 | 2-Cl-5-CF₃ |
| 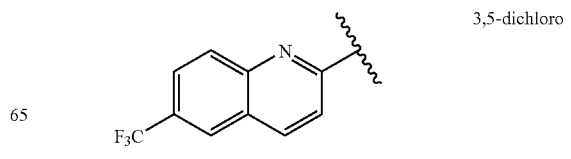 | 3,5-dichloro |

TABLE 1-continued

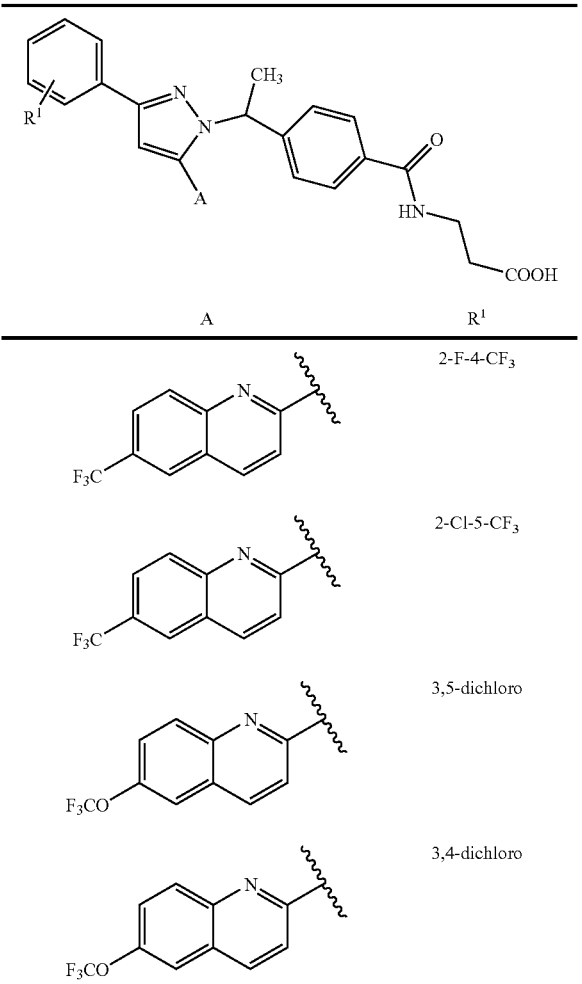

| A | R¹ |
|---|----|
| 6-trifluoromethyl-quinolin-2-yl (F₃C-quinoline) | 2-F-4-CF₃ |
| 6-trifluoromethyl-quinolin-2-yl (F₃C-quinoline) | 2-Cl-5-CF₃ |
| 6-trifluoromethoxy-quinolin-2-yl (F₃CO-quinoline) | 3,5-dichloro |
| 6-trifluoromethoxy-quinolin-2-yl (F₃CO-quinoline) | 3,4-dichloro |

TABLE 1-continued

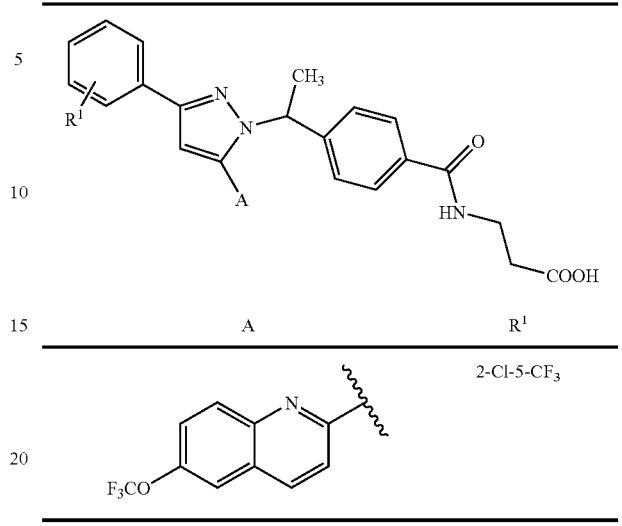

| A | R¹ |
|---|----|
| 6-trifluoromethoxy-quinolin-2-yl (F₃CO-quinoline) | 2-Cl-5-CF₃ | or a pharmaceutically acceptable salt or solvate thereof.

7. A pharmaceutical composition comprising a compound in accordance with claim 1 in combination with a pharmaceutically acceptable carrier.

8. A method of treating type 2 diabetes mellitus in a mammalian patient in need of such treatment comprising administering to said patient a compound in accordance with claim 1 in an amount that is effective to treat said type 2 diabetes mellitus.

9. A method of treating atherosclerosis in a mammalian patient in need of such treatment, comprising administering to said patient a compound in accordance with claim 1 in an amount effective to treat atherosclerosis.

\* \* \* \* \*